United States Patent
Warren et al.

(10) Patent No.: US 6,268,188 B1
(45) Date of Patent: *Jul. 31, 2001

(54) TRANSAMINASES AND AMINOTRANSFERASES

(75) Inventors: Patrick V. Warren, Philadelphia; Ronald V. Swanson, Media, both of PA (US)

(73) Assignee: Diversa Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,184

(22) Filed: Oct. 4, 1999

Related U.S. Application Data

(63) Continuation of application No. 08/646,590, filed on May 8, 1996, now Pat. No. 5,962,283, which is a continuation-in-part of application No. 08/599,171, filed on Feb. 9, 1996, now Pat. No. 5,814,473.

(51) Int. Cl.[7] .............................. C12P 13/14; C12N 9/10; C12N 1/20; C12N 15/00; C07H 21/04
(52) U.S. Cl. .................. 435/128; 435/252.3; 435/320.1; 435/822; 435/193; 435/110; 536/23.2
(58) Field of Search ..................................... 435/110, 128, 435/193, 282.3, 320.1, 822; 536/23.2

(56) References Cited

U.S. PATENT DOCUMENTS 6,013,509 * 1/2000 Warren et al. .................... 435/252.3

FOREIGN PATENT DOCUMENTS

| 0 786 519 | 7/1997 | (EP) . |
| WO 98 07830 | 2/1998 | (WO) . |

OTHER PUBLICATIONS

Database WP I Section Ch, Week 198826, Derwent Publications Ltd., London, GB; Class B04, AN 1988–177722, XP002130562; & JP 63 112985 A (Daicel Chem), May 18,1988 (abstract).

Fernandez–Herrero et al., "glmS of Thermus thermophilus HB8: an essential gene for cell–wall synthesis identified immediately upstream of the S–layer gene," *Molecular Microbiology*, 17(1):1–12 (Jul. 1995).

Limauro et al., "Cloning and characterization of the histidine biosynthetic gene cluster of *Streptomyces coelicolor* A3(2)," *Gene* 90(1):31–41 (May 31, 1990).

Okamoto et al., "An Aspartate Aminotransferase from an Extremely Thermophilic Bacterium, *Thermus thermolphilus* HB8," *Journal of Biochemistry*, 119(1):135–144 (Jan. 1996).

Brown and Doolittle, "Root of the universal tree of life based on ancient aminoacyl–tRNA synthetase gene duplications," *Proc. Natl. Acad. Sci. USA* 92 (7):2441–2445 (1995).

Völkl, et al., "Genomic and cDNA sequence tags of the hyperthermophilic Archaeon *Pyrobaculum aerophilum*, " *Nucleic Acids Research* 24 (22):4373–4378 (1996).

Wetmur, et al., "Cloning, Sequencing, and Expression of RecA Proteins from Three Distantly Related Thermophilic Eubacteria," *Thr Journal of Biological Chemistry* 269 (41):25928–25935 (1994).

Sung, Moon–Hee et al., *Thermostable Aspartate Aminotransferase from a Thermophilic Bacillus Species*, The Journal of Biological Chemistry, vol. 266, No. 4, Issue of Feb. 5, 1991, pp. 2567–2572.

* cited by examiner

*Primary Examiner*—Elizabeth Slobodyansky
(74) *Attorney, Agent, or Firm*—Gray Cary Ware & Freidenrich LLP; Lisa A. Haile

(57) ABSTRACT

Thermostable transaminase and aminotransferase enzymes derived from various *ammonife* and *aquifex* organisms are disclosed. The enzymes are produced from native or recombinant host cells and can be utilized in the pharmaceutical, agricultural and other industries.

10 Claims, 20 Drawing Sheets

| | |
|---|---|
| ATG ATT GAA GAC CCT ATG GAC TGG GCT TTT CCG AGG ATA AAG AGA CTG<br>Met Ile Glu Asp Pro Met Asp Trp Ala Phe Pro Arg Ile Lys Arg Leu<br>　　　　　　　　5　　　　　　　　　　　　10　　　　　　　　　　　15 | 48 |
| CCT CAG TAT GTC TTC TCT CTC GTT AAC GAA CTC AAG TAC AAG CTA AGG<br>Pro Gln Tyr Val Phe Ser Leu Val Asn Glu Leu Lys Tyr Lys Leu Arg<br>　　　　　　　　20　　　　　　　　　　25　　　　　　　　　　　30 | 96 |
| CGT GAA GGC GAA GAT GTA GTG GAT CTT GGT ATG GGC AAT CCT AAC ATG<br>Arg Glu Gly Glu Asp Val Val Asp Leu Gly Met Gly Asn Pro Asn Met<br>　　　　35　　　　　　　　　　　40　　　　　　　　　　　45 | 144 |
| CCT CCA GCA AAG CAC ATA ATA GAT AAA CTC TGC GAA GTG GCT CAA AAG<br>Pro Pro Ala Lys His Ile Ile Asp Lys Leu Cys Glu Val Ala Gln Lys<br>　　　50　　　　　　　　　　　55　　　　　　　　　　　60 | 192 |
| CCG AAC GTT CAC GGA TAT TCT GCG TCA AGG GGC ATA CCA AGA CTG AGA<br>Pro Asn Val His Gly Tyr Ser Ala Ser Arg Gly Ile Pro Arg Leu Arg<br>65　　　　　　　　　　70　　　　　　　　　　　75　　　　　　　　　　80 | 240 |
| AAG GCT ATA TGT AAC TTC TAC GAA GAA AGG TAC GGA GTG AAA CTC GAC<br>Lys Ala Ile Cys Asn Phe Tyr Glu Glu Arg Tyr Gly Val Lys Leu Asp<br>　　　　　　　　　85　　　　　　　　　　90　　　　　　　　　　95 | 288 |
| CCT GAG AGG GAG GCT ATA CTA ACA ATC GGT GCA AAG GAA GGG TAT TCT<br>Pro Glu Arg Glu Ala Ile Leu Thr Ile Gly Ala Lys Glu Gly Tyr Ser<br>　　　　　　　　100　　　　　　　　　　105　　　　　　　　　110 | 336 |
| CAT TTG ATG CTT GCG ATG ATA TCT CCG GGT GAT ACG GTA ATA GTT CCT<br>His Leu Met Leu Ala Met Ile Ser Pro Gly Asp Thr Val Ile Val Pro<br>　　　　　115　　　　　　　　　　120　　　　　　　　　　125 | 384 |
| AAT CCC ACC TAT CCT ATT CAC TAT TAC GCT CCC ATA ATT GCA GGA GGG<br>Asn Pro Thr Tyr Pro Ile His Tyr Tyr Ala Pro Ile Ile Ala Gly Gly<br>　　130　　　　　　　　　　135　　　　　　　　　　140 | 432 |
| GAA GTT CAC TCA ATA CCC CTT AAC TTC TCG GAC GAT CAA GAT CAT CAG<br>Glu Val His Ser Ile Pro Leu Asn Phe Ser Asp Asp Gln Asp His Gln<br>145　　　　　　　　　　150　　　　　　　　　　155　　　　　　　　　　160 | 480 |
| GAA GAG TTT TTA AGG AGG CTT TAC GAG ATA GTA AAA ACC GCG ATG CCA<br>Glu Glu Phe Leu Arg Arg Leu Tyr Glu Ile Val Lys Thr Ala Met Pro<br>　　　　　　　　　165　　　　　　　　　　170　　　　　　　　　175 | 528 |
| AAA CCC AAG GCT GTC GTC ATA AGC TTT CCT CAC AAT CCA ACG ACC ATA<br>Lys Pro Lys Ala Val Val Ile Ser Phe Pro His Asn Pro Thr Thr Ile<br>　　　　　　　180　　　　　　　　　　185　　　　　　　　　　190 | 576 |
| ACG GTA GAA AAG GAC TTT TTT AAA GAA ATA GTT AAG TTT GCA AAG GAA<br>Thr Val Glu Lys Asp Phe Phe Lys Glu Ile Val Lys Phe Ala Lys Glu<br>　　　　　195　　　　　　　　　　200　　　　　　　　　　205 | 624 |
| CAC GGT CTC TGG ATA ATA CAC GAT TTT GCG TAT GCG GAT ATA GCC TTT<br>His Gly Leu Trp Ile Ile His Asp Phe Ala Tyr Ala Asp Ile Ala Phe<br>　　210　　　　　　　　　　215　　　　　　　　　　220 | 672 |
| GAC GGT TAC AAG CCC CCC TCA ATA CTC GAA ATA GAA GGT GCT AAA GAC<br>Asp Gly Tyr Lys Pro Pro Ser Ile Leu Glu Ile Glu Gly Ala Lys Asp<br>225　　　　　　　　　　230　　　　　　　　　　235　　　　　　　　　　240 | 720 |

FIG. 1A

```
GTT GCG GTT GAG CTC TAC TCC ATG TCA AAG GGC TTT TCA ATG GCG GGC        768
Val Ala Val Glu Leu Tyr Ser Met Ser Lys Gly Phe Ser Met Ala Gly
            245                 250                 255

TGG AGG GTA GCC TTT GTC GTT GGA AAC GAA ATA CTC ATA AAA AAC CTT        816
Trp Arg Val Ala Phe Val Val Gly Asn Glu Ile Leu Ile Lys Asn Leu
            260                 265                 270

GCA CAC CTC AAA AGC TAC TTG GAT TAC GGT ATA TTT ACT CCC ATA CAG        864
Ala His Leu Lys Ser Tyr Leu Asp Tyr Gly Ile Phe Thr Pro Ile Gln
            275                 280                 285

GTG GCC TCT ATT ATC GCA TTA GAG AGC CCC TAC GAA ATC GTG GAA AAA        912
Val Ala Ser Ile Ile Ala Leu Glu Ser Pro Tyr Glu Ile Val Glu Lys
        290                 295                 300

ACC GCA AAG GTT TAC CAA AAA AGA AGA GAC GTT CTG GTG GAA GGG TTA        960
Thr Ala Lys Val Tyr Gln Lys Arg Arg Asp Val Leu Val Glu Gly Leu
305                 310                 315                 320

AAC AGG CTC GGC TGG AAA GTA AAA AAA CCT AAG GCT ACC ATG TTC GTC       1008
Asn Arg Leu Gly Trp Lys Val Lys Lys Pro Lys Ala Thr Met Phe Val
            325                 330                 335

TGG GCA AAG ATT CCC GAA TGG ATA AAT ATG AAC TCT CTG GAC TTT TCC       1056
Trp Ala Lys Ile Pro Glu Trp Ile Asn Met Asn Ser Leu Asp Phe Ser
            340                 345                 350

TTG TTC CTC CTA AAA GAG GCG AAG GTT GCG GTA TCC CCG GGT GTG GGC       1104
Leu Phe Leu Leu Lys Glu Ala Lys Val Ala Val Ser Pro Gly Val Gly
            355                 360                 365

TTT GGT CAG TAC GGA GAG GGG TAC GTA AGG TTT GCA CTT GTA GAA AAT       1152
Phe Gly Gln Tyr Gly Glu Gly Tyr Val Arg Phe Ala Leu Val Glu Asn
            370                 375                 380

GAA CAC AGG ATC AGA CAG GCT ATA AGG GGA ATA AGG AAA GCC TTC AGA       1200
Glu His Arg Ile Arg Gln Ala Ile Arg Gly Ile Arg Lys Ala Phe Arg
385                 390                 395                 400

AAA CTC CAG AAG GAG AGG AAA CTT GAA CCT GAG AGA AGT GCT TAA           1245
Lys Leu Gln Lys Glu Arg Lys Leu Glu Pro Glu Arg Ser Ala End
            405                 410                 414
```

FIG. 1B

```
ATG GAC AGG CTT GAA AAA GTA TCA CCC TTC ATA GTA ATG GAT ATC CTA        48
Met Asp Arg Leu Glu Lys Val Ser Pro Phe Ile Val Met Asp Ile Leu
              5                   10                  15

GCT CAG GCC CAG AAG TAC GAA GAC GTA GTA CAC ATG GAG ATA GGA GAG        96
Ala Gln Ala Gln Lys Tyr Glu Asp Val Val His Met Glu Ile Gly Glu
             20                  25                  30

CCC GAT TTA GAA CCG TCT CCC AAG GTA ATG GAA GCT CTG GAA CGT GCG       144
Pro Asp Leu Glu Pro Ser Pro Lys Val Met Glu Ala Leu Glu Arg Ala
         35                  40                  45

GTG AAG GAA AAG ACG TTC TTC TAC ACC CCT GCT CTG GGA CTC TGG GAA       192
Val Lys Glu Lys Thr Phe Phe Tyr Thr Pro Ala Leu Gly Leu Trp Glu
     50                  55                  60

CTC AGG GAA AGG ATA TCG GAG TTT TAC AGG AAA AAG TAC AGC GTT GAA       240
Leu Arg Glu Arg Ile Ser Glu Phe Tyr Arg Lys Lys Tyr Ser Val Glu
 65                  70                  75                  80

GTT TCT CCA GAG AGA GTC ATC GTA ACT ACC GGA ACT TCG GGA GCG TTT       288
Val Ser Pro Glu Arg Val Ile Val Thr Thr Gly Thr Ser Gly Ala Phe
                 85                  90                  95

CTC GTA GCC TAC GCC GTA ACA CTA AAT GCG GGA GAG AAG ATA ATC CTC       336
Leu Val Ala Tyr Ala Val Thr Leu Asn Ala Gly Glu Lys Ile Ile Leu
             100                 105                 110

CCA GAC CCC TCT TAC CCC TGT TAC AAA AAC TTT GCC TAC CTC TTA GAC       384
Pro Asp Pro Ser Tyr Pro Cys Tyr Lys Asn Phe Ala Tyr Leu Leu Asp
         115                 120                 125

GCT CAG CCG GTT TTC GTA AAC GTT GAC AAG GAA ACG AAT TAC GAA GTA       432
Ala Gln Pro Val Phe Val Asn Val Asp Lys Glu Thr Asn Tyr Glu Val
     130                 135                 140

AGG AAA GAG ATG ATA GAA GAC ATT GAT GCG AAA GCC CTT CAC ATT TCC       480
Arg Lys Glu Met Ile Glu Asp Ile Asp Ala Lys Ala Leu His Ile Ser
145                 150                 155                 160

TCG CCT CAA AAC CCT ACG GGC ACA CTC TAC TCA CCT GAA ACC CTG AAG       528
Ser Pro Gln Asn Pro Thr Gly Thr Leu Tyr Ser Pro Glu Thr Leu Lys
                 165                 170                 175

GAA CTT GCG GAG TAC TGC GAA GAG AAG GGT ATG TAC TTC ATA TCC GAC       576
Glu Leu Ala Glu Tyr Cys Glu Glu Lys Gly Met Tyr Phe Ile Ser Asp
             180                 185                 190

GAG ATT TAC CAC GGA CTC GTT TAC GAA GGT AGG GAG CAC ACA GCA CTT       624
Glu Ile Tyr His Gly Leu Val Tyr Glu Gly Arg Glu His Thr Ala Leu
         195                 200                 205

GAG TTC TCT GAC AGG GCT ATT GTC ATA AAC GGG TTT TCT AAG TAC TTC       672
Glu Phe Ser Asp Arg Ala Ile Val Ile Asn Gly Phe Ser Lys Tyr Phe
     210                 215                 220

TGT ATG CCA GGT TTC AGG ATA GGG TGG ATG ATA GTT CCG GAA GAA CTC       720
Cys Met Pro Gly Phe Arg Ile Gly Trp Met Ile Val Pro Glu Glu Leu
225                 230                 235                 240
```

FIG. 2A

```
GTG AGA AAG GCG GAA ATA GTA ATT CAG AAC GTA TTT ATA TCT GCC CCG           768
Val Arg Lys Ala Glu Ile Val Ile Gln Asn Val Phe Ile Ser Ala Pro
            245                 250                 255

ACG CTC AGT CAG TAC GCC GCC CTT GAG GCT TTT GAT TAC GAG TAT TTG           816
Thr Leu Ser Gln Tyr Ala Ala Leu Glu Ala Phe Asp Tyr Glu Tyr Leu
            260                 265                 270

GAG AAG GTA AGA AAA ACC TTT GAA GAG AGG AGG AAC TTC CTT TAT GGG           864
Glu Lys Val Arg Lys Thr Phe Glu Glu Arg Arg Asn Phe Leu Tyr Gly
            275                 280                 285

GAA CTG AAA AAA CTC TTC AAG ATA GAC GCG AAA CCT CAG GGA GCT TTT           912
Glu Leu Lys Lys Leu Phe Lys Ile Asp Ala Lys Pro Gln Gly Ala Phe
            290                 295                 300

TAC GTA TGG GCA AAC ATA AGT GAT TAC TCC ACA GAT AGC TAC GAA TTT           960
Tyr Val Trp Ala Asn Ile Ser Asp Tyr Ser Thr Asp Ser Tyr Glu Phe
305                 310                 315                 320

GCT TTA AAA CTT TTA AGG GAG GCG AGG GTG GCG GTA ACG CCC GGG GTG          1008
Ala Leu Lys Leu Leu Arg Glu Ala Arg Val Ala Val Thr Pro Gly Val
            325                 330                 335

GAC TTT GGA AAA AAC AAA ACG AAG GAG TAT ATA AGG TTT GCT TAT ACG          1056
Asp Phe Gly Lys Asn Lys Thr Lys Glu Tyr Ile Arg Phe Ala Tyr Thr
            340                 345                 350

AGA AAG ATA GAA GAA CTT AAG GAG GGC GTT GAA AGG ATA AAG AAG TTC          1104
Arg Lys Ile Glu Glu Leu Lys Glu Gly Val Glu Arg Ile Lys Lys Phe
            355                 360                 365

TTA GAG AAG CTT AGC TGA                                                  1122
Leu Glu Lys Leu Ser End
            370
```

FIG. 2B

| | | | | | | | | | | | | | | | | |
|---|---|---|---|---|---|---|---|---|---|---|---|---|---|---|---|---|
| ATG | TGG | GAA | TTA | GAC | CCT | AAA | ACG | CTC | GAA | AAG | TGG | GAC | AAG | GAG | TAC | 48 |
| Met | Trp | Glu | Leu | Asp | Pro | Lys | Thr | Leu | Glu | Lys | Trp | Asp | Lys | Glu | Tyr | |
| | | | | 5 | | | | 10 | | | | | 15 | | | |
| TTC | TGG | CAT | CCA | TTT | ACC | CAG | ATG | AAA | GTC | TAC | AGA | GAA | GAA | GAA | AAC | 96 |
| Phe | Trp | His | Pro | Phe | Thr | Gln | Met | Lys | Val | Tyr | Arg | Glu | Glu | Glu | Asn | |
| | | | 20 | | | | | 25 | | | | | 30 | | | |
| CTG | ATA | TTT | GAA | CGC | GGA | GAA | GGC | GTT | TAC | CTG | TGG | GAC | ATA | TAC | GGC | 144 |
| Leu | Ile | Phe | Glu | Arg | Gly | Glu | Gly | Val | Tyr | Leu | Trp | Asp | Ile | Tyr | Gly | |
| | | 35 | | | | | 40 | | | | | 45 | | | | |
| AGG | AAG | TAT | ATA | GAT | GCC | ATA | TCT | TCC | CTC | TGG | TGC | AAC | GTC | CAC | GGA | 192 |
| Arg | Lys | Tyr | Ile | Asp | Ala | Ile | Ser | Ser | Leu | Trp | Cys | Asn | Val | His | Gly | |
| | 50 | | | | | 55 | | | | | 60 | | | | | |
| CAT | AAC | CAC | CCT | AAA | CTG | AAC | AAC | GCA | GTT | ATG | AAA | CAG | CTC | TGT | AAG | 240 |
| His | Asn | His | Pro | Lys | Leu | Asn | Asn | Ala | Val | Met | Lys | Gln | Leu | Cys | Lys | |
| 65 | | | | | 70 | | | | | 75 | | | | | 80 | |
| GTA | GCT | CAC | ACA | ACT | ACT | CTG | GGA | AGT | TCC | AAC | GTT | CCC | GCC | ATA | CTC | 288 |
| Val | Ala | His | Thr | Thr | Thr | Leu | Gly | Ser | Ser | Asn | Val | Pro | Ala | Ile | Leu | |
| | | | | 85 | | | | | 90 | | | | | 95 | | |
| CTT | GCA | AAG | AAG | CTT | GTA | GAA | ATT | TCT | CCT | GAA | GGA | TTA | AAC | AAG | GTC | 336 |
| Leu | Ala | Lys | Lys | Leu | Val | Glu | Ile | Ser | Pro | Glu | Gly | Leu | Asn | Lys | Val | |
| | | | 100 | | | | | 105 | | | | | 110 | | | |
| TTT | TAC | TCC | GAA | GAC | GGT | GCG | GAA | GCA | GTA | GAG | ATA | GCG | ATA | AAG | ATG | 384 |
| Phe | Tyr | Ser | Glu | Asp | Gly | Ala | Glu | Ala | Val | Glu | Ile | Ala | Ile | Lys | Met | |
| | | 115 | | | | | 120 | | | | | 125 | | | | |
| GCT | TAT | CAC | TAC | TGG | AAG | AAC | AAG | GGA | GTT | AAA | GGG | AAA | AAC | GTT | TTC | 432 |
| Ala | Tyr | His | Tyr | Trp | Lys | Asn | Lys | Gly | Val | Lys | Gly | Lys | Asn | Val | Phe | |
| | 130 | | | | | 135 | | | | | 140 | | | | | |
| ATA | ACG | CTT | TCC | GAA | GCC | TAC | CAC | GGG | GAT | ACT | GTA | GGA | GCG | GTT | AGC | 480 |
| Ile | Thr | Leu | Ser | Glu | Ala | Tyr | His | Gly | Asp | Thr | Val | Gly | Ala | Val | Ser | |
| 145 | | | | | 150 | | | | | 155 | | | | | 160 | |
| GTA | GGG | GGT | ATA | GAA | CTC | TTC | CAC | GGA | ACT | TAT | AAA | GAT | CTC | CTT | TTC | 528 |
| Val | Gly | Gly | Ile | Glu | Leu | Phe | His | Gly | Thr | Tyr | Lys | Asp | Leu | Leu | Phe | |
| | | | | 165 | | | | | 170 | | | | | 175 | | |
| AAG | ACT | ATA | AAA | CTC | CCA | TCT | CCT | TAC | CTG | TAC | TGC | AAG | GAA | AAG | TAC | 576 |
| Lys | Thr | Ile | Lys | Leu | Pro | Ser | Pro | Tyr | Leu | Tyr | Cys | Lys | Glu | Lys | Tyr | |
| | | | 180 | | | | | 185 | | | | | 190 | | | |
| GGG | GAA | CTC | TGC | CCT | GAG | TGC | ACG | GCA | GAT | TTA | TTA | AAA | CAA | CTG | GAA | 624 |
| Gly | Glu | Leu | Cys | Pro | Glu | Cys | Thr | Ala | Asp | Leu | Leu | Lys | Gln | Leu | Glu | |
| | | 195 | | | | | 200 | | | | | 205 | | | | |
| GAT | ATC | CTG | AAG | TCG | CGG | GAA | GAT | ATC | GTT | GCG | GTC | ATT | ATG | GAA | GCG | 672 |
| Asp | Ile | Leu | Lys | Ser | Arg | Glu | Asp | Ile | Val | Ala | Val | Ile | Met | Glu | Ala | |
| | 210 | | | | | 215 | | | | | 220 | | | | | |
| GGA | ATT | CAG | GCA | GCC | GCG | GGA | ATG | CTC | CCC | TTC | CCT | CCG | GGA | TTT | TTG | 720 |
| Gly | Ile | Gln | Ala | Ala | Ala | Gly | Met | Leu | Pro | Phe | Pro | Pro | Gly | Phe | Leu | |
| 225 | | | | | 230 | | | | | 235 | | | | | 240 | |

FIG. 3A

| | |
|---|---|
| AAA GGC GTA AGG GAG CTT ACG AAG AAA TAC GAC ACT TTA ATG ATA GTT<br>Lys Gly Val Arg Glu Leu Thr Lys Lys Tyr Asp Thr Leu Met Ile Val<br>              245                      250                  255 | 768 |
| GAC GAG GTT GCC ACG GGA TTT GGC AGG ACG GGA ACG ATG TTT TAC TGT<br>Asp Glu Val Ala Thr Gly Phe Gly Arg Thr Gly Thr Met Phe Tyr Cys<br>            260                      265                  270 | 816 |
| GAG CAG GAA GGA GTC AGT CCG GAC TTT ATG TGT CTA GGT AAG GGT ATA<br>Glu Gln Glu Gly Val Ser Pro Asp Phe Met Cys Leu Gly Lys Gly Ile<br>       275                      280                  285 | 864 |
| ACC GGA GGG TAC CTC CCG CTT GCT GCG ACA CTC ACA ACG GAC GAG GTG<br>Thr Gly Gly Tyr Leu Pro Leu Ala Ala Thr Leu Thr Thr Asp Glu Val<br>    290                      295                  300 | 912 |
| TTC AAT GCC TTT TTA GGT GAG TTC GGG GAG GCA AAG CAC TTT TAC CAC<br>Phe Asn Ala Phe Leu Gly Glu Phe Gly Glu Ala Lys His Phe Tyr His<br>305                   310                  315                  320 | 960 |
| GGG CAC ACC TAC ACT GGA AAT AAC CTC GCC TGT TCC GTT GCA CTC GCA<br>Gly His Thr Tyr Thr Gly Asn Asn Leu Ala Cys Ser Val Ala Leu Ala<br>            325                      330                  335 | 1008 |
| AAC TTA GAA GTT TTT GAG GAA GAA AGA ACT TTA GAG AAG CTC CAA CCA<br>Asn Leu Glu Val Phe Glu Glu Glu Arg Thr Leu Glu Lys Leu Gln Pro<br>              340                      345                  350 | 1056 |
| AAG ATA AAG CTT TTA AAG GAA AGG CTT CAG GAG TTC TGG GAA CTC AAG<br>Lys Ile Lys Leu Leu Lys Glu Arg Leu Gln Glu Phe Trp Glu Leu Lys<br>       355                      360                  365 | 1104 |
| CAC GTT GGA GAT GTT AGA CAG CTA GGT TTT ATG GCT GGA ATA GAG CTG<br>His Val Gly Asp Val Arg Gln Leu Gly Phe Met Ala Gly Ile Glu Leu<br>    370                      375                  380 | 1152 |
| GTG AAG GAC AAA GAA AAG GGA GAA CCT TTC CCT TAC GGT GAA AGG ACG<br>Val Lys Asp Lys Glu Lys Gly Glu Pro Phe Pro Tyr Gly Glu Arg Thr<br>385                   390                  395                  400 | 1200 |
| GGA TTT AAG GTG GCT TAC AAG TGC AGG GAA AAA GGG GTG TTT TTG AGA<br>Gly Phe Lys Val Ala Tyr Lys Cys Arg Glu Lys Gly Val Phe Leu Arg<br>            405                      410                  415 | 1245 |
| CCG CTC GGA GAC GTT ATG GTA TTG ATG ATG CCT CTT GTA ATA GAG GAA<br>Pro Leu Gly Asp Val Met Val Leu Met Met Pro Leu Val Ile Glu Glu<br>              420                      425                  430 | 1293 |
| GAC GAA ATG AAC TAC GTT ATT GAT ACA CTT AAA TGG GCA ATT AAA GAG<br>Asp Glu Met Asn Tyr Val Ile Asp Thr Leu Lys Trp Ala Ile Lys Glu<br>       435                      440                  445 | 1341 |
| CTT GAA AAA GAG GTG TAG<br>Leu Glu Lys Glu Val End<br>    450 | 1359 |

FIG. 3B

| | | |
|---|---|---|
| ATG ACA TAC TTA ATG AAC AAT TAC GCA AGG TTG CCC GTA AAG TTT GTA | 48 |
| Met Thr Tyr Leu Met Asn Asn Tyr Ala Arg Leu Pro Val Lys Phe Val | |
| 5 10 15 | |
| AGG GGA AAA GGT GTT TAC CTG TAC GAT GAG GAA GGA AAG GAG TAT CTT | 96 |
| Arg Gly Lys Gly Val Tyr Leu Tyr Asp Glu Glu Gly Lys Glu Tyr Leu | |
| 20 25 30 | |
| GAC TTT GTC TCC GGT ATA GGC GTC AAC TCC CTC GGT CAC GCT TAC CCA | 144 |
| Asp Phe Val Ser Gly Ile Gly Val Asn Ser Leu Gly His Ala Tyr Pro | |
| 35 40 45 | |
| AAA CTC ACA GAA GCT CTA AAA GAA CAG GTT GAG AAA CTC CTC CAC GTT | 192 |
| Lys Leu Thr Glu Ala Leu Lys Glu Gln Val Glu Lys Leu Leu His Val | |
| 50 55 60 | |
| TCA AAT CTT TAC GAA AAC CCG TGG CAG GAA GAA CTG GCT CAC AAA CTT | 240 |
| Ser Asn Leu Tyr Glu Asn Pro Trp Gln Glu Glu Leu Ala His Lys Leu | |
| 65 70 75 80 | |
| GTA AAA CAC TTC TGG ACA GAA GGG AAG GTA TTT TTC GCA AAC AGC GGA | 288 |
| Val Lys His Phe Trp Thr Glu Gly Lys Val Phe Phe Ala Asn Ser Gly | |
| 85 90 95 | |
| ACG GAA AGT GTA GAG GCG GCT ATA AAG CTC GCA AGG AAG TAC TGG AGG | 336 |
| Thr Glu Ser Val Glu Ala Ala Ile Lys Leu Ala Arg Lys Tyr Trp Arg | |
| 100 105 110 | |
| GAT AAA GGA AAG AAC AAG TGG AAG TTT ATA TCC TTT GAA AAC TCT TTC | 384 |
| Asp Lys Gly Lys Asn Lys Trp Lys Phe Ile Ser Phe Glu Asn Ser Phe | |
| 115 120 125 | |
| CAC GGG AGA ACC TAC GGT AGC CTC TCC GCA ACG GGA CAG CCA AAG TTC | 432 |
| His Gly Arg Thr Tyr Gly Ser Leu Ser Ala Thr Gly Gln Pro Lys Phe | |
| 130 135 140 | |
| CAC AAA GGC TTT GAA CCT CTA GTT CCT GGA TTT TCT TAC GCA AAG CTG | 480 |
| His Lys Gly Phe Glu Pro Leu Val Pro Gly Phe Ser Tyr Ala Lys Leu | |
| 145 150 155 160 | |
| AAC GAT ATA GAC AGC GTT TAC AAA CTC CTA GAC GAG GAA ACC GCG GGG | 528 |
| Asn Asp Ile Asp Ser Val Tyr Lys Leu Leu Asp Glu Glu Thr Ala Gly | |
| 165 170 175 | |
| ATA ATT ATT GAA GTT ATA CAA GGA GAG GGC GGA GTA AAC GAG GCG AGT | 576 |
| Ile Ile Ile Glu Val Ile Gln Gly Glu Gly Gly Val Asn Glu Ala Ser | |
| 180 185 190 | |
| GAG GAT TTT CTA AGT AAA CTC CAG GAA ATT TGT AAA GAA AAA GAT GTG | 624 |
| Glu Asp Phe Leu Ser Lys Leu Gln Glu Ile Cys Lys Glu Lys Asp Val | |
| 195 200 205 | |
| CTC TTA ATT ATA GAC GAA GTG CAA ACG GGA ATA GGA AGG ACC GGG GAA | 672 |
| Leu Leu Ile Ile Asp Glu Val Gln Thr Gly Ile Gly Arg Thr Gly Glu | |
| 210 215 220 | |
| TTC TAC GCA TAT CAA CAC TTC AAT CTA AAA CCG GAC GTA ATT GCG CTT | 720 |
| Phe Tyr Ala Tyr Gln His Phe Asn Leu Lys Pro Asp Val Ile Ala Leu | |
| 225 230 235 240 | |

FIG. 4A

```
GCG AAG GGA CTC GGA GGA GGT GTG CCA ATA GGT GCC ATC CTT GCA AGG         768
Ala Lys Gly Leu Gly Gly Gly Val Pro Ile Gly Ala Ile Leu Ala Arg
            245                 250                 255

GAA GAA GTG GCC CAG AGC TTT ACT CCC GGC TCC CAC GGC TCT ACC TTC         816
Glu Glu Val Ala Gln Ser Phe Thr Pro Gly Ser His Gly Ser Thr Phe
            260                 265                 270

GGA GGA AAC CCC TTA GCC TGC AGG GCG GGA ACA GTG GTA GTA GAT GAA         864
Gly Gly Asn Pro Leu Ala Cys Arg Ala Gly Thr Val Val Val Asp Glu
            275                 280                 285

GTT GAA AAA CTC CTG CCT CAC GTA AGG GAA GTG GGG AAT TAC TTC AAA         912
Val Glu Lys Leu Leu Pro His Val Arg Glu Val Gly Asn Tyr Phe Lys
            290                 295                 300

GAA AAA CTG AAG GAA CTC GGC AAA GGA AAG GTA AAG GGA AGA GGA TTG         960
Glu Lys Leu Lys Glu Leu Gly Lys Gly Lys Val Lys Gly Arg Gly Leu
305                 310                 315                 320

ATG CTC GGT CTT GAA CTT GAA AGA GAG TGT AAA GAT TAC GTT CTC AAG        1008
Met Leu Gly Leu Glu Leu Glu Arg Glu Cys Lys Asp Tyr Val Leu Lys
                    325                 330                 335

GCT CTT GAA AGG GAC TTC TCA TAA                                        1032
Ala Leu Glu Arg Asp Phe Ser End
            340
```

FIG. 4B

```
ATG CGG AAA CTG GCC GAG CGG GCG CAG AAA CTG AGC CCC TCT CCC ACC      48
Met Arg Lys Leu Ala Glu Arg Ala Gln Lys Leu Ser Pro Ser Pro Thr
             5                  10                  15

CTC TCG GTG GAC ACC AAG GCC AAG GAG CTT TTG CGG CAG GGG GAA AGG      96
Leu Ser Val Asp Thr Lys Ala Lys Glu Leu Leu Arg Gln Gly Glu Arg
             20                  25                  30

GTC ATC AAT TTC GGG GCG GGG GAG CCG GAC TTC GAT ACA CCG GAA CAC     144
Val Ile Asn Phe Gly Ala Gly Glu Pro Asp Phe Asp Thr Pro Glu His
             35                  40                  45

ATC AAG GAA GCG GCG AAG CGA GCT TTA GAT CAG GGC TTC ACC AAG TAC     192
Ile Lys Glu Ala Ala Lys Arg Ala Leu Asp Gln Gly Phe Thr Lys Tyr
             50                  55                  60

ACG CCG GTG GCT GGG ATC TTA CCT CTT CGG GAG GCC ATA TGC GAG AAG     240
Thr Pro Val Ala Gly Ile Leu Pro Leu Arg Glu Ala Ile Cys Glu Lys
 65              70                  75                  80

CTT TAC CGC GAC AAT CAA CTG GAA TAC AGC CCG AAT GAG ATC GTG GTC     288
Leu Tyr Arg Asp Asn Gln Leu Glu Tyr Ser Pro Asn Glu Ile Val Val
             85                  90                  95

TCC TGT GGC GCC AAG CAT TCT ATT TTC AAC GCT CTG CAG GTC CTC CTG     336
Ser Cys Gly Ala Lys His Ser Ile Phe Asn Ala Leu Gln Val Leu Leu
             100                 105                 110

GAC CCG GGG GAC GAG GTG ATA ATC CCC GTC CCC TAC TGG ACT TCC TAT     384
Asp Pro Gly Asp Glu Val Ile Ile Pro Val Pro Tyr Trp Thr Ser Tyr
             115                 120                 125

CCG GAG CAG GTG AAG CTG GCG GGA GGG GTG CCG GTT TTC GTC CCC ACC     432
Pro Glu Gln Val Lys Leu Ala Gly Gly Val Pro Val Phe Val Pro Thr
 130                 135                 140

TCT CCC GAG AAC GAC TTC AAG CTC AGG CCG GAA GAT CTA CGT GCG GCT     480
Ser Pro Glu Asn Asp Phe Lys Leu Arg Pro Glu Asp Leu Arg Ala Ala
145                 150                 155                 160

GTA ACC CCG CGC ACC CGC CTT TTG ATC CTC AAT TCC CCG GCC AAC CCC     528
Val Thr Pro Arg Thr Arg Leu Leu Ile Leu Asn Ser Pro Ala Asn Pro
             165                 170                 175

ACA GGC ACC GTT TAC CGC GGG GAG GAA CTT ATC GGC TTA GCG GAG GTA     576
Thr Gly Thr Val Tyr Arg Arg Glu Glu Leu Ile Gly Leu Ala Glu Val
             180                 185                 190

GCC CTG GAG GCC GAC CTA TGG ATC TTG TCG GAC GAG ATC TAC GAA AAG     624
Ala Leu Glu Ala Asp Leu Trp Ile Leu Ser Asp Glu Ile Tyr Glu Lys
             195                 200                 205

CTG ATC TAC GAC GGG ATG GAG CAC GTG AGC ATA GCC GCG CTC GAC CCG     672
Leu Ile Tyr Asp Gly Met Glu His Val Ser Ile Ala Ala Leu Asp Pro
             210                 215                 220

GAG GTC AAA AAG CGC ACG ATT GTG GTA AAC GGT GTT TCC AAG GCT TAC     720
Glu Val Lys Lys Arg Thr Ile Val Val Asn Gly Val Ser Lys Ala Tyr
225                 230                 235                 240
```

FIG. 5A

| | |
|---|---|
| GCC ATG ACC GGT TGG CGC ATA GGT TAT GCT GCC GCT CCC CGG CCG ATA<br>Ala Met Thr Gly Trp Arg Ile Gly Tyr Ala Ala Ala Pro Arg Pro Ile<br>            245                   250                 255 | 768 |
| GCC CAG GCC ATG ACC AAC CTC CAA AGC CAC AGT ACC TCT AAC CCC ACT<br>Ala Gln Ala Met Thr Asn Leu Gln Ser His Ser Thr Ser Asn Pro Thr<br>            260                   265                 270 | 816 |
| TCC GTA GCC CAG GCG GCG GCG CTG GCC GCT CTG AAG GGG CCA CAA GAG<br>Ser Val Ala Gln Ala Ala Ala Leu Ala Ala Leu Lys Gly Pro Gln Glu<br>    275                   280                 285 | 864 |
| CCG GTG GAG AAC ATG CGC CGG GCT TTT CAA AAG CGG CGG GAT TTC ATC<br>Pro Val Glu Asn Met Arg Arg Ala Phe Gln Lys Arg Arg Asp Phe Ile<br>    290                   295                 300 | 912 |
| TGG CAG TAC CTA AAC TCC TTA CCC GGA GTG CGC TGC CCC AAA CCT TTA<br>Trp Gln Tyr Leu Asn Ser Leu Pro Gly Val Arg Cys Pro Lys Pro Leu<br>305                   310                 315                 320 | 960 |
| GGG GCC TTT TAC GTC TTT CCA GAA GTT GAG CGG GCT TTT GGG CCG CCG<br>Gly Ala Phe Tyr Val Phe Pro Glu Val Glu Arg Ala Phe Gly Pro Pro<br>                 325                 330                 335 | 1008 |
| TCT AAA AGG ACG GGA AAT ACT ACC GCT AGC GAC CTG GCC CTT TTC CTC<br>Ser Lys Arg Thr Gly Asn Thr Thr Ala Ser Asp Leu Ala Leu Phe Leu<br>         340                   345                 350 | 1056 |
| CTG GAA GAG ATA AAA GTG GCC ACC GTG GCT GGG GCT GCC TTT GGG GAC<br>Leu Glu Glu Ile Lys Val Ala Thr Val Ala Gly Ala Ala Phe Gly Asp<br>            355                   360                 365 | 1104 |
| GAT CGC TAC CTG CGC TTT TCC TAC GCC CTG CGG CTG GAA GAT ATC GAA<br>Asp Arg Tyr Leu Arg Phe Ser Tyr Ala Leu Arg Leu Glu Asp Ile Glu<br>    370                   375                 380 | 1152 |
| GAG GGG ATG CAA CGG TTT AAA GAA TTG ATC GAA GCG GCA CTT TAA<br>Glu Gly Met Gln Arg Phe Lys Glu Leu Ile Glu Ala Ala Leu End<br>385                   390                 395 | 1197 |

FIG. 5B

| | | |
|---|---|---|
| ATG TGC GGG ATA GTC GGA TAC GTA GGG AGG GAT TTA GCC CTT CCT ATA<br>Met Cys Gly Ile Val Gly Tyr Val Gly Arg Asp Leu Ala Leu Pro Ile<br>　　　　　　5　　　　　　　　　　10　　　　　　　　　　15 | | 48 |
| GTC CTC GGA GCT CTT GAG AGA CTC GAA TAC AGG GGT TAC GAC TCC GCG<br>Val Leu Gly Ala Leu Glu Arg Leu Glu Tyr Arg Gly Tyr Asp Ser Ala<br>　　　　20　　　　　　　　　　25　　　　　　　　　　30 | | 96 |
| GGA GTT GCC CTT ATA GAA GAC GGG AAA CTC ATA GTT GAA AAG AAG AAG<br>Gly Val Ala Leu Ile Glu Asp Gly Lys Leu Ile Val Glu Lys Lys Lys<br>　　　　35　　　　　　　　　　40　　　　　　　　　　45 | | 144 |
| GGA AAG ATA AGG GAA CTC GTT AAA GCG CTA TGG GGA AAG GAT TAC AAG<br>Gly Lys Ile Arg Glu Leu Val Lys Ala Leu Trp Gly Lys Asp Tyr Lys<br>50　　　　　　　　　　55　　　　　　　　　　60 | | 192 |
| GCT AAA ACG GGT ATA GGT CAC ACA CGC TGG GCA ACC CAC GGA AAG CCC<br>Ala Lys Thr Gly Ile Gly His Thr Arg Trp Ala Thr His Gly Lys Pro<br>65　　　　　　　　　　70　　　　　　　　　　75　　　　　　　　　　80 | | 240 |
| ACG GAC GAG AAC GCC CAC CCC CAC ACC GAC GAA AAA GGT GAG TTT GCA<br>Thr Asp Glu Asn Ala His Pro His Thr Asp Glu Lys Gly Glu Phe Ala<br>　　　　　　　　　85　　　　　　　　　　90　　　　　　　　　　95 | | 288 |
| GTA GTT CAC AAC GGG ATA ATA GAA AAC TAC TTA GAA CTA AAA GAG GAA<br>Val Val His Asn Gly Ile Ile Glu Asn Tyr Leu Glu Leu Lys Glu Glu<br>　　　　　　　　100　　　　　　　　　105　　　　　　　　　110 | | 336 |
| CTA AAG AAG GAA GGT GTA AAG TTC AGG TCC GAA ACA GAC ACA GAA GTT<br>Leu Lys Lys Glu Gly Val Lys Phe Arg Ser Glu Thr Asp Thr Glu Val<br>　　　　115　　　　　　　　　120　　　　　　　　　125 | | 384 |
| ATA GCC CAC CTC ATA GCG AAG AAC TAC AGG GGG GAC TTA CTG GAG GCC<br>Ile Ala His Leu Ile Ala Lys Asn Tyr Arg Gly Asp Leu Leu Glu Ala<br>130　　　　　　　　　135　　　　　　　　　140 | | 432 |
| GTT TTA AAA ACC GTA AAG AAA TTA AAG GGT GCT TTT GCC TTT GCG GTT<br>Val Leu Lys Thr Val Lys Lys Leu Lys Gly Ala Phe Ala Phe Ala Val<br>145　　　　　　　　　150　　　　　　　　　155　　　　　　　　　160 | | 480 |
| ATA ACG GTT CAC GAA CCA AAC AGA CTA ATA GGA GTG AAG CAG GGG AGT<br>Ile Thr Val His Glu Pro Asn Arg Leu Ile Gly Val Lys Gln Gly Ser<br>　　　　　　　　165　　　　　　　　　170　　　　　　　　　175 | | 528 |
| CCT TTA ATC GTC GGA CTC GGA GAA GGA GAA AAC TTC CTC GCT TCA GAT<br>Pro Leu Ile Val Gly Leu Gly Glu Gly Glu Asn Phe Leu Ala Ser Asp<br>　　　　　　　　180　　　　　　　　　185　　　　　　　　　190 | | 576 |
| ATT CCC GCA ATA CTT CCT TAC ACG AAA AAG ATT ATT GTT CTT GAT GAC<br>Ile Pro Ala Ile Leu Pro Tyr Thr Lys Lys Ile Ile Val Leu Asp Asp<br>　　　　195　　　　　　　　　200　　　　　　　　　205 | | 624 |
| GGG GAA ATA GCG GAC CTG ACT CCC GAC ACT GTG AAC ATT TAC AAC TTT<br>Gly Glu Ile Ala Asp Leu Thr Pro Asp Thr Val Asn Ile Tyr Asn Phe<br>210　　　　　　　　　215　　　　　　　　　220 | | 672 |
| GAG GGA GAG CCC GTT TCA AAG GAA GTA ATG ATT ACG CCC TGG GAT CTT<br>Glu Gly Glu Pro Val Ser Lys Glu Val Met Ile Thr Pro Trp Asp Leu<br>225　　　　　　　　　230　　　　　　　　　235　　　　　　　　　240 | | 720 |

FIG. 6A

| | |
|---|---|
| GTT TCT GCG GAA AAG GGT GGT TTT AAA CAC TTC ATG CTA AAA GAG ATA<br>Val Ser Ala Glu Lys Gly Gly Phe Lys His Phe Met Leu Lys Glu Ile<br>      245        250        255 | 768 |
| TAC GAA CAG CCC AAA GCC ATA AAC GAC ACA CTC AAG GGT TTC CTC TCA<br>Tyr Glu Gln Pro Lys Ala Ile Asn Asp Thr Leu Lys Gly Phe Leu Ser<br>     260        265        270 | 816 |
| ACC GAA GAC GCA ATA CCC TTT AAG TTA AAA GAC TTC AGA AGG GTT TTA<br>Thr Glu Asp Ala Ile Pro Phe Lys Leu Lys Asp Phe Arg Arg Val Leu<br>  275        280        285 | 864 |
| ATA ATA GCG TGC GGG ACC TCT TAC CAC GCG GGC TTC GTC GGA AAG TAC<br>Ile Ile Ala Cys Gly Thr Ser Tyr His Ala Gly Phe Val Gly Lys Tyr<br>  290        295        300 | 912 |
| TGG ATA GAG AGA TTT GCA GGT GTT CCC ACA GAG GTA ATT TAC GCT TCG<br>Trp Ile Glu Arg Phe Ala Gly Val Pro Thr Glu Val Ile Tyr Ala Ser<br>305        310        315        320 | 960 |
| GAA TTC AGG TAT GCG GAC GTT CCC GTT TCG GAC AAG GAT ATC GTT ATC<br>Glu Phe Arg Tyr Ala Asp Val Pro Val Ser Asp Lys Asp Ile Val Ile<br>      325        330        335 | 1008 |
| GGA ATT TCC CAG TCA GGA GAG ACC GCT GAC ACA AAG TTT GCC CTT CAG<br>Gly Ile Ser Gln Ser Gly Glu Thr Ala Asp Thr Lys Phe Ala Leu Gln<br>     340        345        350 | 1056 |
| TCC GCA AAG GAA AAG GGA GCC TTT ACC GTG GGA CTC GTA AAC GTA GTG<br>Ser Ala Lys Glu Lys Gly Ala Phe Thr Val Gly Leu Val Asn Val Val<br>  355        360        365 | 1104 |
| GGA AGT GCC ATA GAC AGG GAG TCG GAC TTT TCC CTT CAC ACA CAT GCG<br>Gly Ser Ala Ile Asp Arg Glu Ser Asp Phe Ser Leu His Thr His Ala<br>370        375        380 | 1152 |
| GGA CCC GAA ATA GGC GTG GCG GCT ACA AAG ACC TTC ACC GCA CAG TTC<br>Gly Pro Glu Ile Gly Val Ala Ala Thr Lys Thr Phe Thr Ala Gln Phe<br>385        390        395        400 | 1200 |
| ACC GCA CTC TAC GCC CTT TCG GTA AGG GAA AGT GAG GAG AGG GAA AAT<br>Thr Ala Leu Tyr Ala Leu Ser Val Arg Glu Ser Glu Glu Arg Glu Asn<br>     405        410        415 | 1248 |
| CTA ATA AGA CTC CTT GAA AAG GTT CCA TCA CTC GTT GAA CAA ACA CTG<br>Leu Ile Arg Leu Leu Glu Lys Val Pro Ser Leu Val Glu Gln Thr Leu<br>    420        425        430 | 1296 |
| AAC ACC GCA GAA GAA GTG GAG AAG GTA GCG GAA AAG TAC ATG AAA AAG<br>Asn Thr Ala Glu Glu Val Glu Lys Val Ala Glu Lys Tyr Met Lys Lys<br>  435        440        445 | 1344 |
| AAA AAC ATG CTT TAC CTC GGA AGG TAC TTA AAT TAC CCC ATA GCG CTG<br>Lys Asn Met Leu Tyr Leu Gly Arg Tyr Leu Asn Tyr Pro Ile Ala Leu<br>450        455        460 | 1392 |
| GAG GGA GCT CTT AAA CTT AAA GAA ATT TCT TAC ATA CAC GCG GAA GGT<br>Glu Gly Ala Leu Lys Leu Lys Glu Ile Ser Tyr Ile His Ala Glu Gly<br>465        470        475        480 | 1440 |
| TAT CCC GCA GGG GAG ATG AAG CAC GGT CCC ATA GCC CTC ATA GAC GAA<br>Tyr Pro Ala Gly Glu Met Lys His Gly Pro Ile Ala Leu Ile Asp Glu<br>     485        490        495 | 1488 |

FIG. 6B

```
AAC ATG CCG GTT GTG GTA ATC GCA CCG AAA GAC AGG GTT TAC GAG AAG        1536
Asn Met Pro Val Val Ile Ala Pro Lys Asp Arg Val Tyr Glu Lys
        500             505             510

ATA CTC TCA AAC GTA GAA GAG GTT CTC GCA AGA AAG GGA AGG GTT ATT        1584
Ile Leu Ser Asn Val Glu Glu Val Leu Ala Arg Lys Gly Arg Val Ile
        515             520             525

TCT GTA GGC TTT AAA GGA GAC GAA ACT CTC AAA AGC AAA TCC GAG AGC        1632
Ser Val Gly Phe Lys Gly Asp Glu Thr Leu Lys Ser Lys Ser Glu Ser
        530             535             540

GTT ATG GAA ATC CCG AAG GCA GAA GAA CCG ATA ACT CCT TTC TTG ACG        1680
Val Met Glu Ile Pro Lys Ala Glu Glu Pro Ile Thr Pro Phe Leu Thr
545             550             555             560

GTA ATA CCC CTG CAA CTC TTT GCC TAC TTT ATA GCG AGC AAA CTG GGA        1728
Val Ile Pro Leu Gln Leu Phe Ala Tyr Phe Ile Ala Ser Lys Leu Gly
                565             570             575
580

CTG GAT GTG GAT CAG CCG AGA AAT CTC GCC AAA ACG GTC ACG GTG GAA        1776
Leu Asp Val Asp Gln Pro Arg Asn Leu Ala Lys Thr Val Thr Val Glu
        580             585             590

TAA                                                                     1779
End
```

FIG. 6C

```
ATG ATA CCC CAG AGG ATT AAG GAA CTT GAA GCT TAC AAG ACG GAG GTC      48
Met Ile Pro Gln Arg Ile Lys Glu Leu Glu Ala Tyr Lys Thr Glu Val
            5                   10                  15

ACT CCC GCC TCC GTC AGG CTT TCC TCT AAC GAA TTC CCC TAC GAC TTT      96
Thr Pro Ala Ser Val Arg Leu Ser Ser Asn Glu Phe Pro Tyr Asp Phe
            20                  25                  30

CCC GAG GAG ATA AAA CAA AGG GCC TTA GAA GAA TTA AAA AAG GTT CCC     144
Pro Glu Glu Ile Lys Gln Arg Ala Leu Glu Glu Leu Lys Lys Val Pro
            35                  40                  45

TTG AAC AAA TAC CCA GAC CCC GAA GCG AAA GAG TTA AAA GCG GTT CTT     192
Leu Asn Lys Tyr Pro Asp Pro Glu Ala Lys Glu Leu Lys Ala Val Leu
            50                  55                  60

GCG GAT TTT TTC GGC GTT AAG GAA GAA AAT TTA GTT CTC GGT AAC GGT     240
Ala Asp Phe Phe Gly Val Lys Glu Glu Asn Leu Val Leu Gly Asn Gly
65                  70                  75                  80

TCG GAC GAA CTC ATA TAC TAC CTC TCA ATA GCT ATA GGT GAA CTT TAC     288
Ser Asp Glu Leu Ile Tyr Tyr Leu Ser Ile Ala Ile Gly Glu Leu Tyr
            85                  90                  95

ATA CCC GTT TAC ATA CCT GTT CCC ACC TTT CCC ATG TAC GAG ATA AGT     336
Ile Pro Val Tyr Ile Pro Val Pro Thr Phe Pro Met Tyr Glu Ile Ser
            100                 105                 110

GCG AAA GTT CTC GGA AGA CCC CTC GTA AAG GTT CAA CTG GAC GAA AAC     384
Ala Lys Val Leu Gly Arg Pro Leu Val Lys Val Gln Leu Asp Glu Asn
            115                 120                 125

TTT GAT ATA GAC TTA GAA AGA AGT ATT GAA TTA ATA GAG AAA GAA AAA     432
Phe Asp Ile Asp Leu Glu Arg Ser Ile Glu Leu Ile Glu Lys Glu Lys
            130                 135                 140

CCC GTT CTC GGG TAC TTT GCT TAC CCA AAC AAC CCC ACG GGA AAC CTC     480
Pro Val Leu Gly Tyr Phe Ala Tyr Pro Asn Asn Pro Thr Gly Asn Leu
145                 150                 155                 160

TTT TCC AGG GGA AAG ATT GAG GAG ATA AGA AAC AGG GGT GTT TTC TGT     528
Phe Ser Arg Gly Lys Ile Glu Glu Ile Arg Asn Arg Gly Val Phe Cys
            165                 170                 175

GTA ATA GAC GAA GCC TAC TAT CAT TAC TCC GGA GAA ACC TTT CTG GAA     576
Val Ile Asp Glu Ala Tyr Tyr His Tyr Ser Gly Glu Thr Phe Leu Glu
            180                 185                 190

GAC GCG CTC AAA AGG GAA GAT ACG GTA GTT TTG AGG ACA CTT TCA AAA     624
Asp Ala Leu Lys Arg Glu Asp Thr Val Val Leu Arg Thr Leu Ser Lys
            195                 200                 205

ATC GGT ATG GCG AGT TTA AGG GTA GGG ATT TTA ATA GGG AAG GGG GAA     672
Ile Gly Met Ala Ser Leu Arg Val Gly Ile Leu Ile Gly Lys Gly Glu
            210                 215                 220

ATC GTC TCA GAA ATT AAC AAG GTG AGA CTC CCC TTC AAC GTG ACC TAC     720
Ile Val Ser Glu Ile Asn Lys Val Arg Leu Pro Phe Asn Val Thr Tyr
225                 230                 235                 240
```

FIG. 7A

```
CCC TCT CAG GTG ATG GCA AAA GTT CTC CTC ACG GAG GGA AGA GAA TTC     768
Pro Ser Gln Val Met Ala Lys Val Leu Leu Thr Glu Gly Arg Glu Phe
            245                 250                 255

CTA ATG GAA AAG ATA CAG GAG GTT GTA ACA GAG CGA GAA AGG ATG TAC     816
Leu Met Glu Lys Ile Gln Glu Val Val Thr Glu Arg Glu Arg Met Tyr
            260                 265                 270

GAC GAA ATG AAG AAA ATA GAA GGA GTT GAG GTT TTT CCG AGT AAG GCT     864
Asp Glu Met Lys Lys Ile Glu Gly Val Glu Val Phe Pro Ser Lys Ala
            275                 280                 285

AAC TTC TTG CTT TTC AGA ACG CCT TAC CCC GCC CAC GAG GTT TAT CAG     912
Asn Phe Leu Leu Phe Arg Thr Pro Tyr Pro Ala His Glu Val Tyr Gln
    290                 295                 300

GAG CTA CTG AAA AGG GAT GTC CTC GTC AGG AAC GTA TCT TAC ATG GAA     960
Glu Leu Leu Lys Arg Asp Val Leu Val Arg Asn Val Ser Tyr Met Glu
305                 310                 315                 320

GGA CTC CAA AAG TGC CTC AGG GTA AGC GTA GGG AAA CCG GAA GAA AAC    1008
Gly Leu Gln Lys Cys Leu Arg Val Ser Val Gly Lys Pro Glu Glu Asn
                325                 330                 335

AAC AAG TTT CTG GAA GCA CTG GAG GAG AGT ATA AAA TCC CTT TCA AGC    1056
Asn Lys Phe Leu Glu Ala Leu Glu Glu Ser Ile Lys Ser Leu Ser Ser
            340                 345                 350

TCT CTT TAA                                                        1065
Ser Leu End
```

FIG. 7B

| | | | | | | | | | | | | | | | |
|---|---|---|---|---|---|---|---|---|---|---|---|---|---|---|---|
| ATG | AAG | CCG | TAC | GCT | AAA | TAT | ATC | TGG | CTT | GAC | GGC | AGA | ATA | CTT | AAG | 48
| Met | Lys | Pro | Tyr | Ala | Lys | Tyr | Ile | Trp | Leu | Asp | Gly | Arg | Ile | Leu | Lys |
| | | | | 5 | | | | | 10 | | | | | 15 | |
| TGG | GAA | GAC | GCG | AAA | ATA | CAC | GTG | TTG | ACT | CAC | GCG | CTT | CAC | TAC | GGA | 96
| Trp | Glu | Asp | Ala | Lys | Ile | His | Val | Leu | Thr | His | Ala | Leu | His | Tyr | Gly |
| | | | | 20 | | | | | 25 | | | | | 30 | |
| ACC | TCT | ATA | TTC | GAG | GGA | ATA | AGA | GGG | TAT | TGG | AAC | GGC | GAT | AAT | TTG | 144
| Thr | Ser | Ile | Phe | Glu | Gly | Ile | Arg | Gly | Tyr | Trp | Asn | Gly | Asp | Asn | Leu |
| | | | | 35 | | | | | 40 | | | | | 45 | |
| CTC | GTC | TTT | AGG | TTA | GAA | GAA | CAC | ATC | GAC | CGC | ATG | TAC | AGA | TCG | GCT | 192
| Leu | Val | Phe | Arg | Leu | Glu | Glu | His | Ile | Asp | Arg | Met | Tyr | Arg | Ser | Ala |
| | | | | 50 | | | | | 55 | | | | | 60 | |
| AAG | ATA | CTA | GGC | ATA | AAT | ATT | CCG | TAT | ACA | AGA | GAG | GAA | GTC | CGC | CAA | 240
| Lys | Ile | Leu | Gly | Ile | Asn | Ile | Pro | Tyr | Thr | Arg | Glu | Glu | Val | Arg | Gln |
| 65 | | | | | 70 | | | | | 75 | | | | | 80 |
| GCT | GTA | CTA | GAG | ACC | ATA | AAG | GCT | AAT | AAC | TTC | CGA | GAG | GAT | GTC | TAC | 288
| Ala | Val | Leu | Glu | Thr | Ile | Lys | Ala | Asn | Asn | Phe | Arg | Glu | Asp | Val | Tyr |
| | | | | 85 | | | | | 90 | | | | | 95 | |
| ATA | AGA | CCT | GTG | GCG | TTT | GTC | GCC | TCG | CAG | ACG | GTG | ACG | CTT | GAC | ATA | 336
| Ile | Arg | Pro | Val | Ala | Phe | Val | Ala | Ser | Gln | Thr | Val | Thr | Leu | Asp | Ile |
| | | | | 100 | | | | | 105 | | | | | 110 | |
| AGA | AAT | TTG | GAA | GTC | TCC | CTC | GCG | GTT | ATT | GTA | TTC | CCA | TTT | GGC | AAA | 384
| Arg | Asn | Leu | Glu | Val | Ser | Leu | Ala | Val | Ile | Val | Phe | Pro | Phe | Gly | Lys |
| | | | | 115 | | | | | 120 | | | | | 125 | |
| TAC | CTC | TCG | CCC | AAC | GGC | ATT | AAG | GCA | ACG | ATT | GTA | AGC | TGG | CGT | AGA | 432
| Tyr | Leu | Ser | Pro | Asn | Gly | Ile | Lys | Ala | Thr | Ile | Val | Ser | Trp | Arg | Arg |
| | | | | 130 | | | | | 135 | | | | | 140 | |
| GTA | CAT | AAT | ACA | ATG | CTC | CCT | GTG | ATG | GCA | AAA | ATC | GGC | GGT | ATA | TAT | 480
| Val | His | Asn | Thr | Met | Leu | Pro | Val | Met | Ala | Lys | Ile | Gly | Gly | Ile | Tyr |
| 145 | | | | | 150 | | | | | 155 | | | | | 160 |
| GTA | AAC | TCT | GTA | CTT | GCG | CTT | GTA | GAG | GCT | AGA | AGC | AGG | GGA | TTT | GAC | 528
| Val | Asn | Ser | Val | Leu | Ala | Leu | Val | Glu | Ala | Arg | Ser | Arg | Gly | Phe | Asp |
| | | | | 165 | | | | | 170 | | | | | 175 | |
| GAG | GCT | TTA | TTA | ATG | GAC | GTT | AAC | GGT | TAT | GTT | GTT | GAG | GGT | TCT | GGA | 576
| Glu | Ala | Leu | Leu | Met | Asp | Val | Asn | Gly | Tyr | Val | Val | Glu | Gly | Ser | Gly |
| | | | | 180 | | | | | 185 | | | | | 190 | |
| GAG | AAT | ATT | TTC | ATT | GTC | AGA | GGT | GGA | AGG | CTT | TTC | ACG | CCG | CCA | GTA | 624
| Glu | Asn | Ile | Phe | Ile | Val | Arg | Gly | Gly | Arg | Leu | Phe | Thr | Pro | Pro | Val |
| | | | | 195 | | | | | 200 | | | | | 205 | |
| CAC | GAA | TCT | ATC | CTC | GAG | GGA | ATT | ACG | AGG | GAT | ACG | GTA | ATA | AAG | CTC | 672
| His | Glu | Ser | Ile | Leu | Glu | Gly | Ile | Thr | Arg | Asp | Thr | Val | Ile | Lys | Leu |
| | | | | 210 | | | | | 215 | | | | | 220 | |
| AGC | GGG | GAT | GTG | GGA | CTT | CGG | GTG | GAG | GAA | AAG | CCT | ATT | ACG | AGG | GAG | 720
| Ser | Gly | Asp | Val | Gly | Leu | Arg | Val | Glu | Glu | Lys | Pro | Ile | Thr | Arg | Glu |
| 225 | | | | | 230 | | | | | 235 | | | | | 240 |

FIG. 8A

```
GAG GTG TAT ACA GCC GAC GAG GTG TTT TTA GTA GGA ACC GCC GCA GAG        768
Glu Val Tyr Thr Ala Asp Glu Val Phe Leu Val Gly Thr Ala Ala Glu
            245             250             255

ATA ACG CCA GTG GTG GAG GTT GAC GGC AGA ACA ATC GGC ACA GGC AAG        816
Ile Thr Pro Val Val Glu Val Asp Gly Arg Thr Ile Gly Thr Gly Lys
            260             265             270

CCG GGC CCC ATT ACG ACA AAA ATA GCT GAG CTG TAC TCA AAC GTC GTG        864
Pro Gly Pro Ile Thr Thr Lys Ile Ala Glu Leu Tyr Ser Asn Val Val
            275             280             285

AGA GGC AAA GTA GAG AAA TAC TTA AAT TGG ATC ACT CCT GTG TAT TAG        912
Arg Gly Lys Val Glu Lys Tyr Leu Asn Trp Ile Thr Pro Val Tyr End
            290             295             300
```

FIG. 8B

Ammonifex degensii histidinol phosphate aminotransferase

```
   1 ATG GCA GTC AAA GTG CGG CCT GAG CTC AGC CAG GTG GAG ATC TAC CGT CCC GGC AAA CCC   60
   1 Met Ala Val Lys Val Arg Pro Glu Leu Ser Gln Val Glu Ile Tyr Arg Pro Gly Lys Pro   20

61 ATC GAA GAG GTA AAG AAG GAG CTG GGG CTG GAG GAG GTA GTC AAG CTG GCC TCC AAC GAG  120
  21 Ile Glu Glu Val Lys Lys Glu Leu Gly Leu Glu Glu Val Val Lys Leu Ala Ser Asn Glu   40

121 AAC CCT CTG GGA CCT TCT CCC AAG GCC GTG GCG GCG CTG GAG GGA CTG GAC CAC TGG CAC  180
  41 Asn Pro Leu Gly Pro Ser Pro Lys Ala Val Ala Ala Leu Glu Gly Leu Asp His Trp His   60

181 CTT TAC CCA GAA GGC TCA AGC TAT GAG CTA CGG CAG GCG CTG GGT AAG AAA CTG GAG ATA  240
  61 Leu Tyr Pro Glu Gly Ser Ser Tyr Glu Leu Arg Gln Ala Leu Gly Lys Lys Leu Glu Ile   80

241 GAC CCG GAC AGC ATC ATC GTG GGT TGC GGC TCA AGC GAA GTC ATC CAG ATG CTC TCT TTG  300
  81 Asp Pro Asp Ser Ile Ile Val Gly Cys Gly Ser Ser Glu Val Ile Gln Met Leu Ser Leu  100

301 GCC CTG CTG GCG CCC GGC GAC GAG GTG GTC ATC CCT GTG CCT ACC TTT CCC CGC TAT GAG  360
 101 Ala Leu Leu Ala Pro Gly Asp Glu Val Val Ile Pro Val Pro Thr Phe Pro Arg Tyr Glu  120

361 CCC CTG GCA CGG CTC ATG GGG GCT AAT CCC GTA AAA GTT CCC TTG AAG GAC TAC CGC ATC  420
 121 Pro Leu Ala Arg Leu Met Gly Ala Asn Pro Val Lys Val Pro Leu Lys Asp Tyr Arg Ile  140

421 GAT GTG GAG GCA GTG GCC CGA GCC CTT TCC CCC CGT ACC AAG CTG GTC TAC CTA TGC AAC  480
 141 Asp Val Glu Ala Val Ala Arg Ala Leu Ser Pro Arg Thr Lys Leu Val Tyr Leu Cys Asn  160

481 CCC AAC AAC CCC ACC GGG ACC ATC GTC ACC CGG GAG GAG GTG GAG TGG TTC TTG GAA AAG  540
 161 Pro Asn Asn Pro Thr Gly Thr Ile Val Thr Arg Glu Glu Val Glu Trp Phe Leu Glu Lys  180

541 GCG GGG GAG GGG GTT CTC ACC GTG CTG GAC GAG GCC TAC TGC GAG TAC GTG ACC AGC CCC  600
 181 Ala Gly Glu Gly Val Leu Thr Val Leu Asp Glu Ala Tyr Cys Glu Tyr Val Thr Ser Pro  200

601 GCC TAC CCT GAT GGG CTC GAT TTC CTG CGC CGG GGC TAC AAT GTG GTG GTG CTG CGC ACC  660
 201 Ala Tyr Pro Asp Gly Leu Asp Phe Leu Arg Arg Gly Tyr Asn Val Val Val Leu Arg Thr  220

661 TTC TCC AAG ATC TAC GGG CTG GCC GGG CTG CGC ATA GGG TAC GGT GTG GCG GAC AGG GAG  720
 221 Phe Ser Lys Ile Tyr Gly Leu Ala Gly Leu Arg Ile Gly Tyr Gly Val Ala Asp Arg Glu  240

721 CTG GTG GCG GAA CTG CAC CGG GTG CGG GAG CCT TTC AAT GTC AGT TCC GCT GCT CAG ATA  780
 241 Leu Val Ala Glu Leu His Arg Val Arg Glu Pro Phe Asn Val Ser Ser Ala Ala Gln Ile  260

781 GCC GCC CTG GCC GCC CTG GAA GAC GAA GAG TTC GTG GCG CTT TCG CGC CAG GTC AAC GAA  840
 261 Ala Ala Leu Ala Ala Leu Glu Asp Glu Glu Phe Val Ala Leu Ser Arg Gln Val Asn Glu  280

841 GAA GGG AAG GTT TTT CTC TAC CGA GAA CTG GAG AGG CGG GGG ATC GCC TAC GTG CCC ACC  900
 281 Glu Gly Lys Val Phe Leu Tyr Arg Glu Leu Glu Arg Arg Gly Ile Ala Tyr Val Pro Thr  300

901 GAG GCC AAC TTC CTA CTC TTC GAT GCC GGT CGG GAC GAG CAG GAA GTA TTT CGC CGG ATG  960
 301 Glu Ala Asn Phe Leu Leu Phe Asp Ala Gly Arg Asp Glu Gln Glu Val Phe Arg Arg Met  320

961 CTG CGC CAG GGA GTG ATC ATC CGG GNC GGG GTG GGT TAT CCC ACC CAC TTA AGG GTG ACC 1020
 321 Leu Arg Gln Gly Val Ile Ile Arg Xxx Gly Val Gly Tyr Pro Thr His Leu Arg Val Thr  340

1021 ATC GGC ACC TTG GAA CAG AAC CAG CGC TTC CTG GAA GCT TTG GAT AAG GCT CTA GAG CTT 1080
 341 Ile Gly Thr Leu Glu Gln Asn Gln Arg Phe Leu Glu Ala Leu Asp Lys Ala Leu Glu Leu  360

1081 AGG GGG GTT TAA 1092
 361 Arg Gly Val End  364
```

FIG. 9

*Aquifex* aspartate aminotransferase

```
   1 ATG AGA AAA GGA CTT GCA AGT AGG GTA AGT CAC CTA AAA CCT TCC CCC ACG CTG ACC ATA   60
     Met Arg Lys Gly Leu Ala Ser Arg Val Ser His Leu Lys Pro Ser Pro Thr Leu Thr Ile

61 ACC GCA AAA GCA AAA GAA TTA AGG GCT AAA GGA GTG GAC GTT ATA GGT TTT GGA GCG GGA  120
     Thr Ala Lys Ala Lys Glu Leu Arg Ala Lys Gly Val Asp Val Ile Gly Phe Gly Ala Gly

121 GAA CCT GAC TTC GAC ACA CCC GAC TTC ATA AAG GAA GCC TGT ATA AGG GCT TTA AGG GAA  180
     Glu Pro Asp Phe Asp Thr Pro Asp Phe Ile Lys Glu Ala Cys Ile Arg Ala Leu Arg Glu

181 GGA AAG ACC AAG TAC GCT CCC TCC GCG GGA ATA CCA GAG CTC AGA GAA GCT ATA GCT GAA  240
     Gly Lys Thr Lys Tyr Ala Pro Ser Ala Gly Ile Pro Glu Leu Arg Glu Ala Ile Ala Glu

241 AAA CTA CTG AAA GAA AAC AAA GTT GAG TAC AAA CCT TCA GAG ATA GTC GTT TCC GCA GGA  300
     Lys Leu Leu Lys Glu Asn Lys Val Glu Tyr Lys Pro Ser Glu Ile Val Val Ser Ala Gly

301 GCG AAA ATG GTT CTC TTC CTC ATA TTC ATG GCT ATA CTG GAC GAA GGA GAC GAG GTT TTA  360
     Ala Lys Met Val Leu Phe Leu Ile Phe Met Ala Ile Leu Asp Glu Gly Asp Glu Val Leu

361 CTA CCT AGC CCT TAC TGG GTA ACT TAC CCC GAA CAG ATA AGG TTC TTC GGA GGG GTT CCC  420
     Leu Pro Ser Pro Tyr Trp Val Thr Tyr Pro Glu Gln Ile Arg Phe Phe Gly Gly Val Pro

421 GTT GAG GTT CCT CTA AAG AAA GAG AAA GGA TTT CAA TTA AGT CTG GAA GAT GTG AAA GAA  480
     Val Glu Val Pro Leu Lys Lys Glu Lys Gly Phe Gln Leu Ser Leu Glu Asp Val Lys Glu

481 AAG GTT ACG GAG AGA ACA AAA GCT ATA GTC ATA AAC TCT CCG AAC AAC CCC ACT GGT GCT  540
     Lys Val Thr Glu Arg Thr Lys Ala Ile Val Ile Asn Ser Pro Asn Asn Pro Thr Gly Ala

541 GTT TAC GAA GAG GAG GAA CTT AAG AAA ATA GCG GAG TTT TGC GTG GAG AGG GGC ATT TTC  600
     Val Tyr Glu Glu Glu Glu Leu Lys Lys Ile Ala Glu Phe Cys Val Glu Arg Gly Ile Phe

601 ATA ATT TCC GAT GAG TGC TAT GAG TAC TTC GTT TAC GGT GAT GCA AAA TTT GTT AGC CCT  660
     Ile Ile Ser Asp Glu Cys Tyr Glu Tyr Phe Val Tyr Gly Asp Ala Lys Phe Val Ser Pro

661 GCC TCT TTC TCG GAT GAA GTA AAG AAC ATA ACC TTC ACG GTA AAC GCC TTT TCG AAG AGC  720
     Ala Ser Phe Ser Asp Glu Val Lys Asn Ile Thr Phe Thr Val Asn Ala Phe Ser Lys Ser

721 TAT TCC ATG ACT GGT TGG CGA ATA GGT TAT GTA GCG TGC CCC GAA GAG TAC GCA AAA GTG  780
     Tyr Ser Met Thr Gly Trp Arg Ile Gly Tyr Val Ala Cys Pro Glu Glu Tyr Ala Lys Val

781 ATA GCG AGT CTT AAC AGC CAG AGT GTT TCC AAC GTC ACT ACC TTT GCC CAG TAT GGA GCT  840
     Ile Ala Ser Leu Asn Ser Gln Ser Val Ser Asn Val Thr Thr Phe Ala Gln Tyr Gly Ala

841 CTT GAG GCC TTG AAA AAT CCA AAG TCT AAA GAT TTT GTA AAC GAA ATG AGA AAT GCT TTT  900
     Leu Glu Ala Leu Lys Asn Pro Lys Ser Lys Asp Phe Val Asn Glu Met Arg Asn Ala Phe

901 GAA AGG AGA AGG GAT ACG GCT GTA GAA GAG CTT TCT AAA ATT CCA GGT ATG GAT GTG GTA  960
     Glu Arg Arg Arg Asp Thr Ala Val Glu Glu Leu Ser Lys Ile Pro Gly Met Asp Val Val

961 AAA CCC GAA GGT GCC TTT TAC ATA TTT CCG GAC TTC TCC GCT TAC GCT GAG AAA CTG GGT 1020
     Lys Pro Glu Gly Ala Phe Tyr Ile Phe Pro Asp Phe Ser Ala Tyr Ala Glu Lys Leu Gly

1021 GGT GAT GTG AAA CTC TCG GAG TTC CTT CTG GAA AAG GCT AAG GTT GCG GTG GTT CCC GGT 1080
     Gly Asp Val Lys Leu Ser Glu Phe Leu Leu Glu Lys Ala Lys Val Ala Val Val Pro Gly

1081 TCG GCC TTC GGA GCT CCC GGA TTT TTG AGG CTT TCT TAC GCC CTT TCC GAG GAA AGA CTC 1140
     Ser Ala Phe Gly Ala Pro Gly Phe Leu Arg Leu Ser Tyr Ala Leu Ser Glu Glu Arg Leu

1141 GTT GAG GGT ATA AGG AGA ATA AAG AAA GCC CTT GAA GAG ATC TAA 1185
     Val Glu Gly Ile Arg Arg Ile Lys Lys Ala Leu Glu Glu Ile End
```

FIG. 10

TRANSAMINASES AND AMINOTRANSFERASES

This application is a continuation of 08/646,590, filed on May 8, 1996, which issued as U.S. Pat. No. 5,962,283, which is a continuation-in-part of 08/599,171 filed on Feb. 9, 1996, which issued as U.S. Pat. No. 5,814,473.

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as transaminases and/or aminotransferases. Aminotransferases are enzymes that catalyze the transfer of amino groups from α-amino to α-keto acids. They are also called transaminases.

The α-amino groups of the 20 L-amino acids commonly found in proteins are removed during the oxidative degradation of the amino acids. The removal of the α-amino groups, the first step in the catabolism of most of the L-amino acids, is promoted by aminotransferases (or transaminases). In these transamination reactions, the α-amino group is transferred to the α-carbon atom of α-ketoglutarate, leaving behind the corresponding α-keto acid analog of the amino acid. There is no net deamination (i.e., loss of amino groups) in such reactions because the α-ketoglutarate becomes aminated as the α-amino acid is deaminated. The effect of transamination reactions is to collect the amino groups from many different amino acids in the form of only one, namely, L-glutamate. The glutamate channels amino groups either into biosynthetic pathways or into a final sequence of reactions by which nitrogenous waste products are formed and then excreted.

Cells contain several different aminotransferases, many specific for α-ketoglutarate as the amino group acceptor. The aminotransferases differ in their specificity for the other substrate, the L-amino acid that donates the amino group, and are named for the amino group donor. The reactions catalyzed by the aminotransferases are freely reversible, having an equilibrium constant of about 1.0 ($\Delta G^{0'} \approx 0$ kJ/mol).

Aminotransferases are classic examples of enzymes catalyzing bimolecular ping-pong reactions. In such reactions the first substrate must leave the active site before the second substrate can bind. Thus the incoming amino acid binds to the active site, donates its amino group to pyridoxal phosphate, and departs in the form of an α-keto acid. Then the incoming α-keto acid is bound, accepts the amino group from pyridoxamine phosphate, and departs in the form of an amino acid.

The measurement of alanine aminotransferase and aspartate aminotransferase levels in blood serum is an important diagnostic procedure in medicine, used as an indicator of heart damage and to monitor recovery from the damage.

The polynucleotides and polypeptides of the present invention have been identified as transaminases and/or aminotransferases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes, or polynucleotides encoding such enzymes for transferring an amino group from an ax-amino acid to an α-keto acid. Most transaminases use L-amino acids as substrates, but as described below, it is also possible to convert the transaminases of the invention to use D-amino acids as substrates, thereby increasing their array of uses to include, for example, manufacture of synthetic pyrethroids and as components of β-lactam antibiotics. The transaminases of the invention are stable at high temperatures and in organic solvents and, thus, are superior for use with L- and/or D-amino acids for production of optically pure chiral compounds used in pharmaceutical, agricultural and other chemical industries.

In accordance with yet a further aspect of the present invention, there are also provided nucleic acid probes comprising nucleic acid molecules of sufficient length to hybridize to a nucleic acid sequence of the present invention.

In accordance with yet a further aspect of the present invention, there is provided a process, for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

The following drawings are illustrative of embodiments of the invention and are not meant to limit the scope of the invention as encompassed by the claims.

FIG. 1 is an illustration of the full-length DNA (SEQ ID NO: 17) and corresponding deduced amino acid sequence (SEQ ID NO:25) of Aquifex aspartate transaminase A of the present invention. Sequencing was performed using a 378 automated DNA sequencer (Applied Biosystems, Inc.) for all sequences of the present invention.

FIG. 2 is an illustration of the full-length DNA (SEQ ID NO:18) and corresponding deduced amino acid sequence (SEQ ID NO:26) of Aquifex aspartate aminotransferase B.

FIG. 3 is an illustration of the full-length DNA (SEQ ID NO:19) and corresponding deduced amino acid sequence (SEQ ID NO:27) of Aquifex adenosyl-8-amino-7-oxononanoate aminotransferase.

FIG. 4 is an illustration of the full-length DNA (SEQ ID NO:20) and corresponding deduced amino acid sequence (SEQ ID NO:28) of Aquifex acetylornithine aminotransferase.

FIG. 5 is an illustration of the full-length DNA (SEQ ID NO:21) and corresponding deduced amino acid sequence (SEQ ID NO:29) of *Ammonifex degensii* aspartate aminotransferase.

FIG. 6 is an illustration of the full-length DNA (SEQ ID NO:22) and corresponding deduced amino acid sequence (SEQ ID NO:30) of Aquifex glucosamine:fructose-6-phosphate aminotransferase.

FIG. 7 is an illustration of the full-length DNA (SEQ ID NO:23) and corresponding deduced amino acid sequence (SEQ ID NO:31) of Aquifex histidinolphosphate aminotransferase.

FIG. 8 is an illustration of the full-length DNA (SEQ ID NO:24) and corresponding deduced amino acid sequence (SEQ ID NO:32) of *Pyrobacullum aerophilum* branched chain aminotransferase.

FIG. 9 is an illustration of the full-length DNA (SEQ ID NO:35) and corresponding deduced amino acid sequence (SEQ ID NO:36) of Ammonifex histidinol phosphate aminotransferase.

FIG. 10 is an illustration of the full-length DNA (SEQ ID NO:39) and corresponding deduced amino acid sequence (SEQ ID NO:40) of Aquifex aspartate aminotransferase.

Figure 11:
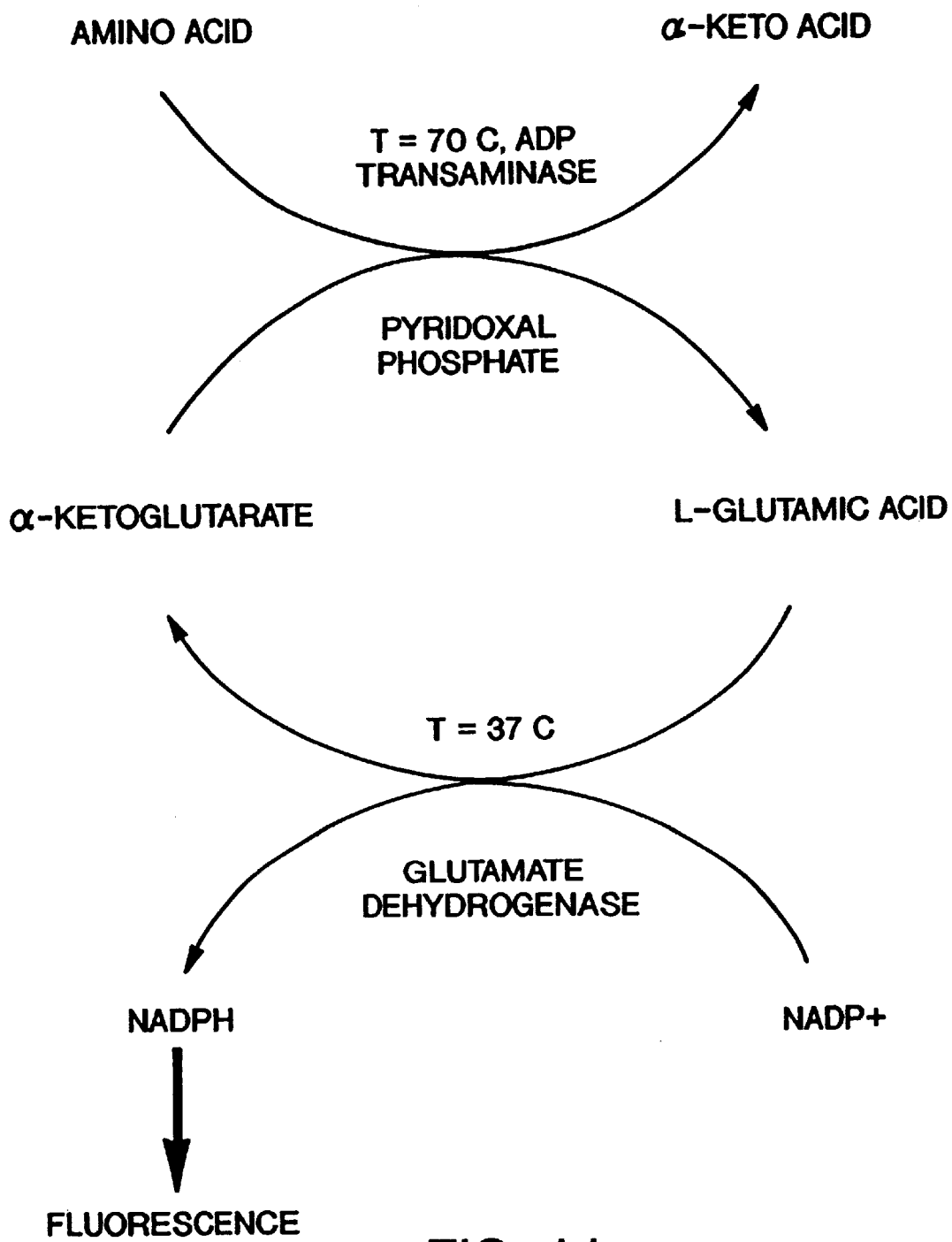
FIG. 11 is a diagramatic illustration of the assay used to assess aminotransferase activity of the proteins using glutamate dehydrogenase.

The term "gene" means the segment of DNA involved in producing a polypeptide chain; it includes regions preceding and following the coding region (leader and trailer) as well as intervening sequences (introns) between individual coding segments (exons).

A coding sequence is "operably lined to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

In accordance with an aspect of the present invention, there are provided isolated nucleic acids (polynucleotides) which encode for the mature enzymes having the deduced amino acid sequences of FIGS. 1–8 (SEQ ID NOS: 17–32).

The polynucleotides of this invention were originally recovered from genomic DNA libraries derived from the following organisms:

Aquifex VF5 is a Eubacteria which was isolated in Vulcano, Italy. It is a gram-negative, rod-shaped, strictly chemolithoautotrophic, marine organism which grows optimally at 85–90° C. ($T_{max}$=95° C.) at pH 6.8 in a high salt culture medium with $O_2$ as a substrate, and $H_2/CO_2$+0.5% $O_2$ in gas phase.

*Ammonifex degensii* KC4 is a new Eubacaterial organism isolated in Java, Indonesia. This Gram negative chemolithoautotroph has three respiration systems. The bacterium can utilize nitrate, sulfate, and sulfur. The organism grows optimally at 70° C., and pH 7.0, in a low salt culture medium with 0.2% nitrate as a substrate and $H_2/CO_2$ in gas phase.

*Pyrobaculum aerophilium* IM2 is a thermophilic sulfur archaea (Crenarchaeota) isolated in Ischia Maronti, Italy. It is a rod-shaped organism that grows optimally at 100° C. at pH 7.0 in a low salt culture medium with nitrate, yeast extract, peptone, and $O_2$ as substrates and $N_2/CO_2$, $O_2$ in gas phase.

Accordingly, the polynucleotides and enzymes encoded thereby are identified by the organism from which they were isolated, and are sometimes hereinafter referred to as "VF5/ATA" (FIG. 1 and SEQ ID NOS: 17 and 25), "VF5/AAB" (FIG. 2 and SEQ ID NOS: 18 and 26), "VF5/A87A" (FIG. 3 and SEQ ID NOS: 19 and 27), "VF5/AOA" (FIG. 4 and SEQ ID NOS:20 and 28), "KC4/AA" (FIG. 5 and SEQ ID NOS:21 and 29), "VF5/GF6PA" (FIG. 6 and SEQ ID NOS:22 and 30), "VF5/HPA" (FIG. 7 and SEQ ID NOS:23 and 31) and "IM2/BCA" (FIG. 8 and SEQ ID NOS:24 and 32).

The polynucleotides and polypeptides of the present invention show identity at the nucleotide and protein level to known genes and proteins encoded thereby as shown in Table 1.

TABLE 1

| Enzyme | Gene w/closest Homology (Organism) | Protein Similarity (%) | Protein Identity (%) | DNA Identity (%) |
|---|---|---|---|---|
| VF5/ATA | *Bacillus subtilis* | 57.5 | 38.3 | 50.1 |
| VF5/AAB | *Sulfolobus solfataricus* | 62.5 | 33.0 | 50.1 |
| VF5/A87A | *Bacillus sphaericus* BioA | 67.4 | 42.9 | 51 |
| VF5/AOA | *Bacillus subtilis* argD | 70.6 | 48.7 | 52.0 |
| KC4/AA | Bacillus YM-2 aspC | 72.6 | 52.7 | 52.0 |
| VF5/GF6PA | Rhizobium Leguminosarum NodM | 66.3 | 47.7 | 51.0 |
| VF5/HPA | *Bacillus subtilis* HisH/*E. coli* HisC (same gene) | 55.7 | 32.6 | 45.3 |
| IM2/BCA | *E. coli* iluE | 63.7 | 43.6 | 49.7 |

All the clones identified in Table 1 encode polypeptides which have transaminase or aminotransferase activity.

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that the polynucleodides of SEQ ID NOS: 17–24, or fragments thereof (comprising at least 12 contiguous nucleodides), are particularly useful probes. Other particularly useful probes for this purpose are hybridizable fragments of the sequences of SEQ ID NOS:1–9 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10X Denhardt's, and 0.5 mg/mL polyriboadenylic acid. Approximately $2\times10^7$ cpm (specific activity $4–9\times10^8$ cpm/ug) of $^{32}P$ end-labeled oligonucleotide probe are then added to the solution. After 12–16 hours of incubation, the membrane is washed for 30 minutes at room temperature in 1X SET (150 mM NaCl, 20 mM Tris hydrochloride, pH 7.8, 1 mM $Na_2EDTA$) containing 0.5 % SDS, followed by a 30 minute wash in fresh 1X SET at Tm −10° C. (Tm is minus 10° C.) for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., *Molecular Cloning, A Laboratory Manual,* 2d Ed., Cold Spring Harbor Laboratory (1989) which is hereby incorporated by reference in its entirety.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide such that the changes are silent changes, for example the change does not or the changes do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of this invention were recovered from genomic gene libraries from the organisms listed in Table 1. Gene libraries were generated in the Lambda ZAP II cloning vector (Stratagene Cloning Systems). Mass excisions were performed on these libraries to generate libraries in the pBluescript phagemid. Libraries were generated and excisions were performed according to the protocols/methods hereinafter described.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature enzymes may be identical to the coding sequences shown in FIGS. 1–8 (SEQ ID NOS: 17–24) or may be a different coding sequence which coding sequence, as a result of the redundancy or degeneracy of the genetic code, encodes the same mature enzymes as the DNA of FIGS. 1–8 (SEQ ID NOS:17–24).

The polynucleotide which encodes for the mature enzyme of FIGS. 1–8 (SEQ ID NOS:25–32) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of FIGS. 1–8 (SEQ ID NOS:25–32). The variant of the polynucleotide may be a naturally occurring allelic variant of the polynucleotide or a non-naturally occurring variant of the polynucleotide.

Thus, the present invention includes polynucleotides encoding the same mature enzymes as shown in FIGS. 1–8 (SEQ ID NOS:17–24) as well as variants of such polynucleotides which variants encode for a fragment, derivative or analog of the enzymes of FIGS. 1–8 (SEQ ID NOS: 17–24). Such nucleotide variants include deletion variants, substitution variants and addition or insertion variants.

As hereinabove indicated, the polynucleotides may have a coding sequence which is a naturally occurring allelic variant of the coding sequences shown in FIGS. 1–8 (SEQ ID NOS: 17–24). As known in the art, an allelic variant is an alternate form of a polynucleotide sequence which may have a substitution, deletion or addition of one or more nucleotides, which does not substantially alter the function of the encoded enzyme. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIGS. 1–8 (SEQ ID NOS: 17–24).

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 17–24, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzymes of SEQ ID NOS:25–32 as well as fragments thereof, which fragments have at least 15 bases, preferably at least 30 bases and most preferably at least 50 bases, which fragments are at least 90% identical, preferably at least 95% identical and most preferably at least 97% identical under stringent conditions to any portion of a polynucleotide of the present invention.

The present invention further relates to enzymes which have the deduced amino acid sequences of FIGS. 1–8 (SEQ ID NOS: 17–24) as well as fragments, analogs and derivatives of such enzyme.

The terms "fragment," "derivative" and "analog" when referring to the enzymes of FIGS. 1–8 (SEQ ID NOS:25–32) means enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of FIGS. 1–8 (SEQ ID NOS:25–32) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzymes of SEQ ID NOS:25–32 (in particular the mature enzyme) as well as enzymes which have at least 70% similarity (preferably at least 70% identity) to the enzymes of SEQ ID NOS:25–32 and more preferably at least 90% similarity (more preferably at least 90% identity) to the enzymes of SEQ ID NOS:25–32 and still more preferably at least 95% similarity (still more preferably at least 95% identity) to the enzymes of SEQ ID NOS:25–32 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gin, exchange of the basic residues Lys and Arg and replacements among the aromatic residues Phe, Tyr. Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the $E.$ $coli.$ lac or tip, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Bacillus subtilis;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition,* Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell,*

23:175 (1981), and other cell lines capable of expressing a compatible vector, for example, the C127, 3T3, CHO, Hela and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

Transaminases are a group of key enzymes in the metabolism of amino acids and amino sugars and are found in all organisms from microbes to mammals. In the transamination reaction, an amino group is transferred from an amino acid to an α-keto acid. Pyridoxal phosphate is required as a co-factor to mediate the transfer of the amino group without liberation of ammonia.

Amino acids currently have applications as additives to aminal feed, human nutritional supplements, components in infusion solutions, and synthetic intermediates for manufacture of pharmaceuticals and agricultural products. For example, L-glutamic acid is best known as a flavor enhancer for human food. L-lysine and L-methionine are large volume additives to animal feed and human supplements. L-tryptophan and L-threonine have similar potential applications. L-phenylalanine and L-aspartic acid have very important market potential as key components in the manufacture of the low-calorie sweetener aspartame, and other promising low-calorie sweeteners have compositions containing certain amino acids as well. Infusion solutions require a large range of amino acids including those essential ones in human diets.

Transaminases are highly stereoselective, and most use L-amino acids as substrates. Using the approach disclosed in a commonly assigned, copending application; U.S. application Ser. No. 08/646,590, filed on May 8, 1996 and entitled "Transaminases and aminotransferases", issued as U.S. Pat. No. 5,962,283 the disclosure of which is incorporated herein by reference in its entirety, one can convert the transaminases of the invention to use D-amino acids as substrates. Such conversion makes possible a broader array of transaminase applications. For instance, D-valine can be used in the manufacture of synthetic pyrethroids. D-phenylglycine and its derivatives can be useful as components of β-lactam antibiotics. Further, the thermostable transaminases have superior stability at higher temperatures and in organic solvents. Thus, they are better suited to utilize either L- and/or D-amino acids for production of optically pure chiral compounds used in pharmaceutical, agricultural, and other chemical manufactures.

There are a number of reasons to employ transaminases in industrial-scale production of amino acids and their derivatives.

1) Transaminases can catalyze stereoselective synthesis of D- or L-amino acids from their corresponding α-keto acids. Therefore no L- or D-isomers are produced, and no resolution is required.

2) Transaminases have uniformly high catalytic rates, capable of converting up to 400 μmoles of substrates per minute per mg enzyme.

3) Many required α-keto acids can be conveniently prepared by chemical synthesis at low cost.

4) The capital investment for an immobilized enzyme process using transaminases is much lower than for a large scale fermentation process, and productivity of the bioreactor is often an order of magnitude higher.

5) The technology is generally applicable to a broad range of D- or L-amino acids because transaminases exist with varying specificities. Such broad scope allows a number of different L- or D-amino acids to be produced with the same equipment and often the same biocatalyst.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against an enzyme of the present invention may be used in screening for similar enzymes from other organisms and samples. Such screening techniques are known in the art, for example, one such screening assay is described in Sambrook and Maniatis, Molecular Cloning: A Laboratory Manual (2d Ed.), vol. 2:Section 8.49, Cold Spring Harbor Laboratory, 1989, which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

EXAMPLE 1

Bacterial Expression and Purification of Transaminases and Aminotransferases

DNA encoding the enzymes of the present invention, SEQ ID NOS:25 through 32, were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The genomic DNA has also been used as a template for the PCR amplification, i.e., once a positive clone has been identified and primer sequences determined using the cDNA, it was then possible to return to the genomic DNA and directly amplify the desired sequence(s) there. The 5' and 3' primer sequences and the vector for the respective genes are as follows:

Aquifex Aspartate Transaminase A
aspa501 5' CCGAGAATTCATTAAAGAGGAGAAAT-TAACTATGATTGAAGACCCTATGGAC (SEQ. ID NO:1)
aspa301 3' CGAAGATCTTTAGCACTTCTCTCAGGTTC (SEQ. ID NO:2)
vector: pQET1
Aquifex Aspartate Aminotransferase B
aspb501 5' CCGAGAATTCATTAAAGAGGAGAAAT-TAACTATGGACAGGCTTGAAAAAGTA (SEQ ID NO:3)
aspb301 3' CGGAAGATCTTCAGCTAAGCTTCTCTAA-GAA (SEQ ID NO:4)
vector: pQET1
Aquifex Adenosyl-8-amino7oxononanoate Aminotransferase
ameth501 5' CCGACAATTGATTAAAGAGGAGAAAT-TAACTATGTGGGAATTAGACCCTAAA (SEQ ID NO:5)
ameth301 3' CGGAGGATCCCTACAC-CTCTTTTTCAAGCT (SEQ ID NO:6)
vector: pQET12
Aquifex Acetylornithine Aminotransferase
aorn 501 5' CCGACAATTGATTAAAGAGGAGAAAT-TAACTATGACATACTTAATGAACAAT (SEQ ID NO:7)
aorn 301 3' CGGAAGATCTTRATGAGAAGTC-CCTTTCAAG (SEQ ID NO:8)
vector: pQET12
*Ammonifex degensii* Aspartate Aminotransferase
adasp 501 5' CCGAGAATTCATTAAAGAGGAGAAAT-TAACTATGCGGAAACTGGCCGAGCGG (SEQ ID NO:9)
adasp 301 3' CGGAGGATCCTTAAAGTGCCGCTTC-GATCAA (SEQ ID NO:10)
vector: pQET12
Aquifex Glucosamine:Fructose6-phosphate Aminotransferase
glut 501 5' CCGACAATTGATTAAAGAGGAGAAAT-TAACTATGTGCGGGATAGTCGGATAC (SEQ ID NO:11)
glut 301 3' CGGAAGATCTTRATTCCACCGTGAC-CGTTTT (SEQ ID NO: 12)
vector: pQET1
Aquifex Histadine-phosphate Aminotransferase
his 501 5' CCGACAATTGATTAAATACCCCAGAG-GATTAAG (SEQ ID NO: 13)
his 301 3' CGGAAGATCMAAAGAGAGCT-TGAAAGGGA (SEQ ID NO: 14)
vector: pQET1
*Pyrobacullum aerophilum* Branched Chain Aminotransferase
bcat 501 5' CCGAGAATTCATTAAAGAGGAGAAAT-TAACTATGAAGCCGTACGCTAAATAT (SEQ ID NO:15)
bcat 301 3' CGGAAGATCTCTAATACACAGGAGT-GATCCA (SEQ ID NO:16)
vector: pQET1
*Ammonifex degensii* hp aminotransferase.
5' -CCGAGAATTCATTAAAGAGGAGAAATTAACTAT-GGCAGTCAAAGTGCGGCCT (SEQ ID NO:41)
3' -CGGAGGATCCTTATCCAAAGCTTCCAGGAAG (SEQ ID NO:42)
Homology information:
Closest to Bacillus subtilis (reference: Henner D. J., Band L., Flaggs G., Chen E.; Gene 49:147–152(1986). Percent Similarity: 65.084 Percent Identity: 44.134
Aquifex aspartate aminotransferase
5' CCGAGAATTCATTAAAGAGGAGAAAT-TAACTATGAGAAAGGACTTGCAAGT (SEQ ID NO:43)

3' CGGAGGATCCTTAGATCTCTTCAAGGGCTTT (SEQ ID NO:44)

Closest to *Bacillus subtilis* (Sorokin, A. V., Azevedo, V., Zumstein, E., Galleron, N., Ehrlich, S. D. and Serror, P. Determination and analysis of the nucleotide sequence of the *Bacillus subtilis* chromosome region between serA and kdg loci cloned in yeast artificial chromosome Unpublished (1995). Percent Similarity: 71.611 Percent Identity: 52.685

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp$^r$), a bacterial origin of replication (ori), an IPTG-regulatable promoter operator (P/O), a ribosome binding site (RBS), a 6-His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the *E. coli* strain M15/pREP4 (Qiagen, Inc.) by electroporation. M15/pREP4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

EXAMPLE 2

Isolation of a Selected Clone from the Deposited Genomic Clones

The two oligonucleotide primers corresponding to the gene of interest are used to amplify the gene from the deposited material. A polymerase chain reaction is carried out in 25 $\mu$l of reaction mixture with 0.1 $\mu$g of the DNA of the gene of interest. The reaction mixture is 1.5–5 mM MgCl$_2$, 0.01% (w/v) gelatin, 20 $\mu$M each of dATP, dCTP, dGTP, dTTP, 25 pmol of each primer and 1.25 Unit of Taq polymerase. Thirty cycles of PCR (denaturation at 94° C. for 1 min; annealing at 55° C. for 1 min; elongation at 72° C. for 1 min) are performed with the Perkin-Elmer Cetus 9600 thermal cycler. The amplified product is analyzed by agarose gel electrophoresis and the DNA band with expected molecular weight is excised and purified. The PCR product is verified to be the gene of interest by subcloning and sequencing the DNA product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a member selected from the group consisting of:
   (a) a polynucleotide having at least a 70% identity to a polynucleotide encoding an enzyme comprising amino acid sequences set forth in SEQ ID NOs: 25–32, and which encodes an enzyme having aminotransferase and/or transaminase activity and, degenerate variants thereof; and
   (b) a polynucleotide which is complementary to the polynucleotide of (a).

2. The polynucleotide of claim 1 wherein the polynucleotide is DNA.

3. The polynucleotide of claim 1 wherein the polynucleotide is RNA.

4. A vector comprising the DNA of claim 2.

5. A host cell comprising the vector of claim 4.

6. A process for producing a polypeptide comprising expressing from the host cell of claim 5 a polypeptide encoded by said DNA.

7. A process for producing a cell comprising transforming or transfecting the cell with the vector of claim 4 such that the cell expresses the polypeptide encoded by the DNA contained in the vector.

8. An enzyme comprising an amino acid sequence which is at least 70% identical to the amino acid sequence set forth in SEQ ID NOs: 25–32, and having aminotransferase and/or transaminase activity.

9. A method for transferring an amino group from an amino acid to an α-keto acid comprising:
   contacting an amino acid in the presence of an α-keto acid with an enzyme selected from the group consisting of an enzyme having the amino acid sequence set forth in SEQ ID NOs: 25–32, or an amino acid which is at least 70% identical to an amino acid sequence set forth in SEQ ID NOs: 25–32, and which has aminotransferase and/or transaminase activity.

10. A polynucleotide of claim 1, wherein the sequence is set forth in SEQ ID NOs: 17–24 or sequences having at least 70% identity to SEQ ID NOs: 17–24.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CCGAGAATTC ATTAAAGAGG AGAAATTAAC TATGATTGAA GACCCTATGG AC    52

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CGGAAGATCT TTAAGCACTT CTCTCAGGTT C    31

(2) INFORMATION FOR SEQ ID NO:3:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CCGAGAATTC ATTAAAGAGG AGAAATTAAC TATGGACAGG CTTGAAAAAG TA          52
```

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CGGAAGATCT TCAGCTAAGC TTCTCTAAGA A                                 31
```

(2) INFORMATION FOR SEQ ID NO:5:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CCGACAATTG ATTAAAGAGG AGAAATTAAC TATGTGGGAA TTAGACCCTA AA          52
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CGGAGGATCC CTACACCTGT TTTTCAAGCT C                                 31
```

(2) INFORMATION FOR SEQ ID NO:7:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CCGACAATTG ATTAAAGAGG AGAAATTAAC TATGACATAC TTAATGAACA AT          52
```

(2) INFORMATION FOR SEQ ID NO:8:

(i) SEQUENCE CHARACTERISTICS:

```
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CGGAAGATCT TTATGAGAAG TCCCTTTCAA G                                           31

(2) INFORMATION FOR SEQ ID NO:9:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

CCGAGAATTC ATTAAAGAGG AGAAATTAAC TATGCGGAAA CTGGCCGAGC GG                    52

(2) INFORMATION FOR SEQ ID NO:10:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

CGGAGGATCC TTAAAGTGCC GCTTCGATCA A                                           31

(2) INFORMATION FOR SEQ ID NO:11:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

CCGACAATTG ATTAAAGAGG AGAAATTAAC TATGTGCGGG ATAGTCGGAT AC                    52

(2) INFORMATION FOR SEQ ID NO:12:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CGGAAGATCT TTATTCCACC GTGACCGTTT T                                           31

(2) INFORMATION FOR SEQ ID NO:13:

(i) SEQUENCE CHARACTERISTICS:
            (A) LENGTH: 52 base pairs
            (B) TYPE: nucleic acid
            (C) STRANDEDNESS: single
            (D) TOPOLOGY: linear
```

(ii) MOLECULE TYPE: cDNA (xi) SEQUENCE DESCRIPTION: SEQ ID NO:13:

CCGACAATTG ATTAAAGAGG AGAAATTAAC TATGATACCC CAGAGGATTA AG          52

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGGAAGATCT TTAAAGAGAG CTTGAAAGGG A                                 31

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCGAGAATTC ATTAAAGAGG AGAAATTAAC TATGAAGCCG TACGCTAAAT AT          52

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CGGAAGATCT CTAATACACA GGAGTGATCC A                                 31

(2) INFORMATION FOR SEQ ID NO:17:

(i) SEQUENCE CHARACTERISTICS:
        (A) LENGTH: 1245 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1242

(xi) SEQUENCE DESCRIPTION: SEQ ID NO:17:

ATG ATT GAA GAC CCT ATG GAC TGG GCT TTT CCG AGG ATA AAG AGA CTG    48
Met Ile Glu Asp Pro Met Asp Trp Ala Phe Pro Arg Ile Lys Arg Leu
 1               5                  10                  15

CCT CAG TAT GTC TTC TCT CTC GTT AAC GAA CTC AAG TAC AAG CTA AGG    96
Pro Gln Tyr Val Phe Ser Leu Val Asn Glu Leu Lys Tyr Lys Leu Arg
                20                  25                  30

CGT GAA GGC GAA GAT GTA GTG GAT CTT GGT ATG GGC AAT CCT AAC ATG   144
Arg Glu Gly Glu Asp Val Val Asp Leu Gly Met Gly Asn Pro Asn Met

```
              35                    40                    45
CCT CCA GCA AAG CAC ATA ATA GAT AAA CTC TGC GAA GTG GCT CAA AAG       192
Pro Pro Ala Lys His Ile Ile Asp Lys Leu Cys Glu Val Ala Gln Lys
        50                  55                  60

CCG AAC GTT CAC GGA TAT TCT GCG TCA AGG GGC ATA CCA AGA CTG AGA       240
Pro Asn Val His Gly Tyr Ser Ala Ser Arg Gly Ile Pro Arg Leu Arg
65                  70                  75                  80

AAG GCT ATA TGT AAC TTC TAC GAA GAA AGG TAC GGA GTG AAA CTC GAC       288
Lys Ala Ile Cys Asn Phe Tyr Glu Glu Arg Tyr Gly Val Lys Leu Asp
                85                  90                  95

CCT GAG AGG GAG GCT ATA CTA ACA ATC GGT GCA AAG GAA GGG TAT TCT       336
Pro Glu Arg Glu Ala Ile Leu Thr Ile Gly Ala Lys Glu Gly Tyr Ser
            100                 105                 110

CAT TTG ATG CTT GCG ATG ATA TCT CCG GGT GAT ACG GTA ATA GTT CCT       384
His Leu Met Leu Ala Met Ile Ser Pro Gly Asp Thr Val Ile Val Pro
        115                 120                 125

AAT CCC ACC TAT CCT ATT CAC TAT TAC GCT CCC ATA ATT GCA GGA GGG       432
Asn Pro Thr Tyr Pro Ile His Tyr Tyr Ala Pro Ile Ile Ala Gly Gly
    130                 135                 140

GAA GTT CAC TCA ATA CCC CTT AAC TTC TCG GAC GAT CAA GAT CAT CAG       480
Glu Val His Ser Ile Pro Leu Asn Phe Ser Asp Asp Gln Asp His Gln
145                 150                 155                 160

GAA GAG TTT TTA AGG AGG CTT TAC GAG ATA GTA AAA ACC GCG ATG CCA       528
Glu Glu Phe Leu Arg Arg Leu Tyr Glu Ile Val Lys Thr Ala Met Pro
                165                 170                 175

AAA CCC AAG GCT GTC GTC ATA AGC TTT CCT CAC AAT CCA ACG ACC ATA       576
Lys Pro Lys Ala Val Val Ile Ser Phe Pro His Asn Pro Thr Thr Ile
            180                 185                 190

ACG GTA GAA AAG GAC TTT TTT AAA GAA ATA GTT AAG TTT GCA AAG GAA       624
Thr Val Glu Lys Asp Phe Phe Lys Glu Ile Val Lys Phe Ala Lys Glu
        195                 200                 205

CAC GGT CTC TGG ATA ATA CAC GAT TTT GCG TAT GCG GAT ATA GCC TTT       672
His Gly Leu Trp Ile Ile His Asp Phe Ala Tyr Ala Asp Ile Ala Phe
    210                 215                 220

GAC GGT TAC AAG CCC CCC TCA ATA CTC GAA ATA GAA GGT GCT AAA GAC       720
Asp Gly Tyr Lys Pro Pro Ser Ile Leu Glu Ile Glu Gly Ala Lys Asp
225                 230                 235                 240

GTT GCG GTT GAG CTC TAC TCC ATG TCA AAG GGC TTT TCA ATG GCG GGC       768
Val Ala Val Glu Leu Tyr Ser Met Ser Lys Gly Phe Ser Met Ala Gly
                245                 250                 255

TGG AGG GTA GCC TTT GTC GTT GGA AAC GAA ATA CTC ATA AAA AAC CTT       816
Trp Arg Val Ala Phe Val Val Gly Asn Glu Ile Leu Ile Lys Asn Leu
            260                 265                 270

GCA CAC CTC AAA AGC TAC TTG GAT TAC GGT ATA TTT ACT CCC ATA CAG       864
Ala His Leu Lys Ser Tyr Leu Asp Tyr Gly Ile Phe Thr Pro Ile Gln
        275                 280                 285

GTG GCC TCT ATT ATC GCA TTA GAG AGC CCC TAC GAA ATC GTG GAA AAA       912
Val Ala Ser Ile Ile Ala Leu Glu Ser Pro Tyr Glu Ile Val Glu Lys
    290                 295                 300

ACC GCA AAG GTT TAC CAA AAA AGA AGA GAC GTT CTG GTG GAA GGG TTA       960
Thr Ala Lys Val Tyr Gln Lys Arg Arg Asp Val Leu Val Glu Gly Leu
305                 310                 315                 320

AAC AGG CTC GGC TGG AAA GTA AAA AAA CCT AAG GCT ACC ATG TTC GTC      1008
Asn Arg Leu Gly Trp Lys Val Lys Lys Pro Lys Ala Thr Met Phe Val
                325                 330                 335

TGG GCA AAG ATT CCC GAA TGG ATA AAT ATG AAC TCT CTG GAC TTT TCC      1056
Trp Ala Lys Ile Pro Glu Trp Ile Asn Met Asn Ser Leu Asp Phe Ser
            340                 345                 350

TTG TTC CTC CTA AAA GAG GCG AAG GTT GCG GTA TCC CCG GGT GTG GGC      1104
```

```
Leu Phe Leu Leu Lys Glu Ala Lys Val Ala Val Ser Pro Gly Val Gly
        355                 360                 365

TTT GGT CAG TAC GGA GAG GGG TAC GTA AGG TTT GCA CTT GTA GAA AAT        1152
Phe Gly Gln Tyr Gly Glu Gly Tyr Val Arg Phe Ala Leu Val Glu Asn
        370                 375                 380

GAA CAC AGG ATC AGA CAG GCT ATA AGG GGA ATA AGG AAA GCC TTC AGA        1200
Glu His Arg Ile Arg Gln Ala Ile Arg Gly Ile Arg Lys Ala Phe Arg
385                 390                 395                 400

AAA CTC CAG AAG GAG AGG AAA CTT GAA CCT GAG AGA AGT GCT TAA            1245
Lys Leu Gln Lys Glu Arg Lys Leu Glu Pro Glu Arg Ser Ala
                405                 410

(2) INFORMATION FOR SEQ ID NO:18:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1119

(xi) SEQUENCE DESCRIPTION: SEQ ID NO:18:

ATG GAC AGG CTT GAA AAA GTA TCA CCC TTC ATA GTA ATG GAT ATC CTA          48
Met Asp Arg Leu Glu Lys Val Ser Pro Phe Ile Val Met Asp Ile Leu
1                   5                  10                  15

GCT CAG GCC CAG AAG TAC GAA GAC GTA GTA CAC ATG GAG ATA GGA GAG          96
Ala Gln Ala Gln Lys Tyr Glu Asp Val Val His Met Glu Ile Gly Glu
                20                  25                  30

CCC GAT TTA GAA CCG TCT CCC AAG GTA ATG GAA GCT CTG GAA CGT GCG         144
Pro Asp Leu Glu Pro Ser Pro Lys Val Met Glu Ala Leu Glu Arg Ala
            35                  40                  45

GTG AAG GAA AAG ACG TTC TTC TAC ACC CCT GCT CTG GGA CTC TGG GAA         192
Val Lys Glu Lys Thr Phe Phe Tyr Thr Pro Ala Leu Gly Leu Trp Glu
50                  55                  60

CTC AGG GAA AGG ATA TCG GAG TTT TAC AGG AAA AAG TAC AGC GTT GAA         240
Leu Arg Glu Arg Ile Ser Glu Phe Tyr Arg Lys Lys Tyr Ser Val Glu
65                  70                  75                  80

GTT TCT CCA GAG AGA GTC ATC GTA ACT ACC GGA ACT TCG GGA GCG TTT         288
Val Ser Pro Glu Arg Val Ile Val Thr Thr Gly Thr Ser Gly Ala Phe
                85                  90                  95

CTC GTA GCC TAC GCC GTA ACA CTA AAT GCG GGA GAG AAG ATA ATC CTC         336
Leu Val Ala Tyr Ala Val Thr Leu Asn Ala Gly Glu Lys Ile Ile Leu
            100                 105                 110

CCA GAC CCC TCT TAC CCC TGT TAC AAA AAC TTT GCC TAC CTC TTA GAC         384
Pro Asp Pro Ser Tyr Pro Cys Tyr Lys Asn Phe Ala Tyr Leu Leu Asp
        115                 120                 125

GCT CAG CCG GTT TTC GTA AAC GTT GAC AAG GAA ACG AAT TAC GAA GTA         432
Ala Gln Pro Val Phe Val Asn Val Asp Lys Glu Thr Asn Tyr Glu Val
130                 135                 140

AGG AAA GAG ATG ATA GAA GAC ATT GAT GCG AAA GCC CTT CAC ATT TCC         480
Arg Lys Glu Met Ile Glu Asp Ile Asp Ala Lys Ala Leu His Ile Ser
145                 150                 155                 160

TCG CCT CAA AAC CCT ACG GGC ACA CTC TAC TCA CCT GAA ACC CTG AAG         528
Ser Pro Gln Asn Pro Thr Gly Thr Leu Tyr Ser Pro Glu Thr Leu Lys
                165                 170                 175

GAA CTT GCG GAG TAC TGC GAA GAG AAG GGT ATG TAC TTC ATA TCC GAC         576
Glu Leu Ala Glu Tyr Cys Glu Glu Lys Gly Met Tyr Phe Ile Ser Asp
            180                 185                 190
```

```
GAG ATT TAC CAC GGA CTC GTT TAC GAA GGT AGG GAG CAC ACA GCA CTT        624
Glu Ile Tyr His Gly Leu Val Tyr Glu Gly Arg Glu His Thr Ala Leu
        195                 200                 205

GAG TTC TCT GAC AGG GCT ATT GTC ATA AAC GGG TTT TCT AAG TAC TTC        672
Glu Phe Ser Asp Arg Ala Ile Val Ile Asn Gly Phe Ser Lys Tyr Phe
    210                 215                 220

TGT ATG CCA GGT TTC AGG ATA GGG TGG ATG ATA GTT CCG GAA GAA CTC        720
Cys Met Pro Gly Phe Arg Ile Gly Trp Met Ile Val Pro Glu Glu Leu
225                 230                 235                 240

GTG AGA AAG GCG GAA ATA GTA ATT CAG AAC GTA TTT ATA TCT GCC CCG        768
Val Arg Lys Ala Glu Ile Val Ile Gln Asn Val Phe Ile Ser Ala Pro
                245                 250                 255

ACG CTC AGT CAG TAC GCC GCC CTT GAG GCT TTT GAT TAC GAG TAT TTG        816
Thr Leu Ser Gln Tyr Ala Ala Leu Glu Ala Phe Asp Tyr Glu Tyr Leu
            260                 265                 270

GAG AAG GTA AGA AAA ACC TTT GAA GAG AGG AGG AAC TTC CTT TAT GGG        864
Glu Lys Val Arg Lys Thr Phe Glu Glu Arg Arg Asn Phe Leu Tyr Gly
        275                 280                 285

GAA CTG AAA AAA CTC TTC AAG ATA GAC GCG AAA CCT CAG GGA GCT TTT        912
Glu Leu Lys Lys Leu Phe Lys Ile Asp Ala Lys Pro Gln Gly Ala Phe
    290                 295                 300

TAC GTA TGG GCA AAC ATA AGT GAT TAC TCC ACA GAT AGC TAC GAA TTT        960
Tyr Val Trp Ala Asn Ile Ser Asp Tyr Ser Thr Asp Ser Tyr Glu Phe
305                 310                 315                 320

GCT TTA AAA CTT TTA AGG GAG GCG AGG GTG GCG GTA ACG CCC GGG GTG       1008
Ala Leu Lys Leu Leu Arg Glu Ala Arg Val Ala Val Thr Pro Gly Val
                325                 330                 335

GAC TTT GGA AAA AAC AAA ACG AAG GAG TAT ATA AGG TTT GCT TAT ACG       1056
Asp Phe Gly Lys Asn Lys Thr Lys Glu Tyr Ile Arg Phe Ala Tyr Thr
            340                 345                 350

AGA AAG ATA GAA GAA CTT AAG GAG GGC GTT GAA AGG ATA AAG AAG TTC       1104
Arg Lys Ile Glu Glu Leu Lys Glu Gly Val Glu Arg Ile Lys Lys Phe
        355                 360                 365

TTA GAG AAG CTT AGC TGA                                               1122
Leu Glu Lys Leu Ser
    370
```

(2) INFORMATION FOR SEQ ID NO:19:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1359

(xi) SEQUENCE DESCRIPTION: SEQ ID NO:19:

```
ATG TGG GAA TTA GAC CCT AAA ACG CTC GAA AAG TGG GAC AAG GAG TAC         48
Met Trp Glu Leu Asp Pro Lys Thr Leu Glu Lys Trp Asp Lys Glu Tyr
1                   5                  10                  15

TTC TGG CAT CCA TTT ACC CAG ATG AAA GTC TAC AGA GAA GAA GAA AAC         96
Phe Trp His Pro Phe Thr Gln Met Lys Val Tyr Arg Glu Glu Glu Asn
                20                  25                  30

CTG ATA TTT GAA CGC GGA GAA GGC GTT TAC CTG TGG GAC ATA TAC GGC        144
Leu Ile Phe Glu Arg Gly Glu Gly Val Tyr Leu Trp Asp Ile Tyr Gly
            35                  40                  45

AGG AAG TAT ATA GAT GCC ATA TCT TCC CTC TGG TGC AAC GTC CAC GGA        192
```

```
                                                         -continued

Arg Lys Tyr Ile Asp Ala Ile Ser Ser Leu Trp Cys Asn Val His Gly
 50                  55                  60

CAT AAC CAC CCT AAA CTG AAC AAC GCA GTT ATG AAA CAG CTC TGT AAG         240
His Asn His Pro Lys Leu Asn Asn Ala Val Met Lys Gln Leu Cys Lys
 65                  70                  75                  80

GTA GCT CAC ACA ACT ACT CTG GGA AGT TCC AAC GTT CCC GCC ATA CTC         288
Val Ala His Thr Thr Thr Leu Gly Ser Ser Asn Val Pro Ala Ile Leu
                     85                  90                  95

CTT GCA AAG AAG CTT GTA GAA ATT TCT CCT GAA GGA TTA AAC AAG GTC         336
Leu Ala Lys Lys Leu Val Glu Ile Ser Pro Glu Gly Leu Asn Lys Val
                100                 105                 110

TTT TAC TCC GAA GAC GGT GCG GAA GCA GTA GAG ATA GCG ATA AAG ATG         384
Phe Tyr Ser Glu Asp Gly Ala Glu Ala Val Glu Ile Ala Ile Lys Met
            115                 120                 125

GCT TAT CAC TAC TGG AAG AAC AAG GGA GTT AAA GGG AAA AAC GTT TTC         432
Ala Tyr His Tyr Trp Lys Asn Lys Gly Val Lys Gly Lys Asn Val Phe
        130                 135                 140

ATA ACG CTT TCC GAA GCC TAC CAC GGG GAT ACT GTA GGA GCG GTT AGC         480
Ile Thr Leu Ser Glu Ala Tyr His Gly Asp Thr Val Gly Ala Val Ser
145                 150                 155                 160

GTA GGG GGT ATA GAA CTC TTC CAC GGA ACT TAT AAA GAT CTC CTT TTC         528
Val Gly Gly Ile Glu Leu Phe His Gly Thr Tyr Lys Asp Leu Leu Phe
                165                 170                 175

AAG ACT ATA AAA CTC CCA TCT CCT TAC CTG TAC TGC AAG GAA AAG TAC         576
Lys Thr Ile Lys Leu Pro Ser Pro Tyr Leu Tyr Cys Lys Glu Lys Tyr
            180                 185                 190

GGG GAA CTC TGC CCT GAG TGC ACG GCA GAT TTA TTA AAA CAA CTG GAA         624
Gly Glu Leu Cys Pro Glu Cys Thr Ala Asp Leu Leu Lys Gln Leu Glu
        195                 200                 205

GAT ATC CTG AAG TCG CGG GAA GAT ATC GTT GCG GTC ATT ATG GAA GCG         672
Asp Ile Leu Lys Ser Arg Glu Asp Ile Val Ala Val Ile Met Glu Ala
210                 215                 220

GGA ATT CAG GCA GCC GCG GGA ATG CTC CCC TTC CCT CCG GGA TTT TTG         720
Gly Ile Gln Ala Ala Ala Gly Met Leu Pro Phe Pro Pro Gly Phe Leu
225                 230                 235                 240

AAA GGC GTA AGG GAG CTT ACG AAG AAA TAC GAC ACT TTA ATG ATA GTT         768
Lys Gly Val Arg Glu Leu Thr Lys Lys Tyr Asp Thr Leu Met Ile Val
                245                 250                 255

GAC GAG GTT GCC ACG GGA TTT GGC AGG ACG GGA ACG ATG TTT TAC TGT         816
Asp Glu Val Ala Thr Gly Phe Gly Arg Thr Gly Thr Met Phe Tyr Cys
            260                 265                 270

GAG CAG GAA GGA GTC AGT CCG GAC TTT ATG TGT CTA GGT AAG GGT ATA         864
Glu Gln Glu Gly Val Ser Pro Asp Phe Met Cys Leu Gly Lys Gly Ile
        275                 280                 285

ACC GGA GGG TAC CTC CCG CTT GCT GCG ACA CTC ACA ACG GAC GAG GTG         912
Thr Gly Gly Tyr Leu Pro Leu Ala Ala Thr Leu Thr Thr Asp Glu Val
290                 295                 300

TTC AAT GCC TTT TTA GGT GAG TTC GGG GAG GCA AAG CAC TTT TAC CAC         960
Phe Asn Ala Phe Leu Gly Glu Phe Gly Glu Ala Lys His Phe Tyr His
305                 310                 315                 320

GGG CAC ACC TAC ACT GGA AAT AAC CTC GCC TGT TCC GTT GCA CTC GCA        1008
Gly His Thr Tyr Thr Gly Asn Asn Leu Ala Cys Ser Val Ala Leu Ala
                325                 330                 335

AAC TTA GAA GTT TTT GAG GAA GAA AGA ACT TTA GAG AAG CTC CAA CCA        1056
Asn Leu Glu Val Phe Glu Glu Glu Arg Thr Leu Glu Lys Leu Gln Pro
            340                 345                 350

AAG ATA AAG CTT TTA AAG GAA AGG CTT CAG GAG TTC TGG GAA CTC AAG        1104
Lys Ile Lys Leu Leu Lys Glu Arg Leu Gln Glu Phe Trp Glu Leu Lys
        355                 360                 365
```

-continued

```
CAC GTT GGA GAT GTT AGA CAG CTA GGT TTT ATG GCT GGA ATA GAG CTG        1152
His Val Gly Asp Val Arg Gln Leu Gly Phe Met Ala Gly Ile Glu Leu
    370                 375                 380

GTG AAG GAC AAA GAA AAG GGA GAA CCT TTC CCT TAC GGT GAA AGG ACG        1200
Val Lys Asp Lys Glu Lys Gly Glu Pro Phe Pro Tyr Gly Glu Arg Thr
385                 390                 395                 400

GGA TTT AAG GTG GCT TAC AAG TGC AGG GAA AAA GGG GTG TTT TTG AGA        1248
Gly Phe Lys Val Ala Tyr Lys Cys Arg Glu Lys Gly Val Phe Leu Arg
                405                 410                 415

CCG CTC GGA GAC GTT ATG GTA TTG ATG ATG CCT CTT GTA ATA GAG GAA        1296
Pro Leu Gly Asp Val Met Val Leu Met Met Pro Leu Val Ile Glu Glu
            420                 425                 430

GAC GAA ATG AAC TAC GTT ATT GAT ACA CTT AAA TGG GCA ATT AAA GAG        1344
Asp Glu Met Asn Tyr Val Ile Asp Thr Leu Lys Trp Ala Ile Lys Glu
        435                 440                 445

CTT GAA AAA GAG GTG TAG                                                1362
Leu Glu Lys Glu Val
    450
```

(2) INFORMATION FOR SEQ ID NO:20:

(i) SEQUENCE CHARACTERISTICS:
(A) LENGTH: 1032 base pairs
(B) TYPE: nucleic acid
(C) STRANDEDNESS: single
(D) TOPOLOGY: linear (ii) MOLECULE TYPE: Genomic DNA (ix) FEATURE:
(A) NAME/KEY: Coding Sequence
(B) LOCATION: 1...1029

(xi) SEQUENCE DESCRIPTION: SEQ ID NO:20:

```
ATG ACA TAC TTA ATG AAC AAT TAC GCA AGG TTG CCC GTA AAG TTT GTA          48
Met Thr Tyr Leu Met Asn Asn Tyr Ala Arg Leu Pro Val Lys Phe Val
1               5                   10                  15

AGG GGA AAA GGT GTT TAC CTG TAC GAT GAG GAA GGA AAG GAG TAT CTT          96
Arg Gly Lys Gly Val Tyr Leu Tyr Asp Glu Glu Gly Lys Glu Tyr Leu
            20                  25                  30

GAC TTT GTC TCC GGT ATA GGC GTC AAC TCC CTC GGT CAC GCT TAC CCA         144
Asp Phe Val Ser Gly Ile Gly Val Asn Ser Leu Gly His Ala Tyr Pro
        35                  40                  45

AAA CTC ACA GAA GCT CTA AAA GAA CAG GTT GAG AAA CTC CTC CAC GTT         192
Lys Leu Thr Glu Ala Leu Lys Glu Gln Val Glu Lys Leu Leu His Val
    50                  55                  60

TCA AAT CTT TAC GAA AAC CCG TGG CAG GAA GAA CTG GCT CAC AAA CTT         240
Ser Asn Leu Tyr Glu Asn Pro Trp Gln Glu Glu Leu Ala His Lys Leu
65                  70                  75                  80

GTA AAA CAC TTC TGG ACA GAA GGG AAG GTA TTT TTC GCA AAC AGC GGA         288
Val Lys His Phe Trp Thr Glu Gly Lys Val Phe Phe Ala Asn Ser Gly
                85                  90                  95

ACG GAA AGT GTA GAG GCG GCT ATA AAG CTC GCA AGG AAG TAC TGG AGG         336
Thr Glu Ser Val Glu Ala Ala Ile Lys Leu Ala Arg Lys Tyr Trp Arg
            100                 105                 110

GAT AAA GGA AAG AAC AAG TGG AAG TTT ATA TCC TTT GAA AAC TCT TTC         384
Asp Lys Gly Lys Asn Lys Trp Lys Phe Ile Ser Phe Glu Asn Ser Phe
        115                 120                 125

CAC GGG AGA ACC TAC GGT AGC CTC TCC GCA ACG GGA CAG CCA AAG TTC         432
His Gly Arg Thr Tyr Gly Ser Leu Ser Ala Thr Gly Gln Pro Lys Phe
    130                 135                 140

CAC AAA GGC TTT GAA CCT CTA GTT CCT GGA TTT TCT TAC GCA AAG CTG         480
His Lys Gly Phe Glu Pro Leu Val Pro Gly Phe Ser Tyr Ala Lys Leu
```

```
                 145                 150                 155                 160
AAC GAT ATA GAC AGC GTT TAC AAA CTC CTA GAC GAG GAA ACC GCG GGG       528
Asn Asp Ile Asp Ser Val Tyr Lys Leu Leu Asp Glu Glu Thr Ala Gly
                165                 170                 175

ATA ATT ATT GAA GTT ATA CAA GGA GAG GGC GGA GTA AAC GAG GCG AGT       576
Ile Ile Ile Glu Val Ile Gln Gly Glu Gly Gly Val Asn Glu Ala Ser
                180                 185                 190

GAG GAT TTT CTA AGT AAA CTC CAG GAA ATT TGT AAA GAA AAA GAT GTG       624
Glu Asp Phe Leu Ser Lys Leu Gln Glu Ile Cys Lys Glu Lys Asp Val
                195                 200                 205

CTC TTA ATT ATA GAC GAA GTG CAA ACG GGA ATA GGA AGG ACC GGG GAA       672
Leu Leu Ile Ile Asp Glu Val Gln Thr Gly Ile Gly Arg Thr Gly Glu
                210                 215                 220

TTC TAC GCA TAT CAA CAC TTC AAT CTA AAA CCG GAC GTA ATT GCG CTT       720
Phe Tyr Ala Tyr Gln His Phe Asn Leu Lys Pro Asp Val Ile Ala Leu
225                 230                 235                 240

GCG AAG GGA CTC GGA GGA GGT GTG CCA ATA GGT GCC ATC CTT GCA AGG       768
Ala Lys Gly Leu Gly Gly Gly Val Pro Ile Gly Ala Ile Leu Ala Arg
                245                 250                 255

GAA GAA GTG GCC CAG AGC TTT ACT CCC GGC TCC CAC GGC TCT ACC TTC       816
Glu Glu Val Ala Gln Ser Phe Thr Pro Gly Ser His Gly Ser Thr Phe
                260                 265                 270

GGA GGA AAC CCC TTA GCC TGC AGG GCG GGA ACA GTG GTA GTA GAT GAA       864
Gly Gly Asn Pro Leu Ala Cys Arg Ala Gly Thr Val Val Val Asp Glu
                275                 280                 285

GTT GAA AAA CTC CTG CCT CAC GTA AGG GAA GTG GGG AAT TAC TTC AAA       912
Val Glu Lys Leu Leu Pro His Val Arg Glu Val Gly Asn Tyr Phe Lys
                290                 295                 300

GAA AAA CTG AAG GAA CTC GGC AAA GGA AAG GTA AAG GGA AGA GGA TTG       960
Glu Lys Leu Lys Glu Leu Gly Lys Gly Lys Val Lys Gly Arg Gly Leu
305                 310                 315                 320

ATG CTC GGT CTT GAA CTT GAA AGA GAG TGT AAA GAT TAC GTT CTC AAG      1008
Met Leu Gly Leu Glu Leu Glu Arg Glu Cys Lys Asp Tyr Val Leu Lys
                325                 330                 335

GCT CTT GAA AGG GAC TTC TCA TAA                                      1032
Ala Leu Glu Arg Asp Phe Ser
                340

(2) INFORMATION FOR SEQ ID NO:21:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1194

(xi) SEQUENCE DESCRIPTION: SEQ ID NO:21:

ATG CGG AAA CTG GCC GAG CGG GCG CAG AAA CTG AGC CCC TCT CCC ACC        48
Met Arg Lys Leu Ala Glu Arg Ala Gln Lys Leu Ser Pro Ser Pro Thr
1                   5                  10                  15

CTC TCG GTG GAC ACC AAG GCC AAG GAG CTT TTG CGG CAG GGG GAA AGG        96
Leu Ser Val Asp Thr Lys Ala Lys Glu Leu Leu Arg Gln Gly Glu Arg
                20                  25                  30

GTC ATC AAT TTC GGG GCG GGG GAG CCG GAC TTC GAT ACA CCG GAA CAC       144
Val Ile Asn Phe Gly Ala Gly Glu Pro Asp Phe Asp Thr Pro Glu His
                35                  40                  45
```

```
ATC AAG GAA GCG GCG AAG CGA GCT TTA GAT CAG GGC TTC ACC AAG TAC         192
Ile Lys Glu Ala Ala Lys Arg Ala Leu Asp Gln Gly Phe Thr Lys Tyr
        50                  55                  60

ACG CCG GTG GCT GGG ATC TTA CCT CTT CGG GAG GCC ATA TGC GAG AAG         240
Thr Pro Val Ala Gly Ile Leu Pro Leu Arg Glu Ala Ile Cys Glu Lys
 65                  70                  75                  80

CTT TAC CGC GAC AAT CAA CTG GAA TAC AGC CCG AAT GAG ATC GTG GTC         288
Leu Tyr Arg Asp Asn Gln Leu Glu Tyr Ser Pro Asn Glu Ile Val Val
                 85                  90                  95

TCC TGT GGC GCC AAG CAT TCT ATT TTC AAC GCT CTG CAG GTC CTC CTG         336
Ser Cys Gly Ala Lys His Ser Ile Phe Asn Ala Leu Gln Val Leu Leu
            100                 105                 110

GAC CCG GGG GAC GAG GTG ATA ATC CCC GTC CCC TAC TGG ACT TCC TAT         384
Asp Pro Gly Asp Glu Val Ile Ile Pro Val Pro Tyr Trp Thr Ser Tyr
            115                 120                 125

CCG GAG CAG GTG AAG CTG GCG GGA GGG GTG CCG GTT TTC GTC CCC ACC         432
Pro Glu Gln Val Lys Leu Ala Gly Gly Val Pro Val Phe Val Pro Thr
        130                 135                 140

TCT CCC GAG AAC GAC TTC AAG CTC AGG CCG GAA GAT CTA CGT GCG GCT         480
Ser Pro Glu Asn Asp Phe Lys Leu Arg Pro Glu Asp Leu Arg Ala Ala
145                 150                 155                 160

GTA ACC CCG CGC ACC CGC CTT TTG ATC CTC AAT TCC CCG GCC AAC CCC         528
Val Thr Pro Arg Thr Arg Leu Leu Ile Leu Asn Ser Pro Ala Asn Pro
                165                 170                 175

ACA GGC ACC GTT TAC CGC CGG GAG GAA CTT ATC GGC TTA GCG GAG GTA         576
Thr Gly Thr Val Tyr Arg Arg Glu Glu Leu Ile Gly Leu Ala Glu Val
            180                 185                 190

GCC CTG GAG GCC GAC CTA TGG ATC TTG TCG GAC GAG ATC TAC GAA AAG         624
Ala Leu Glu Ala Asp Leu Trp Ile Leu Ser Asp Glu Ile Tyr Glu Lys
        195                 200                 205

CTG ATC TAC GAC GGG ATG GAG CAC GTG AGC ATA GCC GCG CTC GAC CCG         672
Leu Ile Tyr Asp Gly Met Glu His Val Ser Ile Ala Ala Leu Asp Pro
    210                 215                 220

GAG GTC AAA AAG CGC ACG ATT GTG GTA AAC GGT GTT TCC AAG GCT TAC         720
Glu Val Lys Lys Arg Thr Ile Val Val Asn Gly Val Ser Lys Ala Tyr
225                 230                 235                 240

GCC ATG ACC GGT TGG CGC ATA GGT TAT GCT GCC GCT CCC CGG CCG ATA         768
Ala Met Thr Gly Trp Arg Ile Gly Tyr Ala Ala Ala Pro Arg Pro Ile
                245                 250                 255

GCC CAG GCC ATG ACC AAC CTC CAA AGC CAC AGT ACC TCT AAC CCC ACT         816
Ala Gln Ala Met Thr Asn Leu Gln Ser His Ser Thr Ser Asn Pro Thr
            260                 265                 270

TCC GTA GCC CAG GCG GCG GCG CTG GCC GCT CTG AAG GGG CCA CAA GAG         864
Ser Val Ala Gln Ala Ala Ala Leu Ala Ala Leu Lys Gly Pro Gln Glu
        275                 280                 285

CCG GTG GAG AAC ATG CGC CGG GCT TTT CAA AAG CGG CGG GAT TTC ATC         912
Pro Val Glu Asn Met Arg Arg Ala Phe Gln Lys Arg Arg Asp Phe Ile
    290                 295                 300

TGG CAG TAC CTA AAC TCC TTA CCC GGA GTG CGC TGC CCC AAA CCT TTA         960
Trp Gln Tyr Leu Asn Ser Leu Pro Gly Val Arg Cys Pro Lys Pro Leu
305                 310                 315                 320

GGG GCC TTT TAC GTC TTT CCA GAA GTT GAG CGG GCT TTT GGG CCG CCG        1008
Gly Ala Phe Tyr Val Phe Pro Glu Val Glu Arg Ala Phe Gly Pro Pro
                325                 330                 335

TCT AAA AGG ACG GGA AAT ACT ACC GCT AGC GAC CTG GCC CTT TTC CTC        1056
Ser Lys Arg Thr Gly Asn Thr Thr Ala Ser Asp Leu Ala Leu Phe Leu
            340                 345                 350

CTG GAA GAG ATA AAA GTG GCC ACC GTG GCT GGG GCT GCC TTT GGG GAC        1104
Leu Glu Glu Ile Lys Val Ala Thr Val Ala Gly Ala Ala Phe Gly Asp
        355                 360                 365
```

```
GAT CGC TAC CTG CGC TTT TCC TAC GCC CTG CGG CTG GAA GAT ATC GAA        1152
Asp Arg Tyr Leu Arg Phe Ser Tyr Ala Leu Arg Leu Glu Asp Ile Glu
    370                 375                 380

GAG GGG ATG CAA CGG TTT AAA GAA TTG ATC GAA GCG GCA CTT TAA            1197
Glu Gly Met Gln Arg Phe Lys Glu Leu Ile Glu Ala Ala Leu
385                 390                 395
```

(2) INFORMATION FOR SEQ ID NO:22:

(i) SEQUENCE CHARACTERISTICS:
        (A) LENGTH: 1779 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1776

(xi) SEQUENCE DESCRIPTION: SEQ ID NO:22:

```
ATG TGC GGG ATA GTC GGA TAC GTA GGG AGG GAT TTA GCC CTT CCT ATA        48
Met Cys Gly Ile Val Gly Tyr Val Gly Arg Asp Leu Ala Leu Pro Ile
1               5                   10                  15

GTC CTC GGA GCT CTT GAG AGA CTC GAA TAC AGG GGT TAC GAC TCC GCG        96
Val Leu Gly Ala Leu Glu Arg Leu Glu Tyr Arg Gly Tyr Asp Ser Ala
                20                  25                  30

GGA GTT GCC CTT ATA GAA GAC GGG AAA CTC ATA GTT GAA AAG AAG AAG        144
Gly Val Ala Leu Ile Glu Asp Gly Lys Leu Ile Val Glu Lys Lys Lys
            35                  40                  45

GGA AAG ATA AGG GAA CTC GTT AAA GCG CTA TGG GGA AAG GAT TAC AAG        192
Gly Lys Ile Arg Glu Leu Val Lys Ala Leu Trp Gly Lys Asp Tyr Lys
    50                  55                  60

GCT AAA ACG GGT ATA GGT CAC ACA CGC TGG GCA ACC CAC GGA AAG CCC        240
Ala Lys Thr Gly Ile Gly His Thr Arg Trp Ala Thr His Gly Lys Pro
65                  70                  75                  80

ACG GAC GAG AAC GCC CAC CCC CAC ACC GAC GAA AAA GGT GAG TTT GCA        288
Thr Asp Glu Asn Ala His Pro His Thr Asp Glu Lys Gly Glu Phe Ala
                85                  90                  95

GTA GTT CAC AAC GGG ATA ATA GAA AAC TAC TTA GAA CTA AAA GAG GAA        336
Val Val His Asn Gly Ile Ile Glu Asn Tyr Leu Glu Leu Lys Glu Glu
                100                 105                 110

CTA AAG AAG GAA GGT GTA AAG TTC AGG TCC GAA ACA GAC ACA GAA GTT        384
Leu Lys Lys Glu Gly Val Lys Phe Arg Ser Glu Thr Asp Thr Glu Val
            115                 120                 125

ATA GCC CAC CTC ATA GCG AAG AAC TAC AGG GGG GAC TTA CTG GAG GCC        432
Ile Ala His Leu Ile Ala Lys Asn Tyr Arg Gly Asp Leu Leu Glu Ala
    130                 135                 140

GTT TTA AAA ACC GTA AAG AAA TTA AAG GGT GCT TTT GCC TTT GCG GTT        480
Val Leu Lys Thr Val Lys Lys Leu Lys Gly Ala Phe Ala Phe Ala Val
145                 150                 155                 160

ATA ACG GTT CAC GAA CCA AAC AGA CTA ATA GGA GTG AAG CAG GGG AGT        528
Ile Thr Val His Glu Pro Asn Arg Leu Ile Gly Val Lys Gln Gly Ser
                165                 170                 175

CCT TTA ATC GTC GGA CTC GGA GAA GGA GAA AAC TTC CTC GCT TCA GAT        576
Pro Leu Ile Val Gly Leu Gly Glu Gly Glu Asn Phe Leu Ala Ser Asp
                180                 185                 190

ATT CCC GCA ATA CTT CCT TAC ACG AAA AAG ATT ATT GTT CTT GAT GAC        624
Ile Pro Ala Ile Leu Pro Tyr Thr Lys Lys Ile Ile Val Leu Asp Asp
            195                 200                 205

GGG GAA ATA GCG GAC CTG ACT CCC GAC ACT GTG AAC ATT TAC AAC TTT        672
```

```
Gly Glu Ile Ala Asp Leu Thr Pro Asp Thr Val Asn Ile Tyr Asn Phe
    210                 215                 220

GAG GGA GAG CCC GTT TCA AAG GAA GTA ATG ATT ACG CCC TGG GAT CTT       720
Glu Gly Glu Pro Val Ser Lys Glu Val Met Ile Thr Pro Trp Asp Leu
225                 230                 235                 240

GTT TCT GCG GAA AAG GGT GGT TTT AAA CAC TTC ATG CTA AAA GAG ATA       768
Val Ser Ala Glu Lys Gly Gly Phe Lys His Phe Met Leu Lys Glu Ile
                245                 250                 255

TAC GAA CAG CCC AAA GCC ATA AAC GAC ACA CTC AAG GGT TTC CTC TCA       816
Tyr Glu Gln Pro Lys Ala Ile Asn Asp Thr Leu Lys Gly Phe Leu Ser
            260                 265                 270

ACC GAA GAC GCA ATA CCC TTT AAG TTA AAA GAC TTC AGA AGG GTT TTA       864
Thr Glu Asp Ala Ile Pro Phe Lys Leu Lys Asp Phe Arg Arg Val Leu
        275                 280                 285

ATA ATA GCG TGC GGG ACC TCT TAC CAC GCG GGC TTC GTC GGA AAG TAC       912
Ile Ile Ala Cys Gly Thr Ser Tyr His Ala Gly Phe Val Gly Lys Tyr
    290                 295                 300

TGG ATA GAG AGA TTT GCA GGT GTT CCC ACA GAG GTA ATT TAC GCT TCG       960
Trp Ile Glu Arg Phe Ala Gly Val Pro Thr Glu Val Ile Tyr Ala Ser
305                 310                 315                 320

GAA TTC AGG TAT GCG GAC GTT CCC GTT TCG GAC AAG GAT ATC GTT ATC      1008
Glu Phe Arg Tyr Ala Asp Val Pro Val Ser Asp Lys Asp Ile Val Ile
                325                 330                 335

GGA ATT TCC CAG TCA GGA GAG ACC GCT GAC ACA AAG TTT GCC CTT CAG      1056
Gly Ile Ser Gln Ser Gly Glu Thr Ala Asp Thr Lys Phe Ala Leu Gln
            340                 345                 350

TCC GCA AAG GAA AAG GGA GCC TTT ACC GTG GGA CTC GTA AAC GTA GTG      1104
Ser Ala Lys Glu Lys Gly Ala Phe Thr Val Gly Leu Val Asn Val Val
        355                 360                 365

GGA AGT GCC ATA GAC AGG GAG TCG GAC TTT TCC CTT CAC ACA CAT GCG      1152
Gly Ser Ala Ile Asp Arg Glu Ser Asp Phe Ser Leu His Thr His Ala
    370                 375                 380

GGA CCC GAA ATA GGC GTG GCG GCT ACA AAG ACC TTC ACC GCA CAG TTC      1200
Gly Pro Glu Ile Gly Val Ala Ala Thr Lys Thr Phe Thr Ala Gln Phe
385                 390                 395                 400

ACC GCA CTC TAC GCC CTT TCG GTA AGG GAA AGT GAG GAG AGG GAA AAT      1248
Thr Ala Leu Tyr Ala Leu Ser Val Arg Glu Ser Glu Glu Arg Glu Asn
                405                 410                 415

CTA ATA AGA CTC CTT GAA AAG GTT CCA TCA CTC GTT GAA CAA ACA CTG      1296
Leu Ile Arg Leu Leu Glu Lys Val Pro Ser Leu Val Glu Gln Thr Leu
            420                 425                 430

AAC ACC GCA GAA GAA GTG GAG AAG GTA GCG GAA AAG TAC ATG AAA AAG      1344
Asn Thr Ala Glu Glu Val Glu Lys Val Ala Glu Lys Tyr Met Lys Lys
        435                 440                 445

AAA AAC ATG CTT TAC CTC GGA AGG TAC TTA AAT TAC CCC ATA GCG CTG      1392
Lys Asn Met Leu Tyr Leu Gly Arg Tyr Leu Asn Tyr Pro Ile Ala Leu
    450                 455                 460

GAG GGA GCT CTT AAA CTT AAA GAA ATT TCT TAC ATA CAC GCG GAA GGT      1440
Glu Gly Ala Leu Lys Leu Lys Glu Ile Ser Tyr Ile His Ala Glu Gly
465                 470                 475                 480

TAT CCC GCA GGG GAG ATG AAG CAC GGT CCC ATA GCC CTC ATA GAC GAA      1488
Tyr Pro Ala Gly Glu Met Lys His Gly Pro Ile Ala Leu Ile Asp Glu
                485                 490                 495

AAC ATG CCG GTT GTG GTA ATC GCA CCG AAA GAC AGG GTT TAC GAG AAG      1536
Asn Met Pro Val Val Val Ile Ala Pro Lys Asp Arg Val Tyr Glu Lys
            500                 505                 510

ATA CTC TCA AAC GTA GAA GAG GTT CTC GCA AGA AAG GGA AGG GTT ATT      1584
Ile Leu Ser Asn Val Glu Glu Val Leu Ala Arg Lys Gly Arg Val Ile
        515                 520                 525
```

-continued

```
TCT GTA GGC TTT AAA GGA GAC GAA ACT CTC AAA AGC AAA TCC GAG AGC      1632
Ser Val Gly Phe Lys Gly Asp Glu Thr Leu Lys Ser Lys Ser Glu Ser
    530                 535                 540

GTT ATG GAA ATC CCG AAG GCA GAA GAA CCG ATA ACT CCT TTC TTG ACG      1680
Val Met Glu Ile Pro Lys Ala Glu Glu Pro Ile Thr Pro Phe Leu Thr
545                 550                 555                 560

GTA ATA CCC CTG CAA CTC TTT GCC TAC TTT ATA GCG AGC AAA CTG GGA      1728
Val Ile Pro Leu Gln Leu Phe Ala Tyr Phe Ile Ala Ser Lys Leu Gly
                565                 570                 575

CTG GAT GTG GAT CAG CCG AGA AAT CTC GCC AAA ACG GTC ACG GTG GAA      1776
Leu Asp Val Asp Gln Pro Arg Asn Leu Ala Lys Thr Val Thr Val Glu
            580                 585                 590

TAA                                                                   1779
```

(2) INFORMATION FOR SEQ ID NO:23:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1062

(xi) SEQUENCE DESCRIPTION: SEQ ID NO:23:

```
ATG ATA CCC CAG AGG ATT AAG GAA CTT GAA GCT TAC AAG ACG GAG GTC       48
Met Ile Pro Gln Arg Ile Lys Glu Leu Glu Ala Tyr Lys Thr Glu Val
  1                 5                  10                  15

ACT CCC GCC TCC GTC AGG CTT TCC TCT AAC GAA TTC CCC TAC GAC TTT       96
Thr Pro Ala Ser Val Arg Leu Ser Ser Asn Glu Phe Pro Tyr Asp Phe
                 20                  25                  30

CCC GAG GAG ATA AAA CAA AGG GCC TTA GAA GAA TTA AAA AAG GTT CCC      144
Pro Glu Glu Ile Lys Gln Arg Ala Leu Glu Glu Leu Lys Lys Val Pro
             35                  40                  45

TTG AAC AAA TAC CCA GAC CCC GAA GCG AAA GAG TTA AAA GCG GTT CTT      192
Leu Asn Lys Tyr Pro Asp Pro Glu Ala Lys Glu Leu Lys Ala Val Leu
     50                  55                  60

GCG GAT TTT TTC GGC GTT AAG GAA GAA AAT TTA GTT CTC GGT AAC GGT      240
Ala Asp Phe Phe Gly Val Lys Glu Glu Asn Leu Val Leu Gly Asn Gly
 65                  70                  75                  80

TCG GAC GAA CTC ATA TAC TAC CTC TCA ATA GCT ATA GGT GAA CTT TAC      288
Ser Asp Glu Leu Ile Tyr Tyr Leu Ser Ile Ala Ile Gly Glu Leu Tyr
                 85                  90                  95

ATA CCC GTT TAC ATA CCT GTT CCC ACC TTT CCC ATG TAC GAG ATA AGT      336
Ile Pro Val Tyr Ile Pro Val Pro Thr Phe Pro Met Tyr Glu Ile Ser
                100                 105                 110

GCG AAA GTT CTC GGA AGA CCC CTC GTA AAG GTT CAA CTG GAC GAA AAC      384
Ala Lys Val Leu Gly Arg Pro Leu Val Lys Val Gln Leu Asp Glu Asn
            115                 120                 125

TTT GAT ATA GAC TTA GAA AGA AGT ATT GAA TTA ATA GAG AAA GAA AAA      432
Phe Asp Ile Asp Leu Glu Arg Ser Ile Glu Leu Ile Glu Lys Glu Lys
    130                 135                 140

CCC GTT CTC GGG TAC TTT GCT TAC CCA AAC AAC CCC ACG GGA AAC CTC      480
Pro Val Leu Gly Tyr Phe Ala Tyr Pro Asn Asn Pro Thr Gly Asn Leu
145                 150                 155                 160

TTT TCC AGG GGA AAG ATT GAG GAG ATA AGA AAC AGG GGT GTT TTC TGT      528
Phe Ser Arg Gly Lys Ile Glu Glu Ile Arg Asn Arg Gly Val Phe Cys
                165                 170                 175
```

```
GTA ATA GAC GAA GCC TAC TAT CAT TAC TCC GGA GAA ACC TTT CTG GAA        576
Val Ile Asp Glu Ala Tyr Tyr His Tyr Ser Gly Glu Thr Phe Leu Glu
        180                 185                 190

GAC GCG CTC AAA AGG GAA GAT ACG GTA GTT TTG AGG ACA CTT TCA AAA        624
Asp Ala Leu Lys Arg Glu Asp Thr Val Val Leu Arg Thr Leu Ser Lys
                195                 200                 205

ATC GGT ATG GCG AGT TTA AGG GTA GGG ATT TTA ATA GGG AAG GGG GAA        672
Ile Gly Met Ala Ser Leu Arg Val Gly Ile Leu Ile Gly Lys Gly Glu
        210                 215                 220

ATC GTC TCA GAA ATT AAC AAG GTG AGA CTC CCC TTC AAC GTG ACC TAC        720
Ile Val Ser Glu Ile Asn Lys Val Arg Leu Pro Phe Asn Val Thr Tyr
225                 230                 235                 240

CCC TCT CAG GTG ATG GCA AAA GTT CTC CTC ACG GAG GGA AGA GAA TTC        768
Pro Ser Gln Val Met Ala Lys Val Leu Leu Thr Glu Gly Arg Glu Phe
                245                 250                 255

CTA ATG GAA AAG ATA CAG GAG GTT GTA ACA GAG CGA GAA AGG ATG TAC        816
Leu Met Glu Lys Ile Gln Glu Val Val Thr Glu Arg Glu Arg Met Tyr
        260                 265                 270

GAC GAA ATG AAG AAA ATA GAA GGA GTT GAG GTT TTT CCG AGT AAG GCT        864
Asp Glu Met Lys Lys Ile Glu Gly Val Glu Val Phe Pro Ser Lys Ala
                275                 280                 285

AAC TTC TTG CTT TTC AGA ACG CCT TAC CCC GCC CAC GAG GTT TAT CAG        912
Asn Phe Leu Leu Phe Arg Thr Pro Tyr Pro Ala His Glu Val Tyr Gln
        290                 295                 300

GAG CTA CTG AAA AGG GAT GTC CTC GTC AGG AAC GTA TCT TAC ATG GAA        960
Glu Leu Leu Lys Arg Asp Val Leu Val Arg Asn Val Ser Tyr Met Glu
305                 310                 315                 320

GGA CTC CAA AAG TGC CTC AGG GTA AGC GTA GGG AAA CCG GAA GAA AAC       1008
Gly Leu Gln Lys Cys Leu Arg Val Ser Val Gly Lys Pro Glu Glu Asn
                325                 330                 335

AAC AAG TTT CTG GAA GCA CTG GAG GAG AGT ATA AAA TCC CTT TCA AGC       1056
Asn Lys Phe Leu Glu Ala Leu Glu Glu Ser Ile Lys Ser Leu Ser Ser
        340                 345                 350

TCT CTT TAA                                                           1065
Ser Leu
```

(2) INFORMATION FOR SEQ ID NO:24:

(i) SEQUENCE CHARACTERISTICS:
        (A) LENGTH: 912 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...909

(xi) SEQUENCE DESCRIPTION: SEQ ID NO:24:

```
ATG AAG CCG TAC GCT AAA TAT ATC TGG CTT GAC GGC AGA ATA CTT AAG         48
Met Lys Pro Tyr Ala Lys Tyr Ile Trp Leu Asp Gly Arg Ile Leu Lys
1               5                   10                  15

TGG GAA GAC GCG AAA ATA CAC GTG TTG ACT CAC GCG CTT CAC TAC GGA         96
Trp Glu Asp Ala Lys Ile His Val Leu Thr His Ala Leu His Tyr Gly
                20                  25                  30

ACC TCT ATA TTC GAG GGA ATA AGA GGG TAT TGG AAC GGC GAT AAT TTG        144
Thr Ser Ile Phe Glu Gly Ile Arg Gly Tyr Trp Asn Gly Asp Asn Leu
        35                  40                  45

CTC GTC TTT AGG TTA GAA GAA CAC ATC GAC CGC ATG TAC AGA TCG GCT        192
Leu Val Phe Arg Leu Glu Glu His Ile Asp Arg Met Tyr Arg Ser Ala
50                  55                  60
```

```
AAG ATA CTA GGC ATA AAT ATT CCG TAT ACA AGA GAG GAA GTC CGC CAA      240
Lys Ile Leu Gly Ile Asn Ile Pro Tyr Thr Arg Glu Glu Val Arg Gln
 65              70                  75                  80

GCT GTA CTA GAG ACC ATA AAG GCT AAT AAC TTC CGA GAG GAT GTC TAC      288
Ala Val Leu Glu Thr Ile Lys Ala Asn Asn Phe Arg Glu Asp Val Tyr
                 85                  90                  95

ATA AGA CCT GTG GCG TTT GTC GCC TCG CAG ACG GTG ACG CTT GAC ATA      336
Ile Arg Pro Val Ala Phe Val Ala Ser Gln Thr Val Thr Leu Asp Ile
             100                 105                 110

AGA AAT TTG GAA GTC TCC CTC GCG GTT ATT GTA TTC CCA TTT GGC AAA      384
Arg Asn Leu Glu Val Ser Leu Ala Val Ile Val Phe Pro Phe Gly Lys
         115                 120                 125

TAC CTC TCG CCC AAC GGC ATT AAG GCA ACG ATT GTA AGC TGG CGT AGA      432
Tyr Leu Ser Pro Asn Gly Ile Lys Ala Thr Ile Val Ser Trp Arg Arg
     130                 135                 140

GTA CAT AAT ACA ATG CTC CCT GTG ATG GCA AAA ATC GGC GGT ATA TAT      480
Val His Asn Thr Met Leu Pro Val Met Ala Lys Ile Gly Gly Ile Tyr
145                 150                 155                 160

GTA AAC TCT GTA CTT GCG CTT GTA GAG GCT AGA AGC AGG GGA TTT GAC      528
Val Asn Ser Val Leu Ala Leu Val Glu Ala Arg Ser Arg Gly Phe Asp
                165                 170                 175

GAG GCT TTA TTA ATG GAC GTT AAC GGT TAT GTT GTT GAG GGT TCT GGA      576
Glu Ala Leu Leu Met Asp Val Asn Gly Tyr Val Val Glu Gly Ser Gly
            180                 185                 190

GAG AAT ATT TTC ATT GTC AGA GGT GGA AGG CTT TTC ACG CCG CCA GTA      624
Glu Asn Ile Phe Ile Val Arg Gly Gly Arg Leu Phe Thr Pro Pro Val
        195                 200                 205

CAC GAA TCT ATC CTC GAG GGA ATT ACG AGG GAT ACG GTA ATA AAG CTC      672
His Glu Ser Ile Leu Glu Gly Ile Thr Arg Asp Thr Val Ile Lys Leu
    210                 215                 220

AGC GGG GAT GTG GGA CTT CGG GTG GAG GAA AAG CCT ATT ACG AGG GAG      720
Ser Gly Asp Val Gly Leu Arg Val Glu Glu Lys Pro Ile Thr Arg Glu
225                 230                 235                 240

GAG GTG TAT ACA GCC GAC GAG GTG TTT TTA GTA GGA ACC GCC GCA GAG      768
Glu Val Tyr Thr Ala Asp Glu Val Phe Leu Val Gly Thr Ala Ala Glu
                245                 250                 255

ATA ACG CCA GTG GTG GAG GTT GAC GGC AGA ACA ATC GGC ACA GGC AAG      816
Ile Thr Pro Val Val Glu Val Asp Gly Arg Thr Ile Gly Thr Gly Lys
            260                 265                 270

CCG GGC CCC ATT ACG ACA AAA ATA GCT GAG CTG TAC TCA AAC GTC GTG      864
Pro Gly Pro Ile Thr Thr Lys Ile Ala Glu Leu Tyr Ser Asn Val Val
        275                 280                 285

AGA GGC AAA GTA GAG AAA TAC TTA AAT TGG ATC ACT CCT GTG TAT TAG      912
Arg Gly Lys Val Glu Lys Tyr Leu Asn Trp Ile Thr Pro Val Tyr
    290                 295                 300
```

(2) INFORMATION FOR SEQ ID NO:25:

(i) SEQUENCE CHARACTERISTICS:
        (A) LENGTH: 414 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:25:

```
Met Ile Glu Asp Pro Met Asp Trp Ala Phe Pro Arg Ile Lys Arg Leu
  1               5                  10                  15

Pro Gln Tyr Val Phe Ser Leu Val Asn Glu Leu Lys Tyr Lys Leu Arg
```

```
                  20                  25                  30
Arg Glu Gly Glu Asp Val Val Asp Leu Gly Met Gly Asn Pro Asn Met
            35                  40                  45
Pro Pro Ala Lys His Ile Ile Asp Lys Leu Cys Glu Val Ala Gln Lys
 50                  55                  60
Pro Asn Val His Gly Tyr Ser Ala Ser Arg Gly Ile Pro Arg Leu Arg
 65                  70                  75                  80
Lys Ala Ile Cys Asn Phe Tyr Glu Glu Arg Tyr Gly Val Lys Leu Asp
                85                  90                  95
Pro Glu Arg Glu Ala Ile Leu Thr Ile Gly Ala Lys Glu Gly Tyr Ser
            100                 105                 110
His Leu Met Leu Ala Met Ile Ser Pro Gly Asp Thr Val Ile Val Pro
            115                 120                 125
Asn Pro Thr Tyr Pro Ile His Tyr Tyr Ala Pro Ile Ile Ala Gly Gly
            130                 135                 140
Glu Val His Ser Ile Pro Leu Asn Phe Ser Asp Gln Asp His Gln
145                 150                 155                 160
Glu Glu Phe Leu Arg Arg Leu Tyr Glu Ile Val Lys Thr Ala Met Pro
                165                 170                 175
Lys Pro Lys Ala Val Val Ile Ser Phe Pro His Asn Pro Thr Thr Ile
            180                 185                 190
Thr Val Glu Lys Asp Phe Phe Lys Glu Ile Val Lys Phe Ala Lys Glu
            195                 200                 205
His Gly Leu Trp Ile Ile His Asp Phe Ala Tyr Ala Asp Ile Ala Phe
            210                 215                 220
Asp Gly Tyr Lys Pro Pro Ser Ile Leu Glu Ile Glu Gly Ala Lys Asp
225                 230                 235                 240
Val Ala Val Glu Leu Tyr Ser Met Ser Lys Gly Phe Ser Met Ala Gly
                245                 250                 255
Trp Arg Val Ala Phe Val Val Gly Asn Glu Ile Leu Ile Lys Asn Leu
            260                 265                 270
Ala His Leu Lys Ser Tyr Leu Asp Tyr Gly Ile Phe Thr Pro Ile Gln
            275                 280                 285
Val Ala Ser Ile Ile Ala Leu Glu Ser Pro Tyr Glu Ile Val Glu Lys
            290                 295                 300
Thr Ala Lys Val Tyr Gln Lys Arg Arg Asp Val Leu Val Glu Gly Leu
305                 310                 315                 320
Asn Arg Leu Gly Trp Lys Val Lys Pro Lys Ala Thr Met Phe Val
                325                 330                 335
Trp Ala Lys Ile Pro Glu Trp Ile Asn Met Asn Ser Leu Asp Phe Ser
            340                 345                 350
Leu Phe Leu Leu Lys Glu Ala Lys Val Ala Val Ser Pro Gly Val Gly
            355                 360                 365
Phe Gly Gln Tyr Gly Glu Gly Tyr Val Arg Phe Ala Leu Val Glu Asn
            370                 375                 380
Glu His Arg Ile Arg Gln Ala Ile Arg Gly Ile Arg Lys Ala Phe Arg
385                 390                 395                 400
Lys Leu Gln Lys Glu Arg Lys Leu Glu Pro Glu Arg Ser Ala
                405                 410
```

(2) INFORMATION FOR SEQ ID NO:26:

(i) SEQUENCE CHARACTERISTICS:
        (A) LENGTH: 373 amino acids (B) TYPE: amino acid
(D) TOPOLOGY: linear (ii) MOLECULE TYPE: protein (v) FRAGMENT TYPE: internal (xi) SEQUENCE DESCRIPTION: SEQ ID NO:26:

```
Met Asp Arg Leu Glu Lys Val Ser Pro Phe Ile Val Met Asp Ile Leu
 1               5                  10                  15

Ala Gln Ala Gln Lys Tyr Glu Asp Val Val His Met Glu Ile Gly Glu
                20                  25                  30

Pro Asp Leu Glu Pro Ser Pro Lys Val Met Glu Ala Leu Glu Arg Ala
            35                  40                  45

Val Lys Glu Lys Thr Phe Phe Tyr Thr Pro Ala Leu Gly Leu Trp Glu
 50                  55                  60

Leu Arg Glu Arg Ile Ser Glu Phe Tyr Arg Lys Lys Tyr Ser Val Glu
 65                  70                  75                  80

Val Ser Pro Glu Arg Val Ile Val Thr Gly Thr Ser Gly Ala Phe
                85                  90                  95

Leu Val Ala Tyr Ala Val Thr Leu Asn Ala Gly Glu Lys Ile Ile Leu
               100                 105                 110

Pro Asp Pro Ser Tyr Pro Cys Tyr Lys Asn Phe Ala Tyr Leu Leu Asp
           115                 120                 125

Ala Gln Pro Val Phe Val Asn Val Asp Lys Glu Thr Asn Tyr Glu Val
130                 135                 140

Arg Lys Glu Met Ile Glu Asp Ile Asp Ala Lys Ala Leu His Ile Ser
145                 150                 155                 160

Ser Pro Gln Asn Pro Thr Gly Thr Leu Tyr Ser Pro Glu Thr Leu Lys
                165                 170                 175

Glu Leu Ala Glu Tyr Cys Glu Glu Lys Gly Met Tyr Phe Ile Ser Asp
            180                 185                 190

Glu Ile Tyr His Gly Leu Val Tyr Glu Gly Arg Glu His Thr Ala Leu
        195                 200                 205

Glu Phe Ser Asp Arg Ala Ile Val Ile Asn Gly Phe Ser Lys Tyr Phe
210                 215                 220

Cys Met Pro Gly Phe Arg Ile Gly Trp Met Ile Val Pro Glu Glu Leu
225                 230                 235                 240

Val Arg Lys Ala Glu Ile Val Ile Gln Asn Val Phe Ile Ser Ala Pro
                245                 250                 255

Thr Leu Ser Gln Tyr Ala Ala Leu Glu Ala Phe Asp Tyr Glu Tyr Leu
            260                 265                 270

Glu Lys Val Arg Lys Thr Phe Glu Glu Arg Arg Asn Phe Leu Tyr Gly
        275                 280                 285

Glu Leu Lys Lys Leu Phe Lys Ile Asp Ala Lys Pro Gln Gly Ala Phe
290                 295                 300

Tyr Val Trp Ala Asn Ile Ser Asp Tyr Ser Thr Asp Ser Tyr Glu Phe
305                 310                 315                 320

Ala Leu Lys Leu Leu Arg Glu Ala Arg Val Ala Val Thr Pro Gly Val
                325                 330                 335

Asp Phe Gly Lys Asn Lys Thr Lys Glu Tyr Ile Arg Phe Ala Tyr Thr
            340                 345                 350

Arg Lys Ile Glu Glu Leu Lys Glu Gly Val Glu Arg Ile Lys Lys Phe
        355                 360                 365

Leu Glu Lys Leu Ser
```

370

(2) INFORMATION FOR SEQ ID NO:27:

(i) SEQUENCE CHARACTERISTICS:
        (A) LENGTH: 453 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:27:

```
Met Trp Glu Leu Asp Pro Lys Thr Leu Glu Lys Trp Asp Lys Glu Tyr
  1               5                  10                  15

Phe Trp His Pro Phe Thr Gln Met Lys Val Tyr Arg Glu Glu Glu Asn
                 20                  25                  30

Leu Ile Phe Glu Arg Gly Glu Gly Val Tyr Leu Trp Asp Ile Tyr Gly
             35                  40                  45

Arg Lys Tyr Ile Asp Ala Ile Ser Ser Leu Trp Cys Asn Val His Gly
 50                  55                  60

His Asn His Pro Lys Leu Asn Asn Ala Val Met Lys Gln Leu Cys Lys
 65                  70                  75                  80

Val Ala His Thr Thr Thr Leu Gly Ser Ser Asn Val Pro Ala Ile Leu
                 85                  90                  95

Leu Ala Lys Lys Leu Val Glu Ile Ser Pro Glu Gly Leu Asn Lys Val
                100                 105                 110

Phe Tyr Ser Glu Asp Gly Ala Glu Ala Val Glu Ile Ala Ile Lys Met
            115                 120                 125

Ala Tyr His Tyr Trp Lys Asn Lys Gly Val Lys Gly Lys Asn Val Phe
130                 135                 140

Ile Thr Leu Ser Glu Ala Tyr His Gly Asp Thr Val Gly Ala Val Ser
145                 150                 155                 160

Val Gly Gly Ile Glu Leu Phe His Gly Thr Tyr Lys Asp Leu Leu Phe
                165                 170                 175

Lys Thr Ile Lys Leu Pro Ser Pro Tyr Leu Tyr Cys Lys Glu Lys Tyr
            180                 185                 190

Gly Glu Leu Cys Pro Glu Cys Thr Ala Asp Leu Leu Lys Gln Leu Glu
            195                 200                 205

Asp Ile Leu Lys Ser Arg Glu Asp Ile Val Ala Val Ile Met Glu Ala
210                 215                 220

Gly Ile Gln Ala Ala Gly Met Leu Pro Phe Pro Gly Phe Leu
225                 230                 235                 240

Lys Gly Val Arg Glu Leu Thr Lys Lys Tyr Asp Thr Leu Met Ile Val
                245                 250                 255

Asp Glu Val Ala Thr Gly Phe Gly Arg Thr Gly Thr Met Phe Tyr Cys
            260                 265                 270

Glu Gln Glu Gly Val Ser Pro Asp Phe Met Cys Leu Gly Lys Gly Ile
            275                 280                 285

Thr Gly Gly Tyr Leu Pro Leu Ala Ala Thr Leu Thr Asp Glu Val
            290                 295                 300

Phe Asn Ala Phe Leu Gly Glu Phe Gly Glu Ala Lys His Phe Tyr His
305                 310                 315                 320

Gly His Thr Tyr Thr Gly Asn Asn Leu Ala Cys Ser Val Ala Leu Ala
                325                 330                 335
```

```
Asn Leu Glu Val Phe Glu Glu Arg Thr Leu Glu Lys Leu Gln Pro
            340                 345                 350

Lys Ile Lys Leu Leu Lys Glu Arg Leu Gln Glu Phe Trp Glu Leu Lys
        355                 360                 365

His Val Gly Asp Val Arg Gln Leu Gly Phe Met Ala Gly Ile Glu Leu
    370                 375                 380

Val Lys Asp Lys Glu Lys Gly Pro Phe Pro Tyr Gly Glu Arg Thr
385                 390                 395                 400

Gly Phe Lys Val Ala Tyr Lys Cys Arg Glu Lys Gly Val Phe Leu Arg
                405                 410                 415

Pro Leu Gly Asp Val Met Val Leu Met Met Pro Leu Val Ile Glu Glu
            420                 425                 430

Asp Glu Met Asn Tyr Val Ile Asp Thr Leu Lys Trp Ala Ile Lys Glu
        435                 440                 445

Leu Glu Lys Glu Val
    450

(2) INFORMATION FOR SEQ ID NO:28:

(i) SEQUENCE CHARACTERISTICS:
        (A) LENGTH: 343 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:28:

Met Thr Tyr Leu Met Asn Asn Tyr Ala Arg Leu Pro Val Lys Phe Val
1               5                  10                  15

Arg Gly Lys Gly Val Tyr Leu Tyr Asp Glu Glu Gly Lys Glu Tyr Leu
            20                  25                  30

Asp Phe Val Ser Gly Ile Gly Val Asn Ser Leu Gly His Ala Tyr Pro
        35                  40                  45

Lys Leu Thr Glu Ala Leu Lys Glu Gln Val Glu Lys Leu Leu His Val
    50                  55                  60

Ser Asn Leu Tyr Glu Asn Pro Trp Gln Glu Glu Leu Ala His Lys Leu
65                  70                  75                  80

Val Lys His Phe Trp Thr Glu Gly Lys Val Phe Phe Ala Asn Ser Gly
                85                  90                  95

Thr Glu Ser Val Glu Ala Ala Ile Lys Leu Ala Arg Lys Tyr Trp Arg
            100                 105                 110

Asp Lys Gly Lys Asn Lys Trp Lys Phe Ile Ser Phe Glu Asn Ser Phe
        115                 120                 125

His Gly Arg Thr Tyr Gly Ser Leu Ser Ala Thr Gly Gln Pro Lys Phe
    130                 135                 140

His Lys Gly Phe Glu Pro Leu Val Pro Gly Phe Ser Tyr Ala Lys Leu
145                 150                 155                 160

Asn Asp Ile Asp Ser Val Tyr Lys Leu Leu Asp Glu Glu Thr Ala Gly
                165                 170                 175

Ile Ile Ile Glu Val Ile Gln Gly Glu Gly Gly Val Asn Glu Ala Ser
            180                 185                 190

Glu Asp Phe Leu Ser Lys Leu Gln Glu Ile Cys Lys Glu Lys Asp Val
        195                 200                 205

Leu Leu Ile Ile Asp Glu Val Gln Thr Gly Ile Gly Arg Thr Gly Glu
    210                 215                 220
```

```
Phe Tyr Ala Tyr Gln His Phe Asn Leu Lys Pro Asp Val Ile Ala Leu
225                 230                 235                 240

Ala Lys Gly Leu Gly Gly Val Pro Ile Gly Ala Ile Leu Ala Arg
            245                 250                 255

Glu Glu Val Ala Gln Ser Phe Thr Pro Gly Ser His Gly Ser Thr Phe
            260                 265                 270

Gly Gly Asn Pro Leu Ala Cys Arg Ala Gly Thr Val Val Asp Glu
            275                 280                 285

Val Glu Lys Leu Leu Pro His Val Arg Glu Val Gly Asn Tyr Phe Lys
290                 295                 300

Glu Lys Leu Lys Glu Leu Gly Lys Gly Lys Val Lys Gly Arg Gly Leu
305                 310                 315                 320

Met Leu Gly Leu Glu Leu Glu Arg Glu Cys Lys Asp Tyr Val Leu Lys
            325                 330                 335

Ala Leu Glu Arg Asp Phe Ser
            340
```

(2) INFORMATION FOR SEQ ID NO:29:

(i) SEQUENCE CHARACTERISTICS:
        (A) LENGTH: 398 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:29:

```
Met Arg Lys Leu Ala Glu Arg Ala Gln Lys Leu Ser Pro Ser Pro Thr
1               5                   10                  15

Leu Ser Val Asp Thr Lys Ala Lys Glu Leu Leu Arg Gln Gly Glu Arg
            20                  25                  30

Val Ile Asn Phe Gly Ala Gly Glu Pro Asp Phe Asp Thr Pro Glu His
            35                  40                  45

Ile Lys Glu Ala Ala Lys Arg Ala Leu Asp Gln Gly Phe Thr Lys Tyr
        50                  55                  60

Thr Pro Val Ala Gly Ile Leu Pro Leu Arg Glu Ala Ile Cys Glu Lys
65                  70                  75                  80

Leu Tyr Arg Asp Asn Gln Leu Glu Tyr Ser Pro Asn Glu Ile Val Val
            85                  90                  95

Ser Cys Gly Ala Lys His Ser Ile Phe Asn Ala Leu Gln Val Leu Leu
            100                 105                 110

Asp Pro Gly Asp Glu Val Ile Ile Pro Val Pro Tyr Trp Thr Ser Tyr
            115                 120                 125

Pro Glu Gln Val Lys Leu Ala Gly Gly Val Pro Val Phe Val Pro Thr
            130                 135                 140

Ser Pro Glu Asn Asp Phe Lys Leu Arg Pro Glu Asp Leu Arg Ala Ala
145                 150                 155                 160

Val Thr Pro Arg Thr Arg Leu Leu Ile Leu Asn Ser Pro Ala Asn Pro
            165                 170                 175

Thr Gly Thr Val Tyr Arg Arg Glu Glu Leu Ile Gly Leu Ala Glu Val
            180                 185                 190

Ala Leu Glu Ala Asp Leu Trp Ile Leu Ser Asp Glu Ile Tyr Glu Lys
            195                 200                 205

Leu Ile Tyr Asp Gly Met Glu His Val Ser Ile Ala Ala Leu Asp Pro
```

```
                    210                 215                 220
Glu Val Lys Lys Arg Thr Ile Val Val Asn Gly Val Ser Lys Ala Tyr
225                 230                 235                 240

Ala Met Thr Gly Trp Arg Ile Gly Tyr Ala Ala Pro Arg Pro Ile
                245                 250                 255

Ala Gln Ala Met Thr Asn Leu Gln Ser His Ser Thr Ser Asn Pro Thr
                260                 265                 270

Ser Val Ala Gln Ala Ala Ala Leu Ala Ala Leu Lys Gly Pro Gln Glu
                275                 280                 285

Pro Val Glu Asn Met Arg Arg Ala Phe Gln Lys Arg Arg Asp Phe Ile
290                 295                 300

Trp Gln Tyr Leu Asn Ser Leu Pro Gly Val Arg Cys Pro Lys Pro Leu
305                 310                 315                 320

Gly Ala Phe Tyr Val Phe Pro Glu Val Glu Arg Ala Phe Gly Pro Pro
                325                 330                 335

Ser Lys Arg Thr Gly Asn Thr Thr Ala Ser Asp Leu Ala Leu Phe Leu
                340                 345                 350

Leu Glu Glu Ile Lys Val Ala Thr Val Ala Gly Ala Ala Phe Gly Asp
                355                 360                 365

Asp Arg Tyr Leu Arg Phe Ser Tyr Ala Leu Arg Leu Glu Asp Ile Glu
370                 375                 380

Glu Gly Met Gln Arg Phe Lys Glu Leu Ile Glu Ala Ala Leu
385                 390                 395
```

(2) INFORMATION FOR SEQ ID NO:30:

(i) SEQUENCE CHARACTERISTICS:
        (A) LENGTH: 592 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:30:

```
Met Cys Gly Ile Val Gly Tyr Val Gly Arg Asp Leu Ala Leu Pro Ile
1               5                   10                  15

Val Leu Gly Ala Leu Glu Arg Leu Glu Tyr Arg Gly Tyr Asp Ser Ala
                20                  25                  30

Gly Val Ala Leu Ile Glu Asp Gly Lys Leu Ile Val Glu Lys Lys Lys
                35                  40                  45

Gly Lys Ile Arg Glu Leu Val Lys Ala Leu Trp Gly Lys Asp Tyr Lys
50                  55                  60

Ala Lys Thr Gly Ile Gly His Thr Arg Trp Ala Thr His Gly Lys Pro
65                  70                  75                  80

Thr Asp Glu Asn Ala His Pro His Thr Asp Glu Lys Gly Glu Phe Ala
                85                  90                  95

Val Val His Asn Gly Ile Ile Glu Asn Tyr Leu Glu Leu Lys Glu Glu
                100                 105                 110

Leu Lys Lys Glu Gly Val Lys Phe Arg Ser Glu Thr Asp Thr Glu Val
                115                 120                 125

Ile Ala His Leu Ile Ala Lys Asn Tyr Arg Gly Asp Leu Leu Glu Ala
                130                 135                 140

Val Leu Lys Thr Val Lys Lys Leu Lys Gly Ala Phe Ala Phe Ala Val
145                 150                 155                 160
```

```
Ile Thr Val His Glu Pro Asn Arg Leu Ile Gly Val Lys Gln Gly Ser
            165                 170                 175
Pro Leu Ile Val Gly Leu Gly Glu Glu Asn Phe Leu Ala Ser Asp
        180                 185                 190
Ile Pro Ala Ile Leu Pro Tyr Thr Lys Lys Ile Ile Val Leu Asp Asp
        195                 200                 205
Gly Glu Ile Ala Asp Leu Thr Pro Asp Thr Val Asn Ile Tyr Asn Phe
    210                 215                 220
Glu Gly Glu Pro Val Ser Lys Glu Val Met Ile Thr Pro Trp Asp Leu
225                 230                 235                 240
Val Ser Ala Glu Lys Gly Phe Lys His Phe Met Leu Lys Glu Ile
                245                 250                 255
Tyr Glu Gln Pro Lys Ala Ile Asn Asp Thr Leu Lys Gly Phe Leu Ser
            260                 265                 270
Thr Glu Asp Ala Ile Pro Phe Lys Leu Lys Asp Phe Arg Arg Val Leu
        275                 280                 285
Ile Ile Ala Cys Gly Thr Ser Tyr His Ala Gly Phe Val Gly Lys Tyr
    290                 295                 300
Trp Ile Glu Arg Phe Ala Gly Val Pro Thr Glu Val Ile Tyr Ala Ser
305                 310                 315                 320
Glu Phe Arg Tyr Ala Asp Val Pro Val Ser Asp Lys Asp Ile Val Ile
                325                 330                 335
Gly Ile Ser Gln Ser Gly Glu Thr Ala Asp Thr Lys Phe Ala Leu Gln
            340                 345                 350
Ser Ala Lys Glu Lys Gly Ala Phe Thr Val Gly Leu Val Asn Val Val
        355                 360                 365
Gly Ser Ala Ile Asp Arg Glu Ser Asp Phe Ser Leu His Thr His Ala
    370                 375                 380
Gly Pro Glu Ile Gly Val Ala Ala Thr Lys Thr Phe Thr Ala Gln Phe
385                 390                 395                 400
Thr Ala Leu Tyr Ala Leu Ser Val Arg Glu Ser Glu Arg Glu Asn
                405                 410                 415
Leu Ile Arg Leu Leu Glu Lys Val Pro Ser Leu Val Glu Gln Thr Leu
            420                 425                 430
Asn Thr Ala Glu Glu Val Glu Lys Val Ala Glu Lys Tyr Met Lys Lys
        435                 440                 445
Lys Asn Met Leu Tyr Leu Gly Arg Tyr Leu Asn Tyr Pro Ile Ala Leu
    450                 455                 460
Glu Gly Ala Leu Lys Leu Lys Glu Ile Ser Tyr Ile His Ala Glu Gly
465                 470                 475                 480
Tyr Pro Ala Gly Glu Met Lys His Gly Pro Ile Ala Leu Ile Asp Glu
                485                 490                 495
Asn Met Pro Val Val Ile Ala Pro Lys Asp Arg Val Tyr Glu Lys
            500                 505                 510
Ile Leu Ser Asn Val Glu Glu Val Leu Ala Arg Lys Gly Arg Val Ile
        515                 520                 525
Ser Val Gly Phe Lys Gly Asp Glu Thr Leu Lys Ser Lys Ser Glu Ser
    530                 535                 540
Val Met Glu Ile Pro Lys Ala Glu Glu Pro Ile Thr Pro Phe Leu Thr
545                 550                 555                 560
Val Ile Pro Leu Gln Leu Phe Ala Tyr Phe Ile Ala Ser Lys Leu Gly
                565                 570                 575
Leu Asp Val Asp Gln Pro Arg Asn Leu Ala Lys Thr Val Thr Val Glu
```

```
                580              585              590
```

(2) INFORMATION FOR SEQ ID NO:31:

(i) SEQUENCE CHARACTERISTICS:
        (A) LENGTH: 354 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:31:

```
Met Ile Pro Gln Arg Ile Lys Glu Leu Glu Ala Tyr Lys Thr Glu Val
 1               5                  10                  15

Thr Pro Ala Ser Val Arg Leu Ser Ser Asn Glu Phe Pro Tyr Asp Phe
            20                  25                  30

Pro Glu Glu Ile Lys Gln Arg Ala Leu Glu Leu Lys Lys Val Pro
        35                  40                  45

Leu Asn Lys Tyr Pro Asp Pro Glu Ala Lys Glu Leu Lys Ala Val Leu
    50                  55                  60

Ala Asp Phe Phe Gly Val Lys Glu Asn Leu Val Leu Gly Asn Gly
65                  70                  75                  80

Ser Asp Glu Leu Ile Tyr Tyr Leu Ser Ile Ala Ile Gly Glu Leu Tyr
                85                  90                  95

Ile Pro Val Tyr Ile Pro Val Pro Thr Phe Pro Met Tyr Glu Ile Ser
            100                 105                 110

Ala Lys Val Leu Gly Arg Pro Leu Val Lys Val Gln Leu Asp Glu Asn
        115                 120                 125

Phe Asp Ile Asp Leu Glu Arg Ser Ile Glu Leu Ile Glu Lys Glu Lys
    130                 135                 140

Pro Val Leu Gly Tyr Phe Ala Tyr Pro Asn Asn Pro Thr Gly Asn Leu
145                 150                 155                 160

Phe Ser Arg Gly Lys Ile Glu Glu Ile Arg Asn Arg Gly Val Phe Cys
                165                 170                 175

Val Ile Asp Glu Ala Tyr Tyr His Tyr Ser Gly Glu Thr Phe Leu Glu
            180                 185                 190

Asp Ala Leu Lys Arg Glu Asp Thr Val Val Leu Arg Thr Leu Ser Lys
        195                 200                 205

Ile Gly Met Ala Ser Leu Arg Val Gly Ile Leu Ile Gly Lys Gly Glu
    210                 215                 220

Ile Val Ser Glu Ile Asn Lys Val Arg Leu Pro Phe Asn Val Thr Tyr
225                 230                 235                 240

Pro Ser Gln Val Met Ala Lys Val Leu Leu Thr Glu Gly Arg Glu Phe
                245                 250                 255

Leu Met Glu Lys Ile Gln Glu Val Val Thr Glu Arg Glu Arg Met Tyr
            260                 265                 270

Asp Glu Met Lys Lys Ile Glu Gly Val Glu Val Phe Pro Ser Lys Ala
        275                 280                 285

Asn Phe Leu Leu Phe Arg Thr Pro Tyr Pro Ala His Glu Val Tyr Gln
    290                 295                 300

Glu Leu Leu Lys Arg Asp Val Leu Val Arg Asn Val Ser Tyr Met Glu
305                 310                 315                 320

Gly Leu Gln Lys Cys Leu Arg Val Ser Val Gly Lys Pro Glu Glu Asn
                325                 330                 335
```

```
Asn Lys Phe Leu Glu Ala Leu Glu Glu Ser Ile Lys Ser Leu Ser Ser
            340                 345                 350

Ser Leu
```

(2) INFORMATION FOR SEQ ID NO:32:

(i) SEQUENCE CHARACTERISTICS:
        (A) LENGTH: 303 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:32:

```
Met Lys Pro Tyr Ala Lys Tyr Ile Trp Leu Asp Gly Arg Ile Leu Lys
 1               5                  10                  15

Trp Glu Asp Ala Lys Ile His Val Leu Thr His Ala Leu His Tyr Gly
            20                  25                  30

Thr Ser Ile Phe Glu Gly Ile Arg Gly Tyr Trp Asn Gly Asp Asn Leu
        35                  40                  45

Leu Val Phe Arg Leu Glu Glu His Ile Asp Arg Met Tyr Arg Ser Ala
    50                  55                  60

Lys Ile Leu Gly Ile Asn Ile Pro Tyr Thr Arg Glu Val Arg Gln
 65                  70                  75                  80

Ala Val Leu Glu Thr Ile Lys Ala Asn Asn Phe Arg Glu Asp Val Tyr
                85                  90                  95

Ile Arg Pro Val Ala Phe Val Ala Ser Gln Thr Val Thr Leu Asp Ile
                100                 105                 110

Arg Asn Leu Glu Val Ser Leu Ala Val Ile Val Phe Pro Phe Gly Lys
            115                 120                 125

Tyr Leu Ser Pro Asn Gly Ile Lys Ala Thr Ile Val Ser Trp Arg Arg
130                 135                 140

Val His Asn Thr Met Leu Pro Val Met Ala Lys Ile Gly Gly Ile Tyr
145                 150                 155                 160

Val Asn Ser Val Leu Ala Leu Val Glu Ala Arg Ser Arg Gly Phe Asp
                165                 170                 175

Glu Ala Leu Leu Met Asp Val Asn Gly Tyr Val Val Glu Gly Ser Gly
            180                 185                 190

Glu Asn Ile Phe Ile Val Arg Gly Gly Arg Leu Phe Thr Pro Pro Val
        195                 200                 205

His Glu Ser Ile Leu Glu Gly Ile Thr Arg Asp Thr Val Ile Lys Leu
    210                 215                 220

Ser Gly Asp Val Gly Leu Arg Val Glu Glu Lys Pro Ile Thr Arg Glu
225                 230                 235                 240

Glu Val Tyr Thr Ala Asp Glu Val Phe Leu Val Gly Thr Ala Ala Glu
                245                 250                 255

Ile Thr Pro Val Val Glu Val Asp Gly Arg Thr Ile Gly Thr Gly Lys
                260                 265                 270

Pro Gly Pro Ile Thr Thr Lys Ile Ala Glu Leu Tyr Ser Asn Val Val
            275                 280                 285

Arg Gly Lys Val Glu Lys Tyr Leu Asn Trp Ile Thr Pro Val Tyr
        290                 295                 300
```

(2) INFORMATION FOR SEQ ID NO:33:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (ii) MOLECULE TYPE: cDNA (ix) FEATURE:

(xi) SEQUENCE DESCRIPTION: SEQ ID NO:33:

```
CCGAGAATTC ATTAAAGAGG AGAAATTAAC TATGGCAGTC AAAGTGCGGC CT            52
```

(2) INFORMATION FOR SEQ ID NO:34:

(i) SEQUENCE CHARACTERISTICS:
        (A) LENGTH: 31 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
CGGAGGATCC TTATCCAAAG CTTCCAGGAA G                                   31
```

(2) INFORMATION FOR SEQ ID NO:35:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1089

(xi) SEQUENCE DESCRIPTION: SEQ ID NO:35:

```
ATG GCA GTC AAA GTG CGG CCT GAG CTC AGC CAG GTG GAG ATC TAC CGT      48
Met Ala Val Lys Val Arg Pro Glu Leu Ser Gln Val Glu Ile Tyr Arg
 1               5                  10                  15

CCC GGC AAA CCC ATC GAA GAG GTA AAG AAG GAG CTG GGG CTG GAG GAG      96
Pro Gly Lys Pro Ile Glu Glu Val Lys Lys Glu Leu Gly Leu Glu Glu
             20                  25                  30

GTA GTC AAG CTG GCC TCC AAC GAG AAC CCT CTG GGA CCT TCT CCC AAG     144
Val Val Lys Leu Ala Ser Asn Glu Asn Pro Leu Gly Pro Ser Pro Lys
         35                  40                  45

GCC GTG GCG GCG CTG GAG GGA CTG GAC CAC TGG CAC CTT TAC CCA GAA     192
Ala Val Ala Ala Leu Glu Gly Leu Asp His Trp His Leu Tyr Pro Glu
     50                  55                  60

GGC TCA AGC TAT GAG CTA CGG CAG GCG CTG GGT AAG AAA CTG GAG ATA     240
Gly Ser Ser Tyr Glu Leu Arg Gln Ala Leu Gly Lys Lys Leu Glu Ile
 65                  70                  75                  80

GAC CCG GAC AGC ATC ATC GTG GGT TGC GGC TCA AGC GAA GTC ATC CAG     288
Asp Pro Asp Ser Ile Ile Val Gly Cys Gly Ser Ser Glu Val Ile Gln
                 85                  90                  95

ATG CTC TCT TTG GCC CTG CTG GCG CCC GGC GAC GAG GTG GTC ATC CCT     336
Met Leu Ser Leu Ala Leu Leu Ala Pro Gly Asp Glu Val Val Ile Pro
            100                 105                 110

GTG CCT ACC TTT CCC CGC TAT GAG CCC CTG GCA CGG CTC ATG GGG GCT     384
Val Pro Thr Phe Pro Arg Tyr Glu Pro Leu Ala Arg Leu Met Gly Ala
        115                 120                 125

AAT CCC GTA AAA GTT CCC TTG AAG GAC TAC CGC ATC GAT GTG GAG GCA     432
```

```
                                                                        -continued Asn Pro Val Lys Val Pro Leu Lys Asp Tyr Arg Ile Asp Val Glu Ala
        130                 135                 140

GTG GCC CGA GCC CTT TCC CCC CGT ACC AAG CTG GTC TAC CTA TGC AAC              480
Val Ala Arg Ala Leu Ser Pro Arg Thr Lys Leu Val Tyr Leu Cys Asn
145                 150                 155                 160

CCC AAC AAC CCC ACC GGG ACC ATC GTC ACC CGG GAG GAG GTG GAG TGG              528
Pro Asn Asn Pro Thr Gly Thr Ile Val Thr Arg Glu Glu Val Glu Trp
                    165                 170                 175

TTC TTG GAA AAG GCG GGG GAG GGG GTT CTC ACC GTG CTG GAC GAG GCC              576
Phe Leu Glu Lys Ala Gly Glu Gly Val Leu Thr Val Leu Asp Glu Ala
            180                 185                 190

TAC TGC GAG TAC GTG ACC AGC CCC GCC TAC CCT GAT GGG CTC GAT TTC              624
Tyr Cys Glu Tyr Val Thr Ser Pro Ala Tyr Pro Asp Gly Leu Asp Phe
        195                 200                 205

CTG CGC CGG GGC TAC AAT GTG GTG GTG CTG CGC ACC TTC TCC AAG ATC              672
Leu Arg Arg Gly Tyr Asn Val Val Val Leu Arg Thr Phe Ser Lys Ile
    210                 215                 220

TAC GGG CTG GCC GGG CTG CGC ATA GGG TAC GGT GTG GCG GAC AGG GAG              720
Tyr Gly Leu Ala Gly Leu Arg Ile Gly Tyr Gly Val Ala Asp Arg Glu
225                 230                 235                 240

CTG GTG GCG GAA CTG CAC CGG GTG CGG GAG CCT TTC AAT GTC AGT TCC              768
Leu Val Ala Glu Leu His Arg Val Arg Glu Pro Phe Asn Val Ser Ser
                245                 250                 255

GCT GCT CAG ATA GCC GCC CTG GCC GCC CTG GAA GAC GAA GAG TTC GTG              816
Ala Ala Gln Ile Ala Ala Leu Ala Ala Leu Glu Asp Glu Glu Phe Val
            260                 265                 270

GCG CTT TCG CGC CAG GTC AAC GAA GAA GGG AAG GTT TTT CTC TAC CGA              864
Ala Leu Ser Arg Gln Val Asn Glu Glu Gly Lys Val Phe Leu Tyr Arg
        275                 280                 285

GAA CTG GAG AGG CGG GGG ATC GCC TAC GTG CCC ACC GAG GCC AAC TTC              912
Glu Leu Glu Arg Arg Gly Ile Ala Tyr Val Pro Thr Glu Ala Asn Phe
    290                 295                 300

CTA CTC TTC GAT GCC GGT CGG GAC GAG CAG GAA GTA TTT CGC CGG ATG              960
Leu Leu Phe Asp Ala Gly Arg Asp Glu Gln Glu Val Phe Arg Arg Met
305                 310                 315                 320

CTG CGC CAG GGA GTG ATC ATC CGG GNC GGG GTG GGT TAT CCC ACC CAC             1008
Leu Arg Gln Gly Val Ile Ile Arg Xaa Gly Val Gly Tyr Pro Thr His
                325                 330                 335

TTA AGG GTG ACC ATC GGC ACC TTG GAA CAG AAC CAG CGC TTC CTG GAA             1056
Leu Arg Val Thr Ile Gly Thr Leu Glu Gln Asn Gln Arg Phe Leu Glu
            340                 345                 350

GCT TTG GAT AAG GCT CTA GAG CTT AGG GGG GTT TAA                             1092
Ala Leu Asp Lys Ala Leu Glu Leu Arg Gly Val
        355                 360

(2) INFORMATION FOR SEQ ID NO:36:

(i) SEQUENCE CHARACTERISTICS:
        (A) LENGTH: 363 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:36:

Met Ala Val Lys Val Arg Pro Glu Leu Ser Gln Val Glu Ile Tyr Arg
  1               5                  10                  15

Pro Gly Lys Pro Ile Glu Glu Val Lys Lys Glu Leu Gly Leu Glu Glu
            20                  25                  30
```

```
Val Val Lys Leu Ala Ser Asn Glu Asn Pro Leu Gly Pro Ser Pro Lys
         35                  40                  45

Ala Val Ala Ala Leu Glu Gly Leu Asp His Trp His Leu Tyr Pro Glu
     50                  55                  60

Gly Ser Ser Tyr Glu Leu Arg Gln Ala Leu Gly Lys Lys Leu Glu Ile
 65                  70                  75                  80

Asp Pro Asp Ser Ile Ile Val Gly Cys Gly Ser Ser Glu Val Ile Gln
                 85                  90                  95

Met Leu Ser Leu Ala Leu Leu Ala Pro Gly Asp Glu Val Val Ile Pro
                100                 105                 110

Val Pro Thr Phe Pro Arg Tyr Glu Pro Leu Ala Arg Leu Met Gly Ala
            115                 120                 125

Asn Pro Val Lys Val Pro Leu Lys Asp Tyr Arg Ile Asp Val Glu Ala
        130                 135                 140

Val Ala Arg Ala Leu Ser Pro Arg Thr Lys Leu Val Tyr Leu Cys Asn
145                 150                 155                 160

Pro Asn Asn Pro Thr Gly Thr Ile Val Thr Arg Glu Glu Val Glu Trp
                165                 170                 175

Phe Leu Glu Lys Ala Gly Glu Gly Val Leu Thr Val Leu Asp Glu Ala
                180                 185                 190

Tyr Cys Glu Tyr Val Thr Ser Pro Ala Tyr Pro Asp Gly Leu Asp Phe
            195                 200                 205

Leu Arg Arg Gly Tyr Asn Val Val Val Leu Arg Thr Phe Ser Lys Ile
        210                 215                 220

Tyr Gly Leu Ala Gly Leu Arg Ile Gly Tyr Gly Val Ala Asp Arg Glu
225                 230                 235                 240

Leu Val Ala Glu Leu His Arg Val Arg Glu Pro Phe Asn Val Ser Ser
                245                 250                 255

Ala Ala Gln Ile Ala Ala Leu Ala Ala Leu Glu Asp Glu Glu Phe Val
                260                 265                 270

Ala Leu Ser Arg Gln Val Asn Glu Glu Gly Lys Val Phe Leu Tyr Arg
            275                 280                 285

Glu Leu Glu Arg Arg Gly Ile Ala Tyr Val Pro Thr Glu Ala Asn Phe
290                 295                 300

Leu Leu Phe Asp Ala Gly Arg Asp Glu Gln Glu Val Phe Arg Arg Met
305                 310                 315                 320

Leu Arg Gln Gly Val Ile Ile Arg Xaa Gly Val Gly Tyr Pro Thr His
                325                 330                 335

Leu Arg Val Thr Ile Gly Thr Leu Glu Gln Asn Gln Arg Phe Leu Glu
            340                 345                 350

Ala Leu Asp Lys Ala Leu Glu Leu Arg Gly Val
        355                 360
```

(2) INFORMATION FOR SEQ ID NO:37:

(i) SEQUENCE CHARACTERISTICS:
        (A) LENGTH: 52 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
CCGAGAATTC ATTAAAGAGG AGAAATTAAC TATGAGAAAA GGACTTGCAA GT        52
```

(2) INFORMATION FOR SEQ ID NO:38:

(i) SEQUENCE CHARACTERISTICS:
        (A) LENGTH: 31 NUCLEOTIDES
        (B) TYPE: nucleic acid
        (C) STRANDEDNESS: single
        (D) TOPOLOGY: linear (ii) MOLECULE TYPE: NUCLEIC ACID (xi) SEQUENCE DESCRIPTION: SEQ ID NO:38:

```
CGGAGGATCC TTAGATCTCT TCAAGGGCTT T                              31
```

(2) INFORMATION FOR SEQ ID NO:39:

(i) SEQUENCE CHARACTERISTICS:
        (A) LENGTH: 1185 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...1182

(xi) SEQUENCE DESCRIPTION: SEQ ID NO:39:

```
ATG AGA AAA GGA CTT GCA AGT AGG GTA AGT CAC CTA AAA CCT TCC CCC        48
Met Arg Lys Gly Leu Ala Ser Arg Val Ser His Leu Lys Pro Ser Pro
 1               5                  10                  15

ACG CTG ACC ATA ACC GCA AAA GCA AAA GAA TTA AGG GCT AAA GGA GTG        96
Thr Leu Thr Ile Thr Ala Lys Ala Lys Glu Leu Arg Ala Lys Gly Val
                20                  25                  30

GAC GTT ATA GGT TTT GGA GCG GGA GAA CCT GAC TTC GAC ACA CCC GAC       144
Asp Val Ile Gly Phe Gly Ala Gly Glu Pro Asp Phe Asp Thr Pro Asp
            35                  40                  45

TTC ATA AAG GAA GCC TGT ATA AGG GCT TTA AGG GAA GGA AAG ACC AAG       192
Phe Ile Lys Glu Ala Cys Ile Arg Ala Leu Arg Glu Gly Lys Thr Lys
        50                  55                  60

TAC GCT CCC TCC GCG GGA ATA CCA GAG CTC AGA GAA GCT ATA GCT GAA       240
Tyr Ala Pro Ser Ala Gly Ile Pro Glu Leu Arg Glu Ala Ile Ala Glu
65                  70                  75                  80

AAA CTA CTG AAA GAA AAC AAA GTT GAG TAC AAA CCT TCA GAG ATA GTC       288
Lys Leu Leu Lys Glu Asn Lys Val Glu Tyr Lys Pro Ser Glu Ile Val
                85                  90                  95

GTT TCC GCA GGA GCG AAA ATG GTT CTC TTC CTC ATA TTC ATG GCT ATA       336
Val Ser Ala Gly Ala Lys Met Val Leu Phe Leu Ile Phe Met Ala Ile
            100                 105                 110

CTG GAC GAA GGA GAC GAG GTT TTA CTA CCT AGC CCT TAC TGG GTA ACT       384
Leu Asp Glu Gly Asp Glu Val Leu Leu Pro Ser Pro Tyr Trp Val Thr
        115                 120                 125

TAC CCC GAA CAG ATA AGG TTC TTC GGA GGG GTT CCC GTT GAG GTT CCT       432
Tyr Pro Glu Gln Ile Arg Phe Phe Gly Gly Val Pro Val Glu Val Pro
    130                 135                 140

CTA AAG AAA GAG AAA GGA TTT CAA TTA AGT CTG GAA GAT GTG AAA GAA       480
Leu Lys Lys Glu Lys Gly Phe Gln Leu Ser Leu Glu Asp Val Lys Glu
145                 150                 155                 160

AAG GTT ACG GAG AGA ACA AAA GCT ATA GTC ATA AAC TCT CCG AAC AAC       528
Lys Val Thr Glu Arg Thr Lys Ala Ile Val Ile Asn Ser Pro Asn Asn
                165                 170                 175

CCC ACT GGT GCT GTT TAC GAA GAG GAG GAA CTT AAG AAA ATA GCG GAG       576
Pro Thr Gly Ala Val Tyr Glu Glu Glu Glu Leu Lys Lys Ile Ala Glu
            180                 185                 190
```

```
TTT TGC GTG GAG AGG GGC ATT TTC ATA ATT TCC GAT GAG TGC TAT GAG      624
Phe Cys Val Glu Arg Gly Ile Phe Ile Ile Ser Asp Glu Cys Tyr Glu
            195                 200                 205

TAC TTC GTT TAC GGT GAT GCA AAA TTT GTT AGC CCT GCC TCT TTC TCG      672
Tyr Phe Val Tyr Gly Asp Ala Lys Phe Val Ser Pro Ala Ser Phe Ser
    210                 215                 220

GAT GAA GTA AAG AAC ATA ACC TTC ACG GTA AAC GCC TTT TCG AAG AGC      720
Asp Glu Val Lys Asn Ile Thr Phe Thr Val Asn Ala Phe Ser Lys Ser
225                 230                 235                 240

TAT TCC ATG ACT GGT TGG CGA ATA GGT TAT GTA GCG TGC CCC GAA GAG      768
Tyr Ser Met Thr Gly Trp Arg Ile Gly Tyr Val Ala Cys Pro Glu Glu
                245                 250                 255

TAC GCA AAA GTG ATA GCG AGT CTT AAC AGC CAG AGT GTT TCC AAC GTC      816
Tyr Ala Lys Val Ile Ala Ser Leu Asn Ser Gln Ser Val Ser Asn Val
        260                 265                 270

ACT ACC TTT GCC CAG TAT GGA GCT CTT GAG GCC TTG AAA AAT CCA AAG      864
Thr Thr Phe Ala Gln Tyr Gly Ala Leu Glu Ala Leu Lys Asn Pro Lys
            275                 280                 285

TCT AAA GAT TTT GTA AAC GAA ATG AGA AAT GCT TTT GAA AGG AGA AGG      912
Ser Lys Asp Phe Val Asn Glu Met Arg Asn Ala Phe Glu Arg Arg Arg
290                 295                 300

GAT ACG GCT GTA GAA GAG CTT TCT AAA ATT CCA GGT ATG GAT GTG GTA      960
Asp Thr Ala Val Glu Glu Leu Ser Lys Ile Pro Gly Met Asp Val Val
305                 310                 315                 320

AAA CCC GAA GGT GCC TTT TAC ATA TTT CCG GAC TTC TCC GCT TAC GCT     1008
Lys Pro Glu Gly Ala Phe Tyr Ile Phe Pro Asp Phe Ser Ala Tyr Ala
                325                 330                 335

GAG AAA CTG GGT GGT GAT GTG AAA CTC TCG GAG TTC CTT CTG GAA AAG     1056
Glu Lys Leu Gly Gly Asp Val Lys Leu Ser Glu Phe Leu Leu Glu Lys
        340                 345                 350

GCT AAG GTT GCG GTG GTT CCC GGT TCG GCC TTC GGA GCT CCC GGA TTT     1104
Ala Lys Val Ala Val Val Pro Gly Ser Ala Phe Gly Ala Pro Gly Phe
            355                 360                 365

TTG AGG CTT TCT TAC GCC CTT TCC GAG GAA AGA CTC GTT GAG GGT ATA     1152
Leu Arg Leu Ser Tyr Ala Leu Ser Glu Glu Arg Leu Val Glu Gly Ile
370                 375                 380

AGG AGA ATA AAG AAA GCC CTT GAA GAG ATC TAA                         1185
Arg Arg Ile Lys Lys Ala Leu Glu Glu Ile
385                 390
```

(2) INFORMATION FOR SEQ ID NO:40:

(i) SEQUENCE CHARACTERISTICS:
        (A) LENGTH: 394 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:40:

```
Met Arg Lys Gly Leu Ala Ser Arg Val Ser His Leu Lys Pro Ser Pro
 1               5                  10                  15

Thr Leu Thr Ile Thr Ala Lys Ala Lys Glu Leu Arg Ala Lys Gly Val
                20                  25                  30

Asp Val Ile Gly Phe Gly Ala Gly Glu Pro Asp Phe Asp Thr Pro Asp
            35                  40                  45

Phe Ile Lys Glu Ala Cys Ile Arg Ala Leu Arg Glu Gly Lys Thr Lys
        50                  55                  60

Tyr Ala Pro Ser Ala Gly Ile Pro Glu Leu Arg Glu Ala Ile Ala Glu
```

```
             65                  70                  75                  80
Lys Leu Leu Lys Glu Asn Lys Val Glu Tyr Lys Pro Ser Glu Ile Val
                        85                  90                  95
Val Ser Ala Gly Ala Lys Met Val Leu Phe Leu Ile Phe Met Ala Ile
                100                 105                 110
Leu Asp Glu Gly Asp Glu Val Leu Leu Pro Ser Pro Tyr Trp Val Thr
            115                 120                 125
Tyr Pro Glu Gln Ile Arg Phe Phe Gly Gly Val Pro Val Glu Val Pro
        130                 135                 140
Leu Lys Lys Glu Lys Gly Phe Gln Leu Ser Leu Glu Asp Val Lys Glu
145                 150                 155                 160
Lys Val Thr Glu Arg Thr Lys Ala Ile Val Ile Asn Ser Pro Asn Asn
                165                 170                 175
Pro Thr Gly Ala Val Tyr Glu Glu Glu Leu Lys Lys Ile Ala Glu
            180                 185                 190
Phe Cys Val Glu Arg Gly Ile Phe Ile Ile Ser Asp Glu Cys Tyr Glu
        195                 200                 205
Tyr Phe Val Tyr Gly Asp Ala Lys Phe Val Ser Pro Ala Ser Phe Ser
    210                 215                 220
Asp Glu Val Lys Asn Ile Thr Phe Thr Val Asn Ala Phe Ser Lys Ser
225                 230                 235                 240
Tyr Ser Met Thr Gly Trp Arg Ile Gly Tyr Val Ala Cys Pro Glu Glu
                245                 250                 255
Tyr Ala Lys Val Ile Ala Ser Leu Asn Ser Gln Ser Val Ser Asn Val
            260                 265                 270
Thr Thr Phe Ala Gln Tyr Gly Ala Leu Glu Ala Leu Lys Asn Pro Lys
        275                 280                 285
Ser Lys Asp Phe Val Asn Glu Met Arg Asn Ala Phe Glu Arg Arg Arg
    290                 295                 300
Asp Thr Ala Val Glu Glu Leu Ser Lys Ile Pro Gly Met Asp Val Val
305                 310                 315                 320
Lys Pro Glu Gly Ala Phe Tyr Ile Phe Pro Asp Phe Ser Ala Tyr Ala
                325                 330                 335
Glu Lys Leu Gly Gly Asp Val Lys Leu Ser Glu Phe Leu Leu Glu Lys
            340                 345                 350
Ala Lys Val Ala Val Val Pro Gly Ser Ala Phe Gly Ala Pro Gly Phe
        355                 360                 365
Leu Arg Leu Ser Tyr Ala Leu Ser Glu Glu Arg Leu Val Glu Gly Ile
    370                 375                 380
Arg Arg Ile Lys Lys Ala Leu Glu Glu Ile
385                 390
```

(2) INFORMATION FOR SEQ ID NO:41:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

CCGAGAATTC ATTAAAGAGG AGAAATTAAC TATGAGAAAA GGACTTGCAA GT    52

(2) INFORMATION FOR SEQ ID NO:42:

```
    (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

CGGAGGATCC TTAGATCTCT TCAAGGGCTT T                                           31
```